United States Patent
Van Leeuwen et al.

(10) Patent No.: US 10,913,938 B2
(45) Date of Patent: Feb. 9, 2021

(54) POLYPEPTIDES HAVING CELLULOLYTIC ENHANCING ACTIVITY AND USES THEREOF

(71) Applicant: DSM IP ASSETS B.V., Heerlen (NL)

(72) Inventors: Johannes Gustaaf Ernst Van Leeuwen, Echt (NL); Loes Elizabeth Bevers, Echt (NL)

(73) Assignee: DSM IP ASSETS B.V., Heerlen (NL)

( * ) Notice: Subject to any disclaimer, the term of this patent is extended or adjusted under 35 U.S.C. 154(b) by 0 days.

(21) Appl. No.: 16/318,776

(22) PCT Filed: Jul. 27, 2017

(86) PCT No.: PCT/EP2017/069049
§ 371 (c)(1),
(2) Date: Jan. 18, 2019

(87) PCT Pub. No.: WO2018/019948
PCT Pub. Date: Feb. 1, 2018

(65) Prior Publication Data
US 2019/0345461 A1    Nov. 14, 2019

(30) Foreign Application Priority Data

Jul. 29, 2016 (EP) .................................. 16181919
Jul. 29, 2016 (EP) .................................. 16181920
(Continued)

(51) Int. Cl.
*C12N 9/02*    (2006.01)
*C12N 9/42*    (2006.01)
(Continued)

(52) U.S. Cl.
CPC .............. *C12N 9/0083* (2013.01); *C12N 1/14* (2013.01); *C12N 9/2437* (2013.01); *C12N 15/52* (2013.01);
(Continued)

(58) Field of Classification Search
None
See application file for complete search history.

(56) References Cited

U.S. PATENT DOCUMENTS

2019/0345461 A1* 11/2019 Van Leeuwen ...... C12N 9/2437

FOREIGN PATENT DOCUMENTS

WO    2012/021394 A1    2/2012
WO    2012/159009 A1    11/2012
(Continued)

OTHER PUBLICATIONS

International Search Report of International Patent Application No. PCT/EP2017/069049 dated Oct. 2, 2017.

*Primary Examiner* — Richard C Ekstrom
(74) *Attorney, Agent, or Firm* — Mcbee Moore & Vanik IP, LLC

(57) ABSTRACT

The invention relates to a polypeptide having cellulolytic enhancing activity, wherein the polypeptide is selected from the group consisting of: (a) a polypeptide comprising an amino acid sequence having at least 60% sequence identity with the amino acid sequence of SEQ ID NO: 2, 5, 8, 11, 14, 17, 20, 23, 26, 29, 32, 35, 38, 41, 44 and/or 47; (b) a polypeptide encoded by a polynucleotide comprising a nucleotide sequence having at least 60% sequence identity to the nucleotide sequence of SEQ ID NO: 3, 6, 9, 12, 15, 18, 21, 24, 27, 30, 33, 36, 39, 42, 45 and/or 48; (c) a polypeptide encoded by a polynucleotide comprising a nucleotide sequence which hybridises under at least high stringency conditions with the complementary strand of
(Continued)

SEQ ID NO: 3, 6, 9, 12, 15, 18, 21, 24, 27, 30, 33, 36, 39, 42, 45 and/or 48; and (d) a fragment of the polypeptide of (a), (b), or (c), that has cellulolytic enhancing activity.

20 Claims, 2 Drawing Sheets

Specification includes a Sequence Listing.

(30) Foreign Application Priority Data

| Jul. 29, 2016 | (EP) | 16181921 |
|---|---|---|
| Jul. 29, 2016 | (EP) | 16181922 |
| Jul. 29, 2016 | (EP) | 16181927 |
| Jul. 29, 2016 | (EP) | 16181929 |
| Jul. 29, 2016 | (EP) | 16181930 |
| Jul. 29, 2016 | (EP) | 16181931 |
| Jul. 29, 2016 | (EP) | 16181977 |
| Jul. 29, 2016 | (EP) | 16181978 |
| Jul. 29, 2016 | (EP) | 16181980 |
| Jul. 29, 2016 | (EP) | 16181982 |
| Jul. 29, 2016 | (EP) | 16181984 |
| Jul. 29, 2016 | (EP) | 16181985 |
| Jul. 29, 2016 | (EP) | 16181987 |
| Jul. 29, 2016 | (EP) | 16181991 |

(51) Int. Cl.
  *C12N 1/14* (2006.01)
  *C12N 15/52* (2006.01)
  *C12N 15/80* (2006.01)
  *C12P 7/10* (2006.01)
  *C12P 19/14* (2006.01)

(52) U.S. Cl.
  CPC .............. *C12N 15/80* (2013.01); *C12P 7/10* (2013.01); *C12P 19/14* (2013.01); *C12P 2203/00* (2013.01)

(56) References Cited

FOREIGN PATENT DOCUMENTS

| WO | 2014/138983 A1 | 9/2014 |
| WO | 2014/140165 A1 | 9/2014 |

\* cited by examiner

SEQUENCE LISTING

<160> NUMBER OF SEQ ID NOS: 48

<210> SEQ ID NO 1
<211> LENGTH: 256
<212> TYPE: PRT
<213> ORGANISM: Artificial sequence

```
<220> FEATURE:
<223> OTHER INFORMATION: Full length sequence of enzyme having
      cellulolytic enhancing activity

<400> SEQUENCE: 1

Met Leu Ser Ser Ala Leu Ala Leu Ala Gly Val Leu Ser Ala
1               5                   10                  15

Pro Phe Val Ser Ala His Gly Phe Val Gln Gly Ile Val Val Gly Asp
                20                  25                  30

Lys Phe Tyr Ser Gly Tyr Ile Val Asn Glu Phe Pro Tyr Glu Ser Asp
                35                  40                  45

Pro Pro Pro Val Ile Gly Trp Ala Thr Thr Ala Thr Asp Leu Gly Phe
50                  55                  60

Val Asp Gly Thr Glu Tyr Ala Glu Pro Asp Ile Ile Cys His Arg Asn
65                  70                  75                  80

Ala Thr Pro Ala Leu Leu Thr Ala Pro Val Ala Ala Gly Gly Thr Val
                85                  90                  95

Glu Leu Gln Trp Thr Pro Trp Pro Ser Ser His Gly Pro Val Ile
                100                 105                 110

Thr Tyr Leu Ala Pro Cys Asn Gly Asp Cys Thr Glu Val Asp Lys Thr
                115                 120                 125

Thr Leu Lys Phe Phe Lys Ile Asp Gln Gly Gly Leu Val Asn Asp Thr
130                 135                 140

Asp Pro Pro Gly Val Trp Ala Ser Asp Glu Leu Ile Ser Asn Asn Asn
145                 150                 155                 160

Thr Trp Thr Val Thr Ile Pro Thr Ser Leu Ala Pro Gly Gly Tyr Val
                165                 170                 175

Leu Arg His Glu Ile Ile Ala Leu His Ser Ala Glu Gln Leu Asn Gly
                180                 185                 190

Ala Gln Asn Tyr Pro Gln Cys Ile Asn Ile Gln Val Thr Gln Thr Ser
                195                 200                 205

Gly Thr Val Thr Pro Ser Gly Thr Leu Gly Glu Ala Leu Tyr Thr Asn
                210                 215                 220

Thr Ala Pro Gly Ile Ile Ile Asp Ile Tyr Glu Pro Ile Ala Thr Tyr
225                 230                 235                 240

Thr Ile Pro Gly Pro Pro Met Tyr Thr Gly Ala Ile Ser Thr Asn Glu
                245                 250                 255

<210> SEQ ID NO 2
<211> LENGTH: 235
<212> TYPE: PRT
<213> ORGANISM: Artificial sequence
<220> FEATURE:
<223> OTHER INFORMATION: Mature sequence of enzyme having cellulolytic
      enhancing activity

<400> SEQUENCE: 2

His Gly Phe Val Gln Gly Ile Val Val Gly Asp Lys Phe Tyr Ser Gly
1               5                   10                  15

Tyr Ile Val Asn Glu Phe Pro Tyr Glu Ser Asp Pro Pro Val Ile
                20                  25                  30

Gly Trp Ala Thr Thr Ala Thr Asp Leu Gly Phe Val Asp Gly Thr Glu
                35                  40                  45

Tyr Ala Glu Pro Asp Ile Ile Cys His Arg Asn Ala Thr Pro Ala Leu
                50                  55                  60

Leu Thr Ala Pro Val Ala Ala Gly Gly Thr Val Glu Leu Gln Trp Thr
65                  70                  75                  80
```

Pro Trp Pro Ser Ser His His Gly Pro Val Ile Thr Tyr Leu Ala Pro
                85                  90                  95

Cys Asn Gly Asp Cys Thr Glu Val Asp Lys Thr Thr Leu Lys Phe Phe
            100                 105                 110

Lys Ile Asp Gln Gly Gly Leu Val Asn Asp Thr Asp Pro Pro Gly Val
        115                 120                 125

Trp Ala Ser Asp Glu Leu Ile Ser Asn Asn Thr Trp Thr Val Thr
    130                 135                 140

Ile Pro Thr Ser Leu Ala Pro Gly Gly Tyr Val Leu Arg His Glu Ile
145                 150                 155                 160

Ile Ala Leu His Ser Ala Glu Gln Leu Asn Gly Ala Gln Asn Tyr Pro
                165                 170                 175

Gln Cys Ile Asn Ile Gln Val Thr Gln Thr Ser Gly Thr Val Thr Pro
            180                 185                 190

Ser Gly Thr Leu Gly Glu Ala Leu Tyr Thr Asn Thr Ala Pro Gly Ile
        195                 200                 205

Ile Ile Asp Ile Tyr Glu Pro Ile Ala Thr Tyr Thr Ile Pro Gly Pro
210                 215                 220

Pro Met Tyr Thr Gly Ala Ile Ser Thr Asn Glu
225                 230                 235

<210> SEQ ID NO 3
<211> LENGTH: 771
<212> TYPE: DNA
<213> ORGANISM: Artificial sequence
<220> FEATURE:
<223> OTHER INFORMATION: Coding sequence for full length enzyme having
      cellulolytic enhancing activity

<400> SEQUENCE: 3
atgctctcct ccgccctggc ccttgccggt gttctccttt cttctgctcc cttcgtcagc      60
gctcacggat tcgtccaggg cattgttgtc ggtgacaagt tctactctgg ctacatcgtc     120
aacgagttcc cctacgagag cgaccctcct cccgtcattg gctgggccac cactgccacc     180
gatcttggat tcgtcgatgg caccgaatac gctgagcctg acatcatctg ccaccgcaac     240
gccactcccg ccttgttgac tgctcccgtt gctgctggtg gtaccgttga gctccagtgg     300
actccctggc ccagcagcca ccacggtccc gtcatcacct accttgctcc ttgcaacggt     360
gactgcaccg aggttgacaa gaccacccc aagttcttca agatcgacca gggtggcctg     420
gtcaacgaca ccgaccctcc cggtgtgtgg gcgtcggatg agctgatctc caacaacaac     480
acctggactg tcaccattcc tacctccctc gcccccggtg gatacgtgct gcgtcacgaa     540
atcattgccc tccactccgc cgagcagctg aacggtgctc agaactaccc ccagtgcatc     600
aacatccagg tgacccagac ttctggcacc gtcaccccct ccggcaccct gggcgaggct     660
ctctacacca acactgctcc tggtatcatc atcgatatct acgagcccat tgccacctac     720
accatccccg gtcctcccat gtacactggt gccatctcca ccaacgaata a              771

<210> SEQ ID NO 4
<211> LENGTH: 256
<212> TYPE: PRT
<213> ORGANISM: Artificial sequence
<220> FEATURE:
<223> OTHER INFORMATION: Full length sequence of enzyme having
      cellulolytic enhancing activity

<400> SEQUENCE: 4

Met Leu Ser Ser Ala Leu Ala Leu Ala Gly Val Leu Leu Ser Ser Ala
1               5                   10                  15

Pro Phe Val Ser Ala His Gly Phe Val Gln Gly Ile Val Ile Gly Asp
                20                  25                  30

Lys Phe Tyr Ser Gly Tyr Ile Val Asp Glu Tyr Pro Tyr Glu Ser Asp
            35                  40                  45

Pro Pro Pro Val Ile Gly Trp Ala Thr Thr Thr Asp Leu Gly Phe
50                  55                  60

Val Asp Gly Thr Glu Tyr Ala Glu Pro Asp Ile Ile Cys His Arg Asn
65                  70                  75                  80

Ala Thr Pro Ala Leu Leu Thr Ala Glu Val Lys Ala Gly Gly Thr Val
                85                  90                  95

Glu Leu Gln Trp Thr Pro Trp Pro Ser Ser His His Gly Pro Val Ile
                100                 105                 110

Thr Tyr Leu Ala Pro Cys Asn Gly Asn Cys Ser Glu Val Asp Lys Thr
            115                 120                 125

Thr Leu Glu Phe Phe Lys Ile Asp Gln Ser Gly Leu Val Asn Asp Ser
130                 135                 140

Asp Pro Pro Gly Val Trp Ala Ser Asp Glu Leu Ile Ser Asn Asn
145                 150                 155                 160

Thr Trp Thr Val Thr Ile Pro Thr Ser Ile Ala Pro Gly Gly Tyr Val
                165                 170                 175

Leu Arg His Glu Ile Ile Ala Leu His Ser Ala Glu Gln Leu Asp Gly
            180                 185                 190

Ala Gln Asn Tyr Pro Gln Cys Ile Asn Ile Glu Ile Thr Gln Thr Ser
                195                 200                 205

Gly Thr Val Thr Pro Thr Gly Thr Leu Gly Glu Ala Leu Tyr Thr Asp
210                 215                 220

Thr Ala Pro Gly Ile Leu Val Asp Ile Tyr Glu Pro Ile Ala Thr Tyr
225                 230                 235                 240

Thr Ile Pro Gly Pro Pro Met Tyr Thr Gly Ala Ile Ser Thr Asn Glu
                245                 250                 255

<210> SEQ ID NO 5
<211> LENGTH: 235
<212> TYPE: PRT
<213> ORGANISM: Artificial sequence
<220> FEATURE:
<223> OTHER INFORMATION: Mature sequence of enzyme having cellulolytic
      enhancing activity

<400> SEQUENCE: 5

His Gly Phe Val Gln Gly Ile Val Ile Gly Asp Lys Phe Tyr Ser Gly
1               5                   10                  15

Tyr Ile Val Asp Glu Tyr Pro Tyr Glu Ser Asp Pro Pro Val Ile
                20                  25                  30

Gly Trp Ala Thr Thr Ala Thr Asp Leu Gly Phe Val Asp Gly Thr Glu
            35                  40                  45

Tyr Ala Glu Pro Asp Ile Ile Cys His Arg Asn Ala Thr Pro Ala Leu
        50                  55                  60

Leu Thr Ala Glu Val Lys Ala Gly Gly Thr Val Glu Leu Gln Trp Thr
65                  70                  75                  80

Pro Trp Pro Ser Ser His His Gly Pro Val Ile Thr Tyr Leu Ala Pro
                85                  90                  95

Cys Asn Gly Asn Cys Ser Glu Val Asp Lys Thr Thr Leu Glu Phe Phe
                100                 105                 110

```
Lys Ile Asp Gln Ser Gly Leu Val Asn Asp Ser Asp Pro Pro Gly Val
            115                 120                 125

Trp Ala Ser Asp Glu Leu Ile Ser Asn Asn Asn Thr Trp Thr Val Thr
    130                 135                 140

Ile Pro Thr Ser Ile Ala Pro Gly Gly Tyr Val Leu Arg His Glu Ile
145                 150                 155                 160

Ile Ala Leu His Ser Ala Glu Gln Leu Asp Gly Ala Gln Asn Tyr Pro
            165                 170                 175

Gln Cys Ile Asn Ile Glu Ile Thr Gln Thr Ser Gly Thr Val Thr Pro
            180                 185                 190

Thr Gly Thr Leu Gly Glu Ala Leu Tyr Thr Asp Thr Ala Pro Gly Ile
            195                 200                 205

Leu Val Asp Ile Tyr Glu Pro Ile Ala Thr Tyr Thr Ile Pro Gly Pro
            210                 215                 220

Pro Met Tyr Thr Gly Ala Ile Ser Thr Asn Glu
225                 230                 235
```

<210> SEQ ID NO 6
<211> LENGTH: 771
<212> TYPE: DNA
<213> ORGANISM: Artificial sequence
<220> FEATURE:
<223> OTHER INFORMATION: Coding sequence for full length enzyme having cellulolytic enhancing activity

<400> SEQUENCE: 6

```
atgctcagct ctgctcttgc tcttgccggt gtcctcctct cctccgctcc cttcgtttcc      60
gcccacggat tcgtccaggg tatcgtcatc ggtgacaagt tctactctgg ctacatcgtc     120
gatgaatacc cctacgaatc ggatcctcct cccgtcattg ctgggccac cactgccacc      180
gatcttggat tcgttgatgg caccgaatac gctgagcctg acatcatctg ccaccgcaac     240
gccacccccg ccctcttgac tgctgaggtc aaggccggtg gtactgttga gctgcagtgg     300
actccctggc ccagctctca ccacggtccc gtcatcacct accttgctcc ttgcaacggc     360
aactgctctg aggttgacaa gaccaccctc gagttcttca gatcgacca gagcggtctg     420
gtcaacgact ccgaccctcc tggtgtgtgg gcctccgacg agctcatctc caacaacaac     480
acctggactg tcaccatccc tacctcgatt gccccggtg ctacgtgct ccgtcacgag       540
atcattgccc tgcactccgc tgagcagctg gatggtgctc agaactaccc ccagtgcatc     600
aacattgaga tcacccagac cagcggcacc gtcaccccca ctggcaccct gggcgaggct     660
ctctacaccg acactgctcc cggtatcctg gttgacatct acgagcccat tgccacctac     720
accatccccg gtcctcccat gtacactggt gccatctcca caacgagta a               771
```

<210> SEQ ID NO 7
<211> LENGTH: 256
<212> TYPE: PRT
<213> ORGANISM: Artificial sequence
<220> FEATURE:
<223> OTHER INFORMATION: Full length sequence of enzyme having cellulolytic enhancing activity

<400> SEQUENCE: 7

```
Met Leu Ser Ser Ala Leu Ala Leu Ala Gly Val Leu Leu Ser Ser Ala
1               5                   10                  15

Pro Phe Val Ser Ala His Gly Phe Val Ser Gly Ile Val Ile Gly Asp
            20                  25                  30
```

```
Lys Phe Tyr Ser Gly Tyr Ile Val Asp Glu Phe Pro Tyr Met Ser Asp
            35                  40                  45
Pro Pro Pro Val Ile Gly Trp Ala Thr Thr Ala Thr Asp Leu Gly Phe
    50                  55                  60
Val Asp Gly Thr Glu Tyr Ala Glu Pro Asp Ile Ile Cys His Arg Asn
 65                  70                  75                  80
Ala Thr Pro Ala Leu Leu Thr Ala Pro Val Ala Ala Gly Gly Asp Val
                85                  90                  95
Glu Leu Gln Trp Thr Pro Trp Pro Ser Ser His His Gly Pro Val Ile
            100                 105                 110
Thr Tyr Leu Ala Pro Cys Asn Gly Asn Cys Ser Glu Val Asp Lys Thr
        115                 120                 125
Thr Leu Lys Phe Phe Lys Ile Asp Glu Gly Gly Leu Val Asn Asp Thr
    130                 135                 140
Asp Val Pro Gly Thr Trp Ala Ser Asp Glu Leu Ile Ala Asn Asn Asn
145                 150                 155                 160
Ser Trp Thr Val Lys Ile Pro Thr Ser Ile Glu Pro Gly Gly Tyr Val
                165                 170                 175
Leu Arg His Glu Ile Ile Ala Leu His Ser Ala Glu Asn Leu Asp Gly
            180                 185                 190
Ala Gln Asn Tyr Pro Gln Cys Ile Asn Ile Lys Val Thr Gln Thr Ser
        195                 200                 205
Gly Thr Val Thr Pro Ser Gly Thr Leu Gly Thr Ala Leu Tyr Thr Asp
    210                 215                 220
Thr Ala Pro Gly Ile Leu Ile Asp Ile Tyr Glu Pro Ile Ala Thr Tyr
225                 230                 235                 240
Thr Ile Pro Gly Pro Pro Leu Tyr Thr Gly Ala Ile Ser Thr Asn Glu
                245                 250                 255

<210> SEQ ID NO 8
<211> LENGTH: 235
<212> TYPE: PRT
<213> ORGANISM: Artificial sequence
<220> FEATURE:
<223> OTHER INFORMATION: Mature sequence of enzyme having cellulolytic
      enhancing activity

<400> SEQUENCE: 8

His Gly Phe Val Ser Gly Ile Val Ile Gly Asp Lys Phe Tyr Ser Gly
 1               5                  10                  15
Tyr Ile Val Asp Glu Phe Pro Tyr Met Ser Asp Pro Pro Val Ile
                20                  25                  30
Gly Trp Ala Thr Thr Ala Thr Asp Leu Gly Phe Val Asp Gly Thr Glu
            35                  40                  45
Tyr Ala Glu Pro Asp Ile Ile Cys His Arg Asn Ala Thr Pro Ala Leu
        50                  55                  60
Leu Thr Ala Pro Val Ala Ala Gly Gly Asp Val Glu Leu Gln Trp Thr
 65                  70                  75                  80
Pro Trp Pro Ser Ser His His Gly Pro Val Ile Thr Tyr Leu Ala Pro
                85                  90                  95
Cys Asn Gly Asn Cys Ser Glu Val Asp Lys Thr Thr Leu Lys Phe Phe
            100                 105                 110
Lys Ile Asp Glu Gly Gly Leu Val Asn Asp Thr Asp Val Pro Gly Thr
        115                 120                 125
Trp Ala Ser Asp Glu Leu Ile Ala Asn Asn Asn Ser Trp Thr Val Lys
    130                 135                 140
```

```
Ile Pro Thr Ser Ile Glu Pro Gly Gly Tyr Val Leu Arg His Glu Ile
145                 150                 155                 160

Ile Ala Leu His Ser Ala Glu Asn Leu Asp Gly Ala Gln Asn Tyr Pro
                165                 170                 175

Gln Cys Ile Asn Ile Lys Val Thr Gln Thr Ser Gly Thr Val Thr Pro
            180                 185                 190

Ser Gly Thr Leu Gly Thr Ala Leu Tyr Thr Asp Thr Ala Pro Gly Ile
        195                 200                 205

Leu Ile Asp Ile Tyr Glu Pro Ile Ala Thr Tyr Thr Ile Pro Gly Pro
    210                 215                 220

Pro Leu Tyr Thr Gly Ala Ile Ser Thr Asn Glu
225                 230                 235

<210> SEQ ID NO 9
<211> LENGTH: 771
<212> TYPE: DNA
<213> ORGANISM: Artificial sequence
<220> FEATURE:
<223> OTHER INFORMATION: Coding sequence for full length enzyme having
      cellulolytic enhancing activity

<400> SEQUENCE: 9
atgctctcct ccgccctggc tcttgccggt gtcctccttt cttctgctcc cttcgtatct      60
gctcacggat tcgtcagcgg tatcgtcatc ggtgacaagt tctactctgg ctacattgtt     120
gacgagttcc cctacatgag cgaccctcct cccgtcattg ctgggccac cactgccacc      180 gaccttggat tcgttgacgg caccgaatac gccgagcccg atatcatctg ccaccgcaac     240
gccactcccg ccctcttgac tgctcctgtt gctgctggtg gtgatgttga gctccagtgg     300
actccctggc ccagctccca ccacggcccc gtcatcacct accttgctcc ttgcaacggc     360
aactgctcgg aagtcgacaa gaccacctc aagttcttca agatcgatga gggcggtctg      420
gtcaacgaca ccgatgttcc tggtacctgg gcctccgacg aattgattgc caacaacaac     480
agctggactg tcaagatccc cacctcgatt gagcctggtg gctacgtgct ccgtcacgag     540
atcattgctc tgcactccgc cgagaacctg gatggtgctc agaactaccc ccagtgcatc     600
aacatcaagg tcacccagac ctccggcacc gtcacccct ccggtaccct cggaactgct      660
ctctacaccg acactgctcc cggtatcctg atcgacatct acgagcccat tgccacctac     720 accatcccg gtcctcctct gtacactggt gccatctcca ccaacgagta a               771

<210> SEQ ID NO 10
<211> LENGTH: 256
<212> TYPE: PRT
<213> ORGANISM: Artificial sequence
<220> FEATURE:
<223> OTHER INFORMATION: Full length sequence of enzyme having
      cellulolytic enhancing activity

<400> SEQUENCE: 10

Met Leu Ser Ser Ala Leu Ala Leu Ala Gly Val Leu Leu Ser Ser Ala
1               5                   10                  15

Pro Phe Val Ser Ala His Gly Phe Val Gln Gly Ile Val Val Gly Asp
            20                  25                  30

Lys Phe Tyr Ser Gly Tyr Ile Val Asn Glu Phe Pro Tyr Glu Ser Asp
        35                  40                  45

Pro Pro Pro Val Ile Gly Trp Ala Thr Thr Ala Thr Asp Leu Gly Phe
    50                  55                  60
```

```
Val Asp Gly Ser Glu Tyr Ala Glu Pro Asp Ile Ile Cys His Arg Asp
 65                  70                  75                  80

Ala Thr Pro Ala Leu Leu Thr Ala Pro Val Ala Ala Gly Gly Thr Val
                 85                  90                  95

Glu Leu Gln Trp Thr Pro Trp Pro Ser Ser His His Gly Pro Val Ile
            100                 105                 110

Thr Tyr Leu Ala Pro Cys Asn Gly Asn Cys Ser Glu Val Asp Lys Thr
        115                 120                 125

Gln Leu Glu Phe Phe Lys Ile Asp Gln Ser Gly Leu Val Asn Asp Ser
130                 135                 140

Asp Pro Pro Gly Thr Trp Ala Ser Asp Glu Leu Ile Ala Asn Asn Asn
145                 150                 155                 160

Ser Trp Thr Val Thr Ile Pro Thr Ser Ile Glu Pro Gly Gly Tyr Val
                165                 170                 175

Leu Arg His Glu Ile Ile Ala Leu His Ser Ala Glu Gln Leu Asp Gly
            180                 185                 190

Ala Gln Asn Tyr Pro Gln Cys Ile Asn Ile Glu Ile Thr Gln Thr Ser
        195                 200                 205

Gly Thr Val Thr Pro Ser Gly Thr Leu Gly Glu Ala Leu Tyr Thr Asn
210                 215                 220

Thr Ala Ala Gly Ile Ile Ile Asp Ile Tyr Glu Pro Ile Ala Thr Tyr
225                 230                 235                 240

Thr Ile Pro Gly Pro Pro Leu Tyr Thr Gly Ala Ile Ser Thr Asn Glu
                245                 250                 255

<210> SEQ ID NO 11
<211> LENGTH: 235
<212> TYPE: PRT
<213> ORGANISM: Artificial sequence
<220> FEATURE:
<223> OTHER INFORMATION: Mature sequence of enzyme having cellulolytic
      enhancing activity

<400> SEQUENCE: 11

His Gly Phe Val Gln Gly Ile Val Val Gly Asp Lys Phe Tyr Ser Gly
 1               5                  10                  15

Tyr Ile Val Asn Glu Phe Pro Tyr Glu Ser Asp Pro Pro Val Ile
                 20                  25                  30

Gly Trp Ala Thr Thr Ala Thr Asp Leu Gly Phe Val Asp Gly Ser Glu
            35                  40                  45

Tyr Ala Glu Pro Asp Ile Ile Cys His Arg Asp Ala Thr Pro Ala Leu
        50                  55                  60

Leu Thr Ala Pro Val Ala Ala Gly Gly Thr Val Glu Leu Gln Trp Thr
 65                  70                  75                  80

Pro Trp Pro Ser Ser His His Gly Pro Val Ile Thr Tyr Leu Ala Pro
                 85                  90                  95

Cys Asn Gly Asn Cys Ser Glu Val Asp Lys Thr Gln Leu Glu Phe Phe
            100                 105                 110

Lys Ile Asp Gln Ser Gly Leu Val Asn Asp Ser Asp Pro Pro Gly Thr
        115                 120                 125

Trp Ala Ser Asp Glu Leu Ile Ala Asn Asn Ser Trp Thr Val Thr
130                 135                 140

Ile Pro Thr Ser Ile Glu Pro Gly Gly Tyr Val Leu Arg His Glu Ile
145                 150                 155                 160

Ile Ala Leu His Ser Ala Glu Gln Leu Asp Gly Ala Gln Asn Tyr Pro
                165                 170                 175
```

Gln Cys Ile Asn Ile Glu Ile Thr Gln Thr Ser Gly Thr Val Thr Pro
                180                 185                 190

Ser Gly Thr Leu Gly Glu Ala Leu Tyr Thr Asn Thr Ala Ala Gly Ile
        195                 200                 205

Ile Ile Asp Ile Tyr Glu Pro Ile Ala Thr Tyr Thr Ile Pro Gly Pro
210                 215                 220

Pro Leu Tyr Thr Gly Ala Ile Ser Thr Asn Glu
225                 230                 235

<210> SEQ ID NO 12
<211> LENGTH: 771
<212> TYPE: DNA
<213> ORGANISM: Artificial sequence
<220> FEATURE:
<223> OTHER INFORMATION: Coding sequence for full length enzyme having
      cellulolytic enhancing activity

<400> SEQUENCE: 12
atgctttctt ctgctcttgc ccttgctggt gttctcctct cctccgctcc cttcgtatct      60
gctcacggat tcgtccaggg tatcgttgtt ggtgacaagt tctactctgg ctacatcgtc     120
aacgagttcc cctacgagtc cgaccctcct cccgtcattg ctgggccac cactgccacc      180 gacctgggat tcgtcgatgg cagcgaatac gccgagcctg acatcatctg ccaccgtgat     240 gccaccccg ccctcttgac tgctcccgtc gctgctggtg gtaccgttga gctccagtgg      300
actccctggc cagctctca ccacggcccc gtcatcacct accttgctcc ttgcaacggc      360
aactgctcgg aggttgacaa gacccagctg gagttcttca gatcgacca gtccggtctg      420 gtcaacgact cggatcctcc cggtacctgg gcctccgacg aattgattgc aacaacaac     480 agctggactg tcaccattcc cacctccatt gagcctggtg gatacgtgct ccgccacgaa     540
atcattgccc tgcactccgc cgagcagctc gatggtgctc agaactaccc ccagtgcatc     600
aacatcgaga tcacccagac ctccggcacc gtcacccca gcggcaccct gggcgaggct     660
ctctacacca acactgctgc tggtatcatc atcgacatct acgagcccat tgccacctac     720
accatccccg gtcctcctct gtacactggt gccatctcca ctaatgagta a              771

<210> SEQ ID NO 13
<211> LENGTH: 254
<212> TYPE: PRT
<213> ORGANISM: Artificial sequence
<220> FEATURE:
<223> OTHER INFORMATION: Full length sequence of enzyme having
      cellulolytic enhancing activity

<400> SEQUENCE: 13

Met Leu Ser Ser Lys Ala Pro Val Thr Leu Ala Phe Ala Gly Leu Ala
1               5                   10                  15

Gly Leu Leu Ser Ala Pro Leu Val Lys Ala His Gly Phe Val Ser Gly
            20                  25                  30

Ile Val Val Gly Asp Glu Phe Tyr Ser Gly Tyr Ile Val Asn Glu Phe
        35                  40                  45

Pro Tyr Gln Ser Asn Pro Pro Val Ile Gly Trp Ala Thr Thr Ala
    50                  55                  60

Thr Asp Leu Gly Phe Val Asp Gly Thr Glu Tyr Gln Asp Pro Asp Ile
65                  70                  75                  80

Ile Cys His Arg Asn Ala Thr Pro Ala Leu Ile Thr Ala Glu Val Lys
                85                  90                  95

```
Ala Gly Gly Thr Val Glu Leu Gln Trp Thr Pro Trp Pro Ser Ser His
                100                 105                 110

His Gly Pro Val Ile Thr Tyr Leu Ala Asn Cys Asn Gly Asn Cys Ser
            115                 120                 125

Thr Val Asp Lys Thr Gln Leu Glu Phe Phe Lys Ile Asp Gln Ser Gly
        130                 135                 140

Leu Val Asn Asp Ser Asp Pro Pro Gly Thr Trp Ala Ser Asp Asn Leu
145                 150                 155                 160

Ile Ser Asn Asn Asn Ser Trp Thr Val Thr Ile Pro Ser Thr Leu Glu
                165                 170                 175

Pro Gly Gly Tyr Val Leu Arg His Glu Ile Ile Ala Leu His Ser Ala
            180                 185                 190

Gly Gln Leu Asn Gly Ala Gln Asn Tyr Pro Gln Cys Ile Asn Ile Lys
        195                 200                 205

Ile Thr Gln Gly Gly Ser Val Glu Pro Thr Gly Ala Leu Gly Glu Asp
    210                 215                 220

Leu Tyr His Asn Thr Asp Pro Gly Ile Leu Ile Asp Ile Tyr Glu Pro
225                 230                 235                 240

Ile Ala Thr Tyr Thr Ile Pro Gly Pro Ala Glu Pro Thr Phe
                245                 250
```

<210> SEQ ID NO 14
<211> LENGTH: 228
<212> TYPE: PRT
<213> ORGANISM: Artificial sequence
<220> FEATURE:
<223> OTHER INFORMATION: Mature sequence of enzyme having cellulolytic
      enhancing activity

<400> SEQUENCE: 14

```
His Gly Phe Val Ser Gly Ile Val Val Gly Asp Glu Phe Tyr Ser Gly
1               5                   10                  15

Tyr Ile Val Asn Glu Phe Pro Tyr Gln Ser Asn Pro Pro Val Ile
            20                  25                  30

Gly Trp Ala Thr Thr Ala Thr Asp Leu Gly Phe Val Asp Gly Thr Glu
        35                  40                  45

Tyr Gln Asp Pro Asp Ile Ile Cys His Arg Asn Ala Thr Pro Ala Leu
    50                  55                  60

Ile Thr Ala Glu Val Lys Ala Gly Gly Thr Val Glu Leu Gln Trp Thr
65                  70                  75                  80

Pro Trp Pro Ser Ser His His Gly Pro Val Ile Thr Tyr Leu Ala Asn
                85                  90                  95

Cys Asn Gly Asn Cys Ser Thr Val Asp Lys Thr Gln Leu Glu Phe Phe
                100                 105                 110

Lys Ile Asp Gln Ser Gly Leu Val Asn Asp Ser Asp Pro Pro Gly Thr
            115                 120                 125

Trp Ala Ser Asp Asn Leu Ile Ser Asn Asn Asn Ser Trp Thr Val Thr
        130                 135                 140

Ile Pro Ser Thr Leu Glu Pro Gly Gly Tyr Val Leu Arg His Glu Ile
145                 150                 155                 160

Ile Ala Leu His Ser Ala Gly Gln Leu Asn Gly Ala Gln Asn Tyr Pro
                165                 170                 175

Gln Cys Ile Asn Ile Lys Ile Thr Gln Gly Gly Ser Val Glu Pro Thr
            180                 185                 190

Gly Ala Leu Gly Glu Asp Leu Tyr His Asn Thr Asp Pro Gly Ile Leu
        195                 200                 205
```

Ile Asp Ile Tyr Glu Pro Ile Ala Thr Tyr Thr Ile Pro Gly Pro Ala
    210                 215                 220

Glu Pro Thr Phe
225

<210> SEQ ID NO 15
<211> LENGTH: 765
<212> TYPE: DNA
<213> ORGANISM: Artificial sequence
<220> FEATURE:
<223> OTHER INFORMATION: Coding sequence for full length enzyme having
      cellulolytic enhancing activity

<400> SEQUENCE: 15

```
atgctttctt ccaaggctcc cgtgacccta gcgttcgctg gtctggctgg tcttctgtct    60
gctcctctcg tcaaggccca cggattcgtc agcggtatcg ttgttggtga tgagttctac   120
tctggctaca tcgtcaacga gttcccctac cagtccaacc ctcctcctgt cattggctgg   180
gccaccactg ccaccgacct tggattcgtc gatggcaccg aataccagga ccccgatatc   240
atctgccacc gtaacgccac tcctgctctg atcaccgctg aggtcaaggc cggtggtact   300
gttgagctcc agtggactcc ctggcccagc agccaccacg gccccgtcat cacctacctg   360
gccaactgca acggcaactg ctcgaccgtt gacaagaccc agctcgagtt cttcaagatc   420
gaccagtccg gtctggtcaa cgactccgac cctcctggta cctgggcctc cgacaacctg   480
atctccaaca caacagctg  gactgtcacc atcccctcca ccctcgagcc cggtggctac   540
gtgctccgcc acgaaatcat tgccctccac tctgccggcc agctcaacgg tgcccagaac   600 taccccagt  gcatcaacat caagatcacc cagggtggct ccgttgagcc cactggtgct   660
cttggagaag acctctacca caacaccgac cccggtatct tgattgatat ctacgagccc   720
attgccacct acaccattcc cggccctgct gagcccacct tctaa             765
```

<210> SEQ ID NO 16
<211> LENGTH: 254
<212> TYPE: PRT
<213> ORGANISM: Artificial sequence
<220> FEATURE:
<223> OTHER INFORMATION: Full length sequence of enzyme having
      cellulolytic enhancing activity

<400> SEQUENCE: 16

Met Leu Ser Ser Lys Ala Pro Val Thr Leu Ala Phe Ala Gly Leu Ala
1               5                   10                  15

Gly Leu Leu Ser Ala Pro Leu Val Lys Ala His Gly Phe Val Gln Gly
            20                  25                  30

Ile Val Ile Asp Gly Thr Phe Tyr Ser Gly Tyr Ile Val Asp Glu Phe
        35                  40                  45

Pro Tyr Met Ser Asn Pro Pro Val Ile Gly Trp Ser Thr Thr Ala
    50                  55                  60

Thr Asp Leu Gly Phe Val Asp Gly Thr Glu Tyr Gln Glu Pro Asp Ile
65                  70                  75                  80

Ile Cys His Arg Asn Ala Thr Pro Ala Leu Leu Thr Ala Glu Val Lys
                85                  90                  95

Ala Gly Gly Thr Val Glu Leu Gln Trp Thr Pro Trp Pro Ser Ser His
            100                 105                 110

His Gly Pro Val Ile Thr Tyr Leu Ala Asn Cys Gly Gly Asn Cys Ser
        115                 120                 125

```
Asp Val Asp Lys Thr Gln Leu Glu Phe Phe Lys Ile Glu Gln Ser Gly
    130                 135                 140

Leu Ile Asn Asp Ser Asp Pro Pro Gly Thr Trp Ala Thr Asp Asn Leu
145                 150                 155                 160

Ile Ser Asn Asn Ser Trp Thr Val Thr Ile Pro Ser Thr Leu Glu
                165                 170                 175

Pro Gly Asn Tyr Val Leu Arg His Glu Ile Ile Ala Leu His Ser Ala
                180                 185                 190

Gly Asn Lys Asp Gly Ala Gln Asn Tyr Pro Gln Cys Ile Asn Ile Gln
            195                 200                 205

Val Thr Gly Gly Gly Ser Val Glu Pro Thr Gly Thr Lys Gly Glu Ala
    210                 215                 220

Leu Tyr Thr Asp Thr Asp Pro Gly Ile Leu Ile Asp Ile Tyr Glu Thr
225                 230                 235                 240

Ile Ala Thr Tyr Asp Ile Pro Gly Pro Pro Glu Pro Thr Phe
                245                 250

<210> SEQ ID NO 17
<211> LENGTH: 228
<212> TYPE: PRT
<213> ORGANISM: Artificial sequence
<220> FEATURE:
<223> OTHER INFORMATION: Mature sequence of enzyme having cellulolytic
      enhancing activity

<400> SEQUENCE: 17

His Gly Phe Val Gln Gly Ile Val Ile Asp Gly Thr Phe Tyr Ser Gly
1               5                   10                  15

Tyr Ile Val Asp Glu Phe Pro Tyr Met Ser Asn Pro Pro Val Ile
            20                  25                  30

Gly Trp Ser Thr Thr Ala Thr Asp Leu Gly Phe Val Asp Gly Thr Glu
        35                  40                  45

Tyr Gln Glu Pro Asp Ile Ile Cys His Arg Asn Ala Thr Pro Ala Leu
    50                  55                  60

Leu Thr Ala Glu Val Lys Ala Gly Gly Thr Val Glu Leu Gln Trp Thr
65                  70                  75                  80

Pro Trp Pro Ser Ser His His Gly Pro Val Ile Thr Tyr Leu Ala Asn
                85                  90                  95

Cys Gly Gly Asn Cys Ser Asp Val Asp Lys Thr Gln Leu Glu Phe Phe
                100                 105                 110

Lys Ile Glu Gln Ser Gly Leu Ile Asn Asp Ser Asp Pro Pro Gly Thr
            115                 120                 125

Trp Ala Thr Asp Asn Leu Ile Ser Asn Asn Ser Trp Thr Val Thr
    130                 135                 140

Ile Pro Ser Thr Leu Glu Pro Gly Asn Tyr Val Leu Arg His Glu Ile
145                 150                 155                 160

Ile Ala Leu His Ser Ala Gly Asn Lys Asp Gly Ala Gln Asn Tyr Pro
                165                 170                 175

Gln Cys Ile Asn Ile Gln Val Thr Gly Gly Gly Ser Val Glu Pro Thr
            180                 185                 190

Gly Thr Lys Gly Glu Ala Leu Tyr Thr Asp Thr Asp Pro Gly Ile Leu
        195                 200                 205

Ile Asp Ile Tyr Glu Thr Ile Ala Thr Tyr Asp Ile Pro Gly Pro Pro
    210                 215                 220

Glu Pro Thr Phe
225
```

<210> SEQ ID NO 18
<211> LENGTH: 765
<212> TYPE: DNA
<213> ORGANISM: Artificial sequence
<220> FEATURE:
<223> OTHER INFORMATION: Coding sequence for full length enzyme having cellulolytic enhancing activity

<400> SEQUENCE: 18

```
atgctctcct ccaaggctcc tgtgaccctc gccttcgctg gtcttgctgg tctgctctct      60
gctcctctgg tcaaggccca cggattcgtc cagggtatcg tcatcgatgg caccttctac    120
tctggctaca ttgttgatga gttcccctac atgagcaacc ctcctcctgt cattggctgg    180
tccaccactg ccaccgacct tggattcgtc gacggcaccg aataccagga gcccgatatc    240
atctgccacc gcaacgccac tcccgccctc ttgactgcgg aagtcaaggc cggtggtacc    300
gttgagctgc agtggactcc ctggcccagc tctcaccacg ccccgtcat cacctacctt      360
gccaactgcg gtggaaactg ctcggatgtt gacaagaccc agctcgagtt cttcaagatc    420
gagcagtccg gtctgatcaa cgactccgac cctcctggta cctgggccac cgacaacctg    480
atctccaaca caacagctg gactgtcacc atccctcca ccctcgagcc cggcaactac       540
gtgctccgtc acgagatcat tgccctccac tctgctggca caaggatgg tgctcagaac     600
taccccagt gcatcaacat ccaggtcacc ggtggtggca cgttgagcc cactggtacc       660
aagggcgagg ctctgtacac cgacaccgac cccggtatct tgattgacat ctacgaaacc    720
attgccacct acgacatccc cggtcctccc gagcccactt tctaa                     765
```

<210> SEQ ID NO 19
<211> LENGTH: 254
<212> TYPE: PRT
<213> ORGANISM: Artificial sequence
<220> FEATURE:
<223> OTHER INFORMATION: Full length sequence of enzyme having cellulolytic enhancing activity

<400> SEQUENCE: 19

```
Met Leu Ser Ser Lys Ala Pro Val Thr Leu Ala Phe Ala Gly Leu Ala
1               5                   10                  15

Gly Leu Leu Ser Ala Pro Leu Val Lys Ala His Gly Phe Val Gln Gly
            20                  25                  30

Ile Val Val Asp Gly Thr Phe Tyr Ser Gly Tyr Ile Val Asn Glu Tyr
        35                  40                  45

Pro Tyr Glu Ser Asn Pro Pro Val Ile Gly Trp Ala Thr Thr Ala
    50                  55                  60

Thr Asp Leu Gly Phe Val Asp Gly Ser Glu Tyr Gln Gly Pro Asp Ile
65                  70                  75                  80

Ile Cys His Arg Asn Gly Thr Pro Ala Leu Leu Thr Ala Pro Val Ala
                85                  90                  95

Ala Gly Gly Asp Val Glu Leu Gln Trp Thr Pro Trp Pro Ser Ser His
            100                 105                 110

His Gly Pro Val Ile Thr Tyr Leu Ala Asn Cys Asn Gly Asp Cys Ala
        115                 120                 125

Thr Val Asp Lys Thr Gln Leu Glu Phe Phe Lys Ile Asp Gln Ser Gly
    130                 135                 140

Leu Ile Asn Gly Ser Asp Pro Pro Gly Thr Trp Ala Ser Asp Asn Leu
145                 150                 155                 160
```

```
Ile Ala Asn Asn Asn Thr Trp Thr Val Lys Ile Pro Ala Thr Leu Glu
                165                 170                 175

Pro Gly Asn Tyr Val Leu Arg His Glu Ile Ile Ala Leu His Ser Ala
            180                 185                 190

Glu Asn Leu Asp Gly Ala Gln Asn Tyr Pro Gln Cys Ile Asn Ile Glu
        195                 200                 205

Val Thr Gly Gly Gly Ser Val Glu Pro Thr Gly Val Lys Gly Glu Ala
    210                 215                 220

Leu Tyr His Asn Thr Asp Pro Gly Ile Leu Ile Ser Ile Tyr Glu Pro
225                 230                 235                 240

Ile Ala Thr Tyr Thr Ile Pro Gly Pro Pro Glu Pro Thr Phe
                245                 250
```

<210> SEQ ID NO 20
<211> LENGTH: 228
<212> TYPE: PRT
<213> ORGANISM: Artificial sequence
<220> FEATURE:
<223> OTHER INFORMATION: Mature sequence of enzyme having cellulolytic
      enhancing activity

<400> SEQUENCE: 20

```
His Gly Phe Val Gln Gly Ile Val Val Asp Gly Thr Phe Tyr Ser Gly
1               5                   10                  15

Tyr Ile Val Asn Glu Tyr Pro Tyr Glu Ser Asn Pro Pro Val Ile
            20                  25                  30

Gly Trp Ala Thr Thr Ala Thr Asp Leu Gly Phe Val Asp Gly Ser Glu
            35                  40                  45

Tyr Gln Gly Pro Asp Ile Ile Cys His Arg Asn Gly Thr Pro Ala Leu
        50                  55                  60

Leu Thr Ala Pro Val Ala Ala Gly Gly Asp Val Glu Leu Gln Trp Thr
65                  70                  75                  80

Pro Trp Pro Ser Ser His His Gly Pro Val Ile Thr Tyr Leu Ala Asn
                85                  90                  95

Cys Asn Gly Asp Cys Ala Thr Val Asp Lys Thr Gln Leu Glu Phe Phe
            100                 105                 110

Lys Ile Asp Gln Ser Gly Leu Ile Asn Gly Ser Asp Pro Pro Gly Thr
            115                 120                 125

Trp Ala Ser Asp Asn Leu Ile Ala Asn Asn Thr Trp Thr Val Lys
        130                 135                 140

Ile Pro Ala Thr Leu Glu Pro Gly Asn Tyr Val Leu Arg His Glu Ile
145                 150                 155                 160

Ile Ala Leu His Ser Ala Glu Asn Leu Asp Gly Ala Gln Asn Tyr Pro
                165                 170                 175

Gln Cys Ile Asn Ile Glu Val Thr Gly Gly Gly Ser Val Glu Pro Thr
            180                 185                 190

Gly Val Lys Gly Glu Ala Leu Tyr His Asn Thr Asp Pro Gly Ile Leu
        195                 200                 205

Ile Ser Ile Tyr Glu Pro Ile Ala Thr Tyr Thr Ile Pro Gly Pro Pro
    210                 215                 220

Glu Pro Thr Phe
225
```

<210> SEQ ID NO 21
<211> LENGTH: 765
<212> TYPE: DNA
<213> ORGANISM: Artificial sequence
<220> FEATURE:
<223> OTHER INFORMATION: Coding sequence for full length enzyme having
    cellulolytic enhancing activity

<400> SEQUENCE: 21

```
atgctctcct ccaaggcccc cgtgaccctg gctttcgctg gtcttgctgg tcttctcagc      60
gctcctctgg tcaaggccca cggattcgtc cagggtatcg tcgttgatgg caccttctac     120
tctggctaca tcgtcaacga ataccctac gagtccaacc ctcctcccgt cattggctgg      180
gccaccactg ccaccgacct tggattcgtc gatggcagcg aataccaggg tcctgacatc     240
atctgccacc gtaacggcac ccccgcccct ctgaccgctc ccgttgctgc tgtggtggat     300
gttgagctcc agtggactcc ctggcccagc tctcaccacg gacctgtcat cacctacctg     360
gccaactgca acggtgactg cgctactgtt gacaagaccc agctcgagtt cttcaagatc     420
gaccagtccg gcttgatcaa cggctccgac cctcctggta cctgggcctc cgacaacctg     480
attgccaaca caacacctg gactgtcaag atcccgcca ccctcgagcc cggcaactac       540
gtgctccgcc acgaaatcat tgccctccac tctgctgaga cttggatgg tgcccagaac      600
taccccagt gcatcaacat tgaggtcacc ggtggtggct ccgttgagcc cactggtgtc      660
aagggcgagg ctctctacca aacaccgac cccggtatcc tgatctccat ctacgagccc      720
attgccacct acaccatccc cggtcctccc gagcccactt tctaa                     765
```

<210> SEQ ID NO 22
<211> LENGTH: 254
<212> TYPE: PRT
<213> ORGANISM: Artificial sequence
<220> FEATURE:
<223> OTHER INFORMATION: Full length sequence of enzyme having
    cellulolytic enhancing activity

<400> SEQUENCE: 22

```
Met Leu Ser Ser Lys Ala Pro Val Thr Leu Ala Phe Ala Gly Leu Ala
1               5                   10                  15

Gly Leu Leu Ser Ala Pro Leu Val Lys Ala His Gly Phe Val Ser Gly
            20                  25                  30

Ile Val Val Gly Asp Gln Phe Tyr Ser Gly Tyr Ile Val Asn Glu Tyr
        35                  40                  45

Pro Tyr Gln Ser Asp Pro Pro Val Ile Gly Trp Ala Thr Thr Ala
    50                  55                  60

Thr Asp Leu Gly Phe Val Asp Gly Ser Glu Tyr Gln Asp Pro Asp Ile
65                  70                  75                  80

Ile Cys His Arg Asn Ala Thr Pro Ala Leu Thr Ala Pro Val Ala
                85                  90                  95

Ala Gly Gly Asp Val Glu Leu Gln Trp Thr Pro Trp Pro Ser Ser His
            100                 105                 110

His Gly Pro Val Ile Thr Tyr Leu Ala Asn Cys Asn Gly Asn Cys Ser
        115                 120                 125

Glu Val Asp Lys Thr Gln Leu Asn Phe Phe Lys Ile Asp Gln Ser Gly
    130                 135                 140

Leu Ile Asn Gly Ser Asp Pro Pro Gly Thr Trp Ala Ser Asp Glu Leu
145                 150                 155                 160

Ile Ala Asn Asn Asn Thr Trp Thr Val Lys Ile Pro Thr Thr Leu Glu
                165                 170                 175

Pro Gly Asn Tyr Val Leu Arg His Glu Ile Ile Ala Leu His Ser Ala
            180                 185                 190
```

Gly Asn Lys Asp Gly Ala Gln Asn Tyr Pro Gln Cys Ile Asn Ile Lys
            195                 200                 205

Ile Thr Gln Gly Gly Thr Val Glu Pro Thr Gly Thr Leu Gly Glu Ala
        210                 215                 220

Leu Tyr His Asp Thr Asp Pro Gly Ile Ile Asp Ile Tyr Glu Pro
225                 230                 235                 240

Ile Ala Thr Tyr Asp Ile Pro Gly Pro Glu Tyr Asn Phe
                245                 250

<210> SEQ ID NO 23
<211> LENGTH: 228
<212> TYPE: PRT
<213> ORGANISM: Artificial sequence
<220> FEATURE:
<223> OTHER INFORMATION: Mature sequence of enzyme having cellulolytic
      enhancing activity

<400> SEQUENCE: 23

His Gly Phe Val Ser Gly Ile Val Val Gly Asp Gln Phe Tyr Ser Gly
1               5                   10                  15

Tyr Ile Val Asn Glu Tyr Pro Tyr Gln Ser Asp Pro Pro Val Ile
            20                  25                  30

Gly Trp Ala Thr Thr Ala Thr Asp Leu Gly Phe Val Asp Gly Ser Glu
        35                  40                  45

Tyr Gln Asp Pro Asp Ile Ile Cys His Arg Asn Ala Thr Pro Ala Leu
    50                  55                  60

Leu Thr Ala Pro Val Ala Ala Gly Gly Asp Val Glu Leu Gln Trp Thr
65                  70                  75                  80

Pro Trp Pro Ser Ser His His Gly Pro Val Ile Thr Tyr Leu Ala Asn
                85                  90                  95

Cys Asn Gly Asn Cys Ser Glu Val Asp Lys Thr Gln Leu Asn Phe Phe
            100                 105                 110

Lys Ile Asp Gln Ser Gly Leu Ile Asn Gly Ser Asp Pro Pro Gly Thr
        115                 120                 125

Trp Ala Ser Asp Glu Leu Ile Ala Asn Asn Asn Thr Trp Thr Val Lys
    130                 135                 140

Ile Pro Thr Thr Leu Glu Pro Gly Asn Tyr Val Leu Arg His Glu Ile
145                 150                 155                 160

Ile Ala Leu His Ser Ala Gly Asn Lys Asp Gly Ala Gln Asn Tyr Pro
                165                 170                 175

Gln Cys Ile Asn Ile Lys Ile Thr Gln Gly Gly Thr Val Glu Pro Thr
            180                 185                 190

Gly Thr Leu Gly Glu Ala Leu Tyr His Asp Thr Asp Pro Gly Ile Ile
        195                 200                 205

Ile Asp Ile Tyr Glu Pro Ile Ala Thr Tyr Asp Ile Pro Gly Pro Pro
    210                 215                 220

Glu Tyr Asn Phe
225

<210> SEQ ID NO 24
<211> LENGTH: 765
<212> TYPE: DNA
<213> ORGANISM: Artificial sequence
<220> FEATURE:
<223> OTHER INFORMATION: Coding sequence for full length enzyme having
      cellulolytic enhancing activity

<400> SEQUENCE: 24

```
atgctttctt ccaaggcccc cgtgaccta gcgttcgctg gtctggctgg tctgctctcc      60
gctcctctgg tcaaggccca cggattcgtc agcggtatcg tcgtcggtga ccagttctac    120
tctggctaca tcgtcaacga gtacccctac cagtcggatc ctcctcctgt cattggctgg    180
gccaccactg ccaccgacct tggattcgtc gatggcagcg aataccagga ccccgatatc    240
atctgccacc gtaacgccac ccccgccctc ttgactgctc ccgttgctgc tggtggtgat    300
gttgagctcc agtggactcc ctggccctcc tcccaccacg gccccgtcat cacctacctt    360
gccaactgca acggcaactg ctctgaggtt gacaagaccc agctcaactt cttcaagatc    420
gaccagtccg gtctgatcaa cggcagcgac cctcctggta cctgggcgtc ggatgagttg    480
attgccaaca caacacctg gactgtcaag atccccacca ccctcgagcc cggcaactac     540
gtgctccgcc acgagatcat tgctctgcac tccgccggta caaggatgg tgcccagaac     600
tacccccagt gcatcaacat caagatcacc cagggtggta ctgttgagcc cactggcacc    660
ctgggcgagg ctctctacca cgacaccgac cccggtatca tcattgacat ctacgagccc    720
attgccacct acgacatccc cggacctcct gaatacaact tttaa                    765
```

<210> SEQ ID NO 25
<211> LENGTH: 254
<212> TYPE: PRT
<213> ORGANISM: Artificial sequence
<220> FEATURE:
<223> OTHER INFORMATION: Full length sequence of enzyme having cellulolytic enhancing activity

<400> SEQUENCE: 25

```
Met Leu Ser Ser Lys Ala Pro Val Thr Leu Ala Phe Ala Gly Leu Ala
1               5                   10                  15

Gly Leu Leu Ser Ala Pro Leu Val Lys Ala His Gly Phe Val Ser Gly
            20                  25                  30

Ile Val Val Asp Gly Thr Phe Tyr Ser Gly Tyr Ile Val Asp Glu Tyr
        35                  40                  45

Pro Tyr Met Ser Asn Pro Pro Val Ile Gly Trp Ser Thr Thr Ala
    50                  55                  60

Thr Asp Leu Gly Phe Val Asp Gly Thr Glu Tyr Gln Glu Pro Asp Ile
65                  70                  75                  80

Ile Cys His Arg Asn Ala Thr Pro Ala Leu Leu Thr Ala Glu Val Lys
                85                  90                  95

Ala Gly Gly Thr Val Glu Leu Gln Trp Thr Pro Trp Pro Ser Ser His
            100                 105                 110

His Gly Pro Val Ile Thr Tyr Leu Ala Asn Cys Gly Asn Cys Ser
        115                 120                 125

Asp Val Asp Lys Thr Gln Leu Glu Phe Phe Lys Ile Glu Gln Ser Gly
    130                 135                 140

Leu Val Asn Asp Ser Asp Pro Pro Gly Thr Trp Ala Thr Asp Asn Leu
145                 150                 155                 160

Ile Ser Asn Asn Ser Trp Thr Val Thr Ile Pro Ser Thr Leu Glu
                165                 170                 175

Pro Gly Gly Tyr Val Leu Arg His Glu Ile Ile Ala Leu His Ser Ala
            180                 185                 190

Gly Gln Leu Asn Gly Ala Gln Asn Tyr Pro Gln Cys Ile Asn Ile Gln
        195                 200                 205

Ile Thr Gln Gly Gly Ser Val Glu Pro Thr Gly Ala Lys Gly Glu Ala
    210                 215                 220
```

```
Leu Tyr Thr Asn Thr Asp Pro Gly Ile Leu Ile Asp Ile Tyr Glu Thr
225                 230                 235                 240

Ile Ala Thr Tyr Asp Ile Pro Gly Pro Ala Glu Pro Thr Phe
                245                 250
```

<210> SEQ ID NO 26
<211> LENGTH: 228
<212> TYPE: PRT
<213> ORGANISM: Artificial sequence
<220> FEATURE:
<223> OTHER INFORMATION: Mature sequence of enzyme having cellulolytic
      enhancing activity

<400> SEQUENCE: 26

```
His Gly Phe Val Ser Gly Ile Val Val Asp Gly Thr Phe Tyr Ser Gly
1               5                   10                  15

Tyr Ile Val Asp Glu Tyr Pro Tyr Met Ser Asn Pro Pro Val Ile
                20                  25                  30

Gly Trp Ser Thr Thr Ala Thr Asp Leu Gly Phe Val Asp Gly Thr Glu
            35                  40                  45

Tyr Gln Glu Pro Asp Ile Ile Cys His Arg Asn Ala Thr Pro Ala Leu
50                  55                  60

Leu Thr Ala Glu Val Lys Ala Gly Gly Thr Val Glu Leu Gln Trp Thr
65                  70                  75                  80

Pro Trp Pro Ser Ser His His Gly Pro Val Ile Thr Tyr Leu Ala Asn
                85                  90                  95

Cys Gly Gly Asn Cys Ser Asp Val Asp Lys Thr Gln Leu Glu Phe Phe
            100                 105                 110

Lys Ile Glu Gln Ser Gly Leu Val Asn Asp Ser Asp Pro Pro Gly Thr
            115                 120                 125

Trp Ala Thr Asp Asn Leu Ile Ser Asn Asn Ser Trp Thr Val Thr
            130                 135                 140

Ile Pro Ser Thr Leu Glu Pro Gly Gly Tyr Val Leu Arg His Glu Ile
145                 150                 155                 160

Ile Ala Leu His Ser Ala Gly Gln Leu Asn Gly Ala Gln Asn Tyr Pro
                165                 170                 175

Gln Cys Ile Asn Ile Gln Ile Thr Gln Gly Gly Ser Val Glu Pro Thr
            180                 185                 190

Gly Ala Lys Gly Glu Ala Leu Tyr Thr Asn Thr Asp Pro Gly Ile Leu
            195                 200                 205

Ile Asp Ile Tyr Glu Thr Ile Ala Thr Tyr Asp Ile Pro Gly Pro Ala
210                 215                 220

Glu Pro Thr Phe
225
```

<210> SEQ ID NO 27
<211> LENGTH: 765
<212> TYPE: DNA
<213> ORGANISM: Artificial sequence
<220> FEATURE:
<223> OTHER INFORMATION: Coding sequence for full length enzyme having
      cellulolytic enhancing activity

<400> SEQUENCE: 27

```
atgctcagca gcaaggctcc cgtgacccta gcgttcgctg gtcttgctgg tcttctctct     60
gctcctctgg tcaaggccca cggattcgtc tctggcattg ttgttgacgg caccttctac    120
tctggctaca tcgtcgatga ataccsctac atgagcaacc ctcctcctgt cattggctgg    180
```

```
agcaccactg ccaccgacct tggattcgtc gatggcactg agtaccagga gcccgatatc    240
atctgccacc gcaacgccac ccccgccctc ttgactgctg aggtcaaggc cggtggtacc    300
gttgagctcc agtggactcc ctggccctcc tcccaccacg gccccgtcat cacctacctg    360
gccaactgcg gtggcaactg ctcggatgtt gacaagaccc agctcgagtt cttcaagatc    420
gagcagtccg gtctggtcaa cgactccgac cctcctggta cctgggccac cgacaacctg    480
atctccaaca caactcctg gactgtcacc atcccctcca ccctcgagcc cggtggatac    540
gtgctccgtc acgaaatcat tgccctgcac tctgctggcc agctcaacgg tgctcagaac    600 taccccccagt gcatcaacat ccagatcacc cagggtggct ccgttgagcc cactggtgcc    660
aagggcgagg ctctgtacac caacaccgac cccggtatct tgattgacat ctacgaaacc    720
attgccacct acgacatccc cggtcctgct gagcccactt tctaa                    765
```

<210> SEQ ID NO 28
<211> LENGTH: 254
<212> TYPE: PRT
<213> ORGANISM: Artificial sequence
<220> FEATURE:
<223> OTHER INFORMATION: Full length sequence of enzyme having
      cellulolytic enhancing activity <400> SEQUENCE: 28

```
Met Leu Ser Ser Lys Ala Pro Val Thr Leu Ala Phe Ala Gly Leu Ala
1               5                   10                  15

Gly Leu Leu Ser Ala Pro Leu Val Lys Ala His Gly Phe Val Ser Gly
            20                  25                  30

Ile Val Val Asp Gly Thr Phe Tyr Ser Gly Tyr Ile Val Asp Glu Phe
        35                  40                  45

Pro Tyr Met Ser Asn Pro Pro Val Ile Gly Trp Ser Thr Thr Ala
    50                  55                  60

Thr Asp Leu Gly Phe Val Asp Gly Thr Glu Tyr Gln Glu Pro Asp Ile
65                  70                  75                  80

Ile Cys His Arg Asn Ala Thr Pro Ala Leu Leu Thr Ala Glu Val Lys
                85                  90                  95

Ala Gly Gly Thr Val Glu Leu Gln Trp Thr Pro Trp Pro Ser Ser His
            100                 105                 110

His Gly Pro Val Ile Thr Tyr Leu Ala Asn Cys Gly Gly Asn Cys Ser
        115                 120                 125

Asp Val Asp Lys Thr Gln Leu Glu Phe Phe Lys Ile Glu Gln Ser Gly
    130                 135                 140

Leu Val Asn Asp Ser Asp Pro Pro Gly Thr Trp Ala Thr Asp Asn Leu
145                 150                 155                 160

Ile Ser Asn Asn Asn Thr Trp Thr Val Thr Ile Pro Ser Thr Leu Glu
                165                 170                 175

Pro Gly Gly Tyr Val Leu Arg His Glu Ile Ile Ala Leu His Ser Ala
            180                 185                 190

Gly Gln Leu Asn Gly Ala Gln Asn Tyr Pro Gln Cys Ile Asn Ile Gln
        195                 200                 205

Ile Thr Gln Gly Gly Ser Val Glu Pro Thr Gly Ala Lys Gly Glu Ala
    210                 215                 220

Leu Tyr Thr Asn Thr Asp Pro Gly Ile Leu Ile Asp Ile Tyr Glu Thr
225                 230                 235                 240

Ile Ala Thr Tyr Asp Ile Pro Gly Pro Ala Glu Pro Thr Phe
                245                 250
```

<210> SEQ ID NO 29
<211> LENGTH: 228
<212> TYPE: PRT
<213> ORGANISM: Artificial sequence
<220> FEATURE:
<223> OTHER INFORMATION: Mature sequence of enzyme having cellulolytic
      enhancing activity

<400> SEQUENCE: 29

His Gly Phe Val Ser Gly Ile Val Val Asp Gly Thr Phe Tyr Ser Gly
1               5                   10                  15

Tyr Ile Val Asp Glu Phe Pro Tyr Met Ser Asn Pro Pro Val Ile
            20                  25                  30

Gly Trp Ser Thr Thr Ala Thr Asp Leu Gly Phe Val Asp Gly Thr Glu
        35                  40                  45

Tyr Gln Glu Pro Asp Ile Ile Cys His Arg Asn Ala Thr Pro Ala Leu
    50                  55                  60

Leu Thr Ala Glu Val Lys Ala Gly Gly Thr Val Glu Leu Gln Trp Thr
65                  70                  75                  80

Pro Trp Pro Ser Ser His His Gly Pro Val Ile Thr Tyr Leu Ala Asn
                85                  90                  95

Cys Gly Gly Asn Cys Ser Asp Val Asp Lys Thr Gln Leu Glu Phe Phe
            100                 105                 110

Lys Ile Glu Gln Ser Gly Leu Val Asn Asp Ser Asp Pro Pro Gly Thr
        115                 120                 125

Trp Ala Thr Asp Asn Leu Ile Ser Asn Asn Thr Trp Thr Val Thr
    130                 135                 140

Ile Pro Ser Thr Leu Glu Pro Gly Gly Tyr Val Leu Arg His Glu Ile
145                 150                 155                 160

Ile Ala Leu His Ser Ala Gly Gln Leu Asn Gly Ala Gln Asn Tyr Pro
                165                 170                 175

Gln Cys Ile Asn Ile Gln Ile Thr Gln Gly Gly Ser Val Glu Pro Thr
            180                 185                 190

Gly Ala Lys Gly Glu Ala Leu Tyr Thr Asn Thr Asp Pro Gly Ile Leu
        195                 200                 205

Ile Asp Ile Tyr Glu Thr Ile Ala Thr Tyr Asp Ile Pro Gly Pro Ala
    210                 215                 220

Glu Pro Thr Phe
225

<210> SEQ ID NO 30
<211> LENGTH: 765
<212> TYPE: DNA
<213> ORGANISM: Artificial sequence
<220> FEATURE:
<223> OTHER INFORMATION: Coding sequence for full length enzyme having
      cellulolytic enhancing activity

<400> SEQUENCE: 30
atgctcagca gcaaggctcc cgtgaccctc gccttcgctg gtcttgctgg tcttctgtct     60
gctcctctgg tcaaggccca cggattcgtc tccggtatcg ttgttgacgg caccttctac    120
tctggctaca tcgtcgatga gttcccctac atgagcaacc ctcctcctgt cattggctgg    180
tccaccactg ccaccgacct tggattcgtc gatggcaccg aataccagga gcccgatatc    240
atctgccacc gtaacgccac ccccgccctg ttgactgcgg aagtcaaggc cggtggtacc    300
gttgagctcc agtggactcc ctggcccagc tctcaccacg gccccgtcat cacctacctt    360

-continued

```
gccaactgcg gtggcaactg ctcggatgtt gacaagaccc agctcgagtt cttcaagatt      420
gagcagtccg gtctggtcaa cgactccgac cctcctggta cctgggccac cgacaacctg      480
atctccaaca caacacctg gactgtcacc atcccctcca ccctcgagcc cggtggctac       540
gtgctccgcc acgaaatcat tgctctgcac tctgctggtc agctcaacgg tgctcagaac      600
tacccccagt gcatcaacat ccagatcacc cagggtggct ccgttgagcc cactggtgcc      660
aagggcgagg ctctctacac caacaccgac cccggtatct tgattgacat ctacgagact      720
attgccacct acgacatccc cggtcctgct gagcccactt tttaa                      765
```

<210> SEQ ID NO 31
<211> LENGTH: 254
<212> TYPE: PRT
<213> ORGANISM: Artificial sequence
<220> FEATURE:
<223> OTHER INFORMATION: Full length sequence of enzyme having
      cellulolytic enhancing activity

<400> SEQUENCE: 31

```
Met Leu Ser Ser Lys Ala Pro Val Thr Leu Ala Phe Ala Gly Leu Ala
1               5                   10                  15

Gly Leu Leu Ser Ala Pro Leu Val Lys Ala His Gly Phe Val Gln Gly
                20                  25                  30

Ile Val Val Asp Gly Thr Phe Tyr Ser Gly Tyr Ile Val Asp Glu Tyr
            35                  40                  45

Pro Tyr Met Ser Asn Pro Pro Val Ile Gly Trp Ser Thr Thr Ala
    50                  55                  60

Thr Asp Leu Gly Phe Val Asp Gly Ser Glu Tyr Gln Glu Pro Asp Ile
65                  70                  75                  80

Ile Cys His Arg Asn Ala Thr Pro Ala Leu Leu Thr Ala Glu Val Lys
                85                  90                  95

Ala Gly Gly Asp Val Glu Leu Gln Trp Thr Pro Trp Pro Ser Ser His
            100                 105                 110

His Gly Pro Val Ile Thr Tyr Leu Ala Asn Cys Gly Gly Asn Cys Ser
        115                 120                 125

Asp Val Asp Lys Thr Gln Leu Glu Phe Phe Lys Ile Glu Gln Ser Gly
    130                 135                 140

Leu Val Asn Asp Ser Asp Pro Pro Gly Thr Trp Ala Thr Asp Asn Leu
145                 150                 155                 160

Ile Ser Asn Asn Asn Thr Trp Thr Val Thr Ile Pro Ser Thr Leu Glu
                165                 170                 175

Pro Gly Gly Tyr Val Leu Arg His Glu Ile Ile Ala Leu His Ser Ala
            180                 185                 190

Gly Gln Leu Asn Gly Ala Gln Asn Tyr Pro Gln Cys Ile Asn Ile Gln
        195                 200                 205

Val Thr Gln Gly Gly Ser Val Glu Pro Thr Gly Ala Lys Gly Glu Ala
    210                 215                 220

Leu Tyr Thr Asn Thr Asp Pro Gly Ile Leu Ile Asp Ile Tyr Glu Thr
225                 230                 235                 240

Ile Ala Thr Tyr Asp Ile Pro Gly Pro Pro Glu Pro Thr Phe
                245                 250
```

<210> SEQ ID NO 32
<211> LENGTH: 228
<212> TYPE: PRT
<213> ORGANISM: Artificial sequence
<220> FEATURE:

<223> OTHER INFORMATION: Mature sequence of enzyme having cellulolytic
      enhancing activity

<400> SEQUENCE: 32

```
His Gly Phe Val Gln Gly Ile Val Val Asp Gly Thr Phe Tyr Ser Gly
1               5                   10                  15
Tyr Ile Val Asp Glu Tyr Pro Tyr Met Ser Asn Pro Pro Val Ile
            20                  25                  30
Gly Trp Ser Thr Thr Ala Thr Asp Leu Gly Phe Val Asp Gly Ser Glu
        35                  40                  45
Tyr Gln Glu Pro Asp Ile Ile Cys His Arg Asn Ala Thr Pro Ala Leu
    50                  55                  60
Leu Thr Ala Glu Val Lys Ala Gly Gly Asp Val Glu Leu Gln Trp Thr
65                  70                  75                  80
Pro Trp Pro Ser Ser His His Gly Pro Val Ile Thr Tyr Leu Ala Asn
                85                  90                  95
Cys Gly Gly Asn Cys Ser Asp Val Asp Lys Thr Gln Leu Glu Phe Phe
            100                 105                 110
Lys Ile Glu Gln Ser Gly Leu Val Asn Asp Ser Asp Pro Pro Gly Thr
        115                 120                 125
Trp Ala Thr Asp Asn Leu Ile Ser Asn Asn Asn Thr Trp Thr Val Thr
    130                 135                 140
Ile Pro Ser Thr Leu Glu Pro Gly Gly Tyr Val Leu Arg His Glu Ile
145                 150                 155                 160
Ile Ala Leu His Ser Ala Gly Gln Leu Asn Gly Ala Gln Asn Tyr Pro
                165                 170                 175
Gln Cys Ile Asn Ile Gln Val Thr Gln Gly Gly Ser Val Glu Pro Thr
            180                 185                 190
Gly Ala Lys Gly Glu Ala Leu Tyr Thr Asn Thr Asp Pro Gly Ile Leu
        195                 200                 205
Ile Asp Ile Tyr Glu Thr Ile Ala Thr Tyr Asp Ile Pro Gly Pro Pro
    210                 215                 220
Glu Pro Thr Phe
225
```

<210> SEQ ID NO 33
<211> LENGTH: 765
<212> TYPE: DNA
<213> ORGANISM: Artificial sequence
<220> FEATURE:
<223> OTHER INFORMATION: Coding sequence for full length enzyme having
      cellulolytic enhancing activity

<400> SEQUENCE: 33

```
atgctttctt ccaaggctcc tgtgaccctg gctttcgctg tcttgctgg tctgctctct       60
gctcctctgg tcaaggccca cggattcgtc cagggtatcg ttgttgatgg caccttctac     120
tctggctaca ttgtcgacga ataccctac atgagcaacc ctcctcctgt cattggctgg     180
tccaccactg ccaccgacct tggattcgtc gatggcagcg aataccagga gcccgatatc     240
atctgccacc gcaacgccac ccccgccctc ttgactgctg aggtcaaggc cggtggtgat     300
gttgagctcc agtggactcc ctggccctcc tccaccacg gacctgtcat cacctacctt     360
gccaactgcg gtggcaactg ctcggatgtt gacaagaccc agctcgagtt cttcaagatc     420
gagcagtccg gtctggtcaa cgactccgac cctcccggca cctgggccac cgacaacctg     480
atctccaaca caacaccctg gactgtcacc atccccagca ctctcgagcc cggtggatac     540
```

-continued

```
gtgctccgtc acgagatcat tgccctgcac tctgctggcc agctcaacgg tgctcagaac    600 taccccagt gcatcaacat ccaggtcacc cagggtggca gcgttgagcc cactggtgcc     660
aagggtgagg ctctctacac caacaccgac cccggtatct tgattgacat ctacgaaacc    720
attgccacct acgacatccc cggccctccc gagcccactt tctaa                    765
```

```
<210> SEQ ID NO 34
<211> LENGTH: 254
<212> TYPE: PRT
<213> ORGANISM: Artificial sequence
<220> FEATURE:
<223> OTHER INFORMATION: Full length sequence of enzyme having
      cellulolytic enhancing activity

<400> SEQUENCE: 34
```

Met Leu Ser Ser Lys Ala Pro Val Thr Leu Ala Phe Ala Gly Leu Ala
1               5                   10                  15

Gly Leu Leu Ser Ala Pro Leu Val Lys Ala His Gly Phe Val Ser Gly
            20                  25                  30

Ile Val Ile Asp Gly Thr Phe Tyr Ser Gly Tyr Ile Val Asp Glu Tyr
        35                  40                  45

Pro Tyr Met Ser Asn Pro Pro Val Ile Gly Trp Ser Thr Thr Ala
    50                  55                  60

Thr Asp Leu Gly Phe Val Asp Gly Thr Glu Tyr Gln Glu Pro Asp Ile
65                  70                  75                  80

Ile Cys His Arg Asn Gly Thr Pro Ala Leu Leu Thr Ala Glu Val Lys
                85                  90                  95

Ala Gly Gly Thr Val Glu Leu Gln Trp Thr Pro Trp Pro Ser Ser His
            100                 105                 110

His Gly Pro Val Ile Thr Tyr Leu Ala Asn Cys Gly Gly Asp Cys Ser
        115                 120                 125

Asp Val Asp Lys Thr Gln Leu Glu Phe Phe Lys Ile Glu Gln Ser Gly
    130                 135                 140

Leu Val Asn Asp Ser Asp Pro Pro Gly Thr Trp Ala Thr Asp Asn Leu
145                 150                 155                 160

Ile Ser Asn Asn Asn Thr Trp Thr Val Thr Ile Pro Ser Thr Leu Glu
                165                 170                 175

Pro Gly Asn Tyr Val Leu Arg His Glu Ile Ile Ala Leu His Ser Ala
            180                 185                 190

Gly Gln Leu Asn Gly Ala Gln Asn Tyr Pro Gln Cys Ile Asn Ile Gln
        195                 200                 205

Ile Thr Gly Gly Gly Ser Val Glu Pro Thr Gly Ala Lys Gly Glu Ala
    210                 215                 220

Leu Tyr Thr Asn Thr Asp Pro Gly Ile Leu Ile Asp Ile Tyr Glu Thr
225                 230                 235                 240

Ile Ala Thr Tyr Asp Ile Pro Gly Pro Ala Glu Pro Thr Phe
                245                 250

```
<210> SEQ ID NO 35
<211> LENGTH: 228
<212> TYPE: PRT
<213> ORGANISM: Artificial sequence
<220> FEATURE:
<223> OTHER INFORMATION: Mature sequence of enzyme having cellulolytic
      enhancing activity

<400> SEQUENCE: 35
```

His Gly Phe Val Ser Gly Ile Val Ile Asp Gly Thr Phe Tyr Ser Gly

```
  1               5                  10                 15
Tyr Ile Val Asp Glu Tyr Pro Tyr Met Ser Asn Pro Pro Val Ile
                20                 25                 30
Gly Trp Ser Thr Thr Ala Thr Asp Leu Gly Phe Val Asp Gly Thr Glu
                35                 40                 45
Tyr Gln Glu Pro Asp Ile Ile Cys His Arg Asn Gly Thr Pro Ala Leu
 50                 55                 60
Leu Thr Ala Glu Val Lys Ala Gly Gly Thr Val Glu Leu Gln Trp Thr
 65                 70                 75                 80
Pro Trp Pro Ser Ser His His Gly Pro Val Ile Thr Tyr Leu Ala Asn
                85                 90                 95
Cys Gly Gly Asp Cys Ser Asp Val Asp Lys Thr Gln Leu Glu Phe Phe
                100                105                110
Lys Ile Glu Gln Ser Gly Leu Val Asn Asp Ser Asp Pro Pro Gly Thr
                115                120                125
Trp Ala Thr Asp Asn Leu Ile Ser Asn Asn Thr Trp Thr Val Thr
 130                135                140
Ile Pro Ser Thr Leu Glu Pro Gly Asn Tyr Val Leu Arg His Glu Ile
 145                150                155                160
Ile Ala Leu His Ser Ala Gly Gln Leu Asn Gly Ala Gln Asn Tyr Pro
                165                170                175
Gln Cys Ile Asn Ile Gln Ile Thr Gly Gly Gly Ser Val Glu Pro Thr
                180                185                190
Gly Ala Lys Gly Glu Ala Leu Tyr Thr Asn Thr Asp Pro Gly Ile Leu
                195                200                205
Ile Asp Ile Tyr Glu Thr Ile Ala Thr Tyr Asp Ile Pro Gly Pro Ala
 210                215                220
Glu Pro Thr Phe
 225

<210> SEQ ID NO 36
<211> LENGTH: 765
<212> TYPE: DNA
<213> ORGANISM: Artificial sequence
<220> FEATURE:
<223> OTHER INFORMATION: Coding sequence for full length enzyme having
      cellulolytic enhancing activity

<400> SEQUENCE: 36
atgctttctt ccaaggcccc cgtgacccta gcgttcgctg gtctggctgg cttgctttct      60
gctcctctgg tcaaggccca cggattcgtc tccggtatcg tcattgatgg caccttctac     120
tctggctaca ttgttgatga ataccctac atgagcaacc ctcctcccgt cattggctgg     180
tccaccactg ccaccgacct ggattcgtc gatggcaccg aataccagga gcccgatatc     240
atctgccacc gcaacggcac tcccgccctc ctcactgctg aggtcaaggc cggtggtacc     300
gttgagctcc agtggactcc ctggcccagc tctcaccacg gccccgtcat cacctacctt     360
gccaactgcg gtggtgactg ctcggatgtt gacaagaccc agctggagtt cttcaagatc     420
gagcagtccg gtctggtcaa cgactccgac cctcctggta cctgggccac cgacaacctg     480
atctccaaca caacacctg gactgtcacc atccccagca ccctcgagcc cggcaactac     540
gtgctccgtc acgaaatcat tgctctccac tccgccggcc agctcaacgg tgctcagaac     600
taccccccag tgcatcaacat ccagatcacc ggtggtggaa gcgttgagcc cactggtgcc     660
aagggcgagg ctctctacac caacaccgac cccggtatcc tgatcgacat ctacgagact     720
```
attgccacct acgacatccc cggtcctgct gagcctacat tctaa                765

<210> SEQ ID NO 37
<211> LENGTH: 254
<212> TYPE: PRT
<213> ORGANISM: Artificial sequence
<220> FEATURE:
<223> OTHER INFORMATION: Full length sequence of enzyme having
      cellulolytic enhancing activity

<400> SEQUENCE: 37

```
Met Leu Ser Ser Lys Ala Pro Val Thr Leu Ala Phe Ala Gly Leu Ala
1               5                   10                  15

Gly Leu Leu Ser Ala Pro Leu Val Lys Ala His Gly Phe Val Ser Gly
            20                  25                  30

Ile Val Val Asp Gly Thr Phe Tyr Ser Gly Tyr Ile Val Asp Glu Phe
        35                  40                  45

Pro Tyr Met Ser Asn Pro Pro Val Ile Gly Trp Ser Thr Thr Ala
    50                  55                  60

Thr Asp Leu Gly Phe Val Asp Gly Ser Glu Tyr Gln Glu Pro Asp Ile
65                  70                  75                  80

Ile Cys His Arg Asn Ala Thr Pro Ala Leu Leu Thr Ala Glu Val Lys
                85                  90                  95

Ala Gly Gly Asp Val Glu Leu Gln Trp Thr Pro Trp Pro Ser Ser His
            100                 105                 110

His Gly Pro Val Ile Thr Tyr Leu Ala Asn Cys Gly Gly Asn Cys Ser
        115                 120                 125

Asp Val Asp Lys Thr Gln Leu Glu Phe Phe Lys Ile Glu Gln Ser Gly
    130                 135                 140

Leu Val Asn Gly Ser Asp Pro Pro Gly Thr Trp Ala Thr Asp Asn Leu
145                 150                 155                 160

Ile Ser Asn Asn Asn Ser Trp Thr Val Thr Ile Pro Ser Thr Leu Glu
                165                 170                 175

Pro Gly Gly Tyr Val Leu Arg His Glu Ile Ile Ala Leu His Ser Ala
            180                 185                 190

Gly Asn Lys Asp Gly Ala Gln Asn Tyr Pro Gln Cys Ile Asn Ile Gln
        195                 200                 205

Ile Thr Gln Gly Gly Thr Val Glu Pro Thr Gly Ala Lys Gly Glu Ala
    210                 215                 220

Leu Tyr Thr Asn Thr Asp Pro Gly Ile Leu Ile Asp Ile Tyr Glu Thr
225                 230                 235                 240

Ile Ala Thr Tyr Asp Ile Pro Gly Pro Ala Glu Pro Thr Phe
                245                 250
```

<210> SEQ ID NO 38
<211> LENGTH: 228
<212> TYPE: PRT
<213> ORGANISM: Artificial sequence
<220> FEATURE:
<223> OTHER INFORMATION: Mature sequence of enzyme having cellulolytic
      enhancing activity

<400> SEQUENCE: 38

```
His Gly Phe Val Ser Gly Ile Val Val Asp Gly Thr Phe Tyr Ser Gly
1               5                   10                  15

Tyr Ile Val Asp Glu Phe Pro Tyr Met Ser Asn Pro Pro Val Ile
            20                  25                  30

Gly Trp Ser Thr Thr Ala Thr Asp Leu Gly Phe Val Asp Gly Ser Glu
```

```
                35                  40                  45
Tyr Gln Glu Pro Asp Ile Ile Cys His Arg Asn Ala Thr Pro Ala Leu
 50                  55                  60

Leu Thr Ala Glu Val Lys Ala Gly Gly Asp Val Glu Leu Gln Trp Thr
 65                  70                  75                  80

Pro Trp Pro Ser Ser His His Gly Pro Val Ile Thr Tyr Leu Ala Asn
                 85                  90                  95

Cys Gly Gly Asn Cys Ser Asp Val Asp Lys Thr Gln Leu Glu Phe Phe
            100                 105                 110

Lys Ile Glu Gln Ser Gly Leu Val Asn Gly Ser Asp Pro Pro Gly Thr
        115                 120                 125

Trp Ala Thr Asp Asn Leu Ile Ser Asn Asn Asn Ser Trp Thr Val Thr
    130                 135                 140

Ile Pro Ser Thr Leu Glu Pro Gly Gly Tyr Val Leu Arg His Glu Ile
145                 150                 155                 160

Ile Ala Leu His Ser Ala Gly Asn Lys Asp Gly Ala Gln Asn Tyr Pro
                165                 170                 175

Gln Cys Ile Asn Ile Gln Ile Thr Gln Gly Gly Thr Val Glu Pro Thr
            180                 185                 190

Gly Ala Lys Gly Glu Ala Leu Tyr Thr Asn Thr Asp Pro Gly Ile Leu
        195                 200                 205

Ile Asp Ile Tyr Glu Thr Ile Ala Thr Tyr Asp Ile Pro Gly Pro Ala
    210                 215                 220

Glu Pro Thr Phe
225

<210> SEQ ID NO 39
<211> LENGTH: 765
<212> TYPE: DNA
<213> ORGANISM: Artificial sequence
<220> FEATURE:
<223> OTHER INFORMATION: Coding sequence for full length enzyme having
      cellulolytic enhancing activity

<400> SEQUENCE: 39
atgctttctt ccaaggctcc tgtgacccta gcgttcgctg gtctggctgg tcttctctct      60
gctcctctgg tcaaggccca cggattcgtc tccggcattg ttgttgacgg caccttctac     120
tctggctaca ttgtcgacga gttccoctac atgagcaacc ctcctcccgt cattggctgg     180
tccaccactg ccactgacct tggattcgtc gatggcagcg aataccagga gcccgatatc     240
atctgccacc gcaacgccac ccccgccctc ttgactgctg aggtcaaggc cggtggtgat     300
gttgagctcc agtggactcc ctggccctcc tccaccacg gacctgtcat cacctacctg      360
gccaactgcg gtggcaactg ctcggatgtt gacaagaccc agctcgagtt cttcaagatc     420
gagcagtccg gtctggtcaa cggctccgac cctcccggta cctgggccac gacaacctg      480 atctccaaca caacagctg gaccgtcacc atccccagca ctctcgagcc cggtggatac      540
gtgctccgtc acgaaatcat tgccctccac tctgctggca caaggatgg tgcccagaac      600 tacccccagt gcatcaacat ccagatcacc cagggtggta ccgttgagcc cactggtgcc     660
aagggcgagg ctctctacac caacaccgac cccggtatcc tgatcgacat ctacgaaacc     720
attgccacct acgacatccc cggtcctgct gagcccacgt tttaa                     765

<210> SEQ ID NO 40
<211> LENGTH: 254
<212> TYPE: PRT
```

<213> ORGANISM: Artificial sequence
<220> FEATURE:
<223> OTHER INFORMATION: Full length sequence of enzyme having cellulolytic enhancing activity

<400> SEQUENCE: 40

Met Leu Ser Ser Lys Ala Pro Val Thr Leu Ala Phe Ala Gly Leu Ala
1               5                   10                  15

Gly Leu Leu Ser Ala Pro Leu Val Lys Ala His Gly Phe Val Ser Gly
            20                  25                  30

Ile Val Ile Asp Gly Thr Phe Tyr Ser Gly Tyr Ile Val Asp Glu Tyr
        35                  40                  45

Pro Tyr Met Ser Asn Pro Pro Val Ile Gly Trp Ser Thr Thr Ala
    50                  55                  60

Thr Asp Leu Gly Phe Val Asp Gly Ser Glu Tyr Gln Glu Pro Asp Ile
65                  70                  75                  80

Ile Cys His Arg Asn Ala Thr Pro Ala Leu Leu Thr Ala Glu Val Lys
                85                  90                  95

Ala Gly Gly Asp Val Glu Leu Gln Trp Thr Pro Trp Pro Ser Ser His
            100                 105                 110

His Gly Pro Val Ile Thr Tyr Leu Ala Asn Cys Gly Asn Cys Ser
        115                 120                 125

Asp Val Asp Lys Thr Gln Leu Glu Phe Phe Lys Ile Glu Gln Ser Gly
130                 135                 140

Leu Val Asn Asp Ser Asp Pro Pro Gly Thr Trp Ala Thr Asp Asn Leu
145                 150                 155                 160

Ile Ser Asn Asn Asn Thr Trp Thr Val Thr Ile Pro Ser Thr Leu Glu
                165                 170                 175

Pro Gly Gly Tyr Val Leu Arg His Glu Ile Ile Ala Leu His Ser Ala
            180                 185                 190

Gly Gln Leu Asn Gly Ala Gln Asn Tyr Pro Gln Cys Ile Asn Ile Gln
        195                 200                 205

Ile Thr Gly Gly Gly Ser Val Glu Pro Thr Gly Ala Lys Gly Glu Ala
210                 215                 220

Leu Tyr Thr Asn Thr Asp Pro Gly Ile Leu Ile Asp Ile Tyr Glu Thr
225                 230                 235                 240

Ile Ala Thr Tyr Asp Ile Pro Gly Pro Pro Glu Pro Thr Phe
                245                 250

<210> SEQ ID NO 41
<211> LENGTH: 228
<212> TYPE: PRT
<213> ORGANISM: Artificial sequence
<220> FEATURE:
<223> OTHER INFORMATION: Mature sequence of enzyme having cellulolytic enhancing activity

<400> SEQUENCE: 41

His Gly Phe Val Ser Gly Ile Val Ile Asp Gly Thr Phe Tyr Ser Gly
1               5                   10                  15

Tyr Ile Val Asp Glu Tyr Pro Tyr Met Ser Asn Pro Pro Val Ile
            20                  25                  30

Gly Trp Ser Thr Thr Ala Thr Asp Leu Gly Phe Val Asp Gly Ser Glu
        35                  40                  45

Tyr Gln Glu Pro Asp Ile Ile Cys His Arg Asn Ala Thr Pro Ala Leu
    50                  55                  60

Leu Thr Ala Glu Val Lys Ala Gly Gly Asp Val Glu Leu Gln Trp Thr

```
              65                  70                  75                  80
Pro Trp Pro Ser Ser His His Gly Pro Val Ile Thr Tyr Leu Ala Asn
                    85                  90                  95

Cys Gly Gly Asn Cys Ser Asp Val Asp Lys Thr Gln Leu Glu Phe Phe
                    100                 105                 110

Lys Ile Glu Gln Ser Gly Leu Val Asn Asp Ser Asp Pro Pro Gly Thr
                    115                 120                 125

Trp Ala Thr Asp Asn Leu Ile Ser Asn Asn Thr Trp Thr Val Thr
  130                 135                 140

Ile Pro Ser Thr Leu Glu Pro Gly Tyr Val Leu Arg His Glu Ile
145                 150                 155                 160

Ile Ala Leu His Ser Ala Gly Gln Leu Asn Gly Ala Gln Asn Tyr Pro
                    165                 170                 175

Gln Cys Ile Asn Ile Gln Ile Thr Gly Gly Gly Ser Val Glu Pro Thr
                    180                 185                 190

Gly Ala Lys Gly Glu Ala Leu Tyr Thr Asn Thr Asp Pro Gly Ile Leu
                    195                 200                 205

Ile Asp Ile Tyr Glu Thr Ile Ala Thr Tyr Asp Ile Pro Gly Pro Pro
  210                 215                 220

Glu Pro Thr Phe
225

<210> SEQ ID NO 42
<211> LENGTH: 765
<212> TYPE: DNA
<213> ORGANISM: Artificial sequence
<220> FEATURE:
<223> OTHER INFORMATION: Coding sequence for full length enzyme having
      cellulolytic enhancing activity

<400> SEQUENCE: 42
atgctctcct ccaaggcccc cgtgaccctg gctttcgctg gtcttgccgg tctgctgtct    60
gctcctctgg tcaaggccca cggattcgtc tccggcattg tcatcgatgg caccttctac   120
tctggctaca cgtcgatga gtaccccctac atgagcaacc ctcctcccgt cattggctgg   180
tccaccactg ccaccgacct tggattcgtt gacggcagcg aataccagga gcctgacatc   240
atctgccacc gcaacgccac ccccgctctt ttgactgcgg aagtcaaggc cggtggtgat   300
gttgagctcc agtggactcc ctggccctcc tccaccacg gccccgtcat cacctacctt   360
gccaactgcg gtggcaactg ctcggatgtt gacaagaccc agctcgagtt cttcaagatc   420
gagcagtccg gtctggtcaa cgactcggat cctcccggca cctgggccac cgacaacctg   480
atctccaaca caacacctg gactgtcacc atccccagca ccctcgagcc tggtggatac   540
gtgctccgtc acgaaatcat tgctctccac tctgctggcc agctcaacgg tgctcagaac   600 taccccagt gcatcaacat ccagatcacc ggtggtggaa gcgttgagcc cactggtgcc   660
aagggtgagg ctctctacac caacaccgac cccggtatct tgattgacat ctacgagact   720
attgccacct acgacatccc cggtcctccc gagcctactt tctaa                   765

<210> SEQ ID NO 43
<211> LENGTH: 254
<212> TYPE: PRT
<213> ORGANISM: Artificial sequence
<220> FEATURE:
<223> OTHER INFORMATION: Full length sequence of enzyme having
      cellulolytic enhancing activity

<400> SEQUENCE: 43
```

```
Met Leu Ser Ser Lys Ala Pro Val Thr Leu Ala Phe Ala Gly Leu Ala
1               5                   10                  15

Gly Leu Leu Ser Ala Pro Leu Val Lys Ala His Gly Phe Val Gln Gly
            20                  25                  30

Ile Val Val Asp Gly Thr Phe Tyr Ser Gly Tyr Ile Val Asp Glu Phe
            35                  40                  45

Pro Tyr Met Ser Asn Pro Pro Val Ile Gly Trp Ser Thr Thr Ala
50                      55                  60

Thr Asp Leu Gly Phe Val Asp Gly Ser Glu Tyr Gln Glu Pro Asp Ile
65                  70                  75                  80

Ile Cys His Arg Asn Gly Thr Pro Ala Leu Leu Thr Ala Glu Val Lys
                85                  90                  95

Ala Gly Gly Thr Val Glu Leu Gln Trp Thr Pro Trp Pro Ser Ser His
            100                 105                 110

His Gly Pro Val Ile Thr Tyr Leu Ala Asn Cys Gly Gly Asp Cys Ser
            115                 120                 125

Asp Val Asp Lys Thr Gln Leu Glu Phe Phe Lys Ile Glu Gln Ser Gly
        130                 135                 140

Leu Val Asn Gly Ser Asp Pro Pro Gly Thr Trp Ala Thr Asp Asn Leu
145                 150                 155                 160

Ile Ser Asn Asn Asn Ser Trp Thr Val Thr Ile Pro Ser Thr Leu Glu
                165                 170                 175

Pro Gly Gly Tyr Val Leu Arg His Glu Ile Ile Ala Leu His Ser Ala
            180                 185                 190

Gly Gln Leu Asn Gly Ala Gln Asn Tyr Pro Gln Cys Ile Asn Ile Gln
        195                 200                 205

Ile Thr Gln Gly Gly Ser Val Glu Pro Thr Gly Thr Lys Gly Glu Ala
210                 215                 220

Leu Tyr Thr Asp Thr Asp Pro Gly Ile Leu Ile Asp Ile Tyr Glu Thr
225                 230                 235                 240

Ile Ala Thr Tyr Asp Ile Pro Gly Pro Ala Glu Pro Thr Phe
                245                 250
```

<210> SEQ ID NO 44
<211> LENGTH: 228
<212> TYPE: PRT
<213> ORGANISM: Artificial sequence
<220> FEATURE:
<223> OTHER INFORMATION: Mature sequence of enzyme having cellulolytic
      enhancing activity

<400> SEQUENCE: 44

```
His Gly Phe Val Gln Gly Ile Val Val Asp Gly Thr Phe Tyr Ser Gly
1               5                   10                  15

Tyr Ile Val Asp Glu Phe Pro Tyr Met Ser Asn Pro Pro Val Ile
            20                  25                  30

Gly Trp Ser Thr Thr Ala Thr Asp Leu Gly Phe Val Asp Gly Ser Glu
            35                  40                  45

Tyr Gln Glu Pro Asp Ile Ile Cys His Arg Asn Gly Thr Pro Ala Leu
50                  55                  60

Leu Thr Ala Glu Val Lys Ala Gly Gly Thr Val Glu Leu Gln Trp Thr
65                  70                  75                  80

Pro Trp Pro Ser Ser His His Gly Pro Val Ile Thr Tyr Leu Ala Asn
                85                  90                  95

Cys Gly Gly Asp Cys Ser Asp Val Asp Lys Thr Gln Leu Glu Phe Phe
```

```
            100                 105                 110
Lys Ile Glu Gln Ser Gly Leu Val Asn Gly Ser Asp Pro Pro Gly Thr
        115                 120                 125

Trp Ala Thr Asp Asn Leu Ile Ser Asn Asn Asn Ser Trp Thr Val Thr
    130                 135                 140

Ile Pro Ser Thr Leu Glu Pro Gly Gly Tyr Val Leu Arg His Glu Ile
145                 150                 155                 160

Ile Ala Leu His Ser Ala Gly Gln Leu Asn Gly Ala Gln Asn Tyr Pro
                165                 170                 175

Gln Cys Ile Asn Ile Gln Ile Thr Gln Gly Gly Ser Val Glu Pro Thr
            180                 185                 190

Gly Thr Lys Gly Glu Ala Leu Tyr Thr Asp Thr Asp Pro Gly Ile Leu
        195                 200                 205

Ile Asp Ile Tyr Glu Thr Ile Ala Thr Tyr Asp Ile Pro Gly Pro Ala
    210                 215                 220

Glu Pro Thr Phe
225
```

<210> SEQ ID NO 45
<211> LENGTH: 765
<212> TYPE: DNA
<213> ORGANISM: Artificial sequence
<220> FEATURE:
<223> OTHER INFORMATION: Coding sequence for full length enzyme having
      cellulolytic enhancing activity

<400> SEQUENCE: 45

```
atgctttctt ccaaggcccc cgtgaccctg gctttcgctg gtcttgctgg tctgctctcc      60
gctcctctgg tcaaggccca cggattcgtc cagggcattg ttgttgacgg caccttctac    120
tctggctaca tcgtcgatga gttcccctac atgagcaacc tcctcctgt cattggctgg     180 tccaccactg ccaccgacct tggattcgtc gatggcagcg aataccagga gcccgatatc    240
atctgccacc gtaacggcac ccccgccctc ttgactgcgg aagtcaaggc cggtggtacc    300
gttgagctcc agtggactcc ctggccctcc tctcaccacg acctgtcat cacctacctt     360 gccaactgcg gtggtgactg ctcggatgtt gacaagaccc agctcgagtt cttcaagatc    420
gagcagtccg gtctggtcaa cggctccgac cctcccggca cctgggccac cgacaacctg    480
atctccaaca caacagctg gactgtcacc atccctcca ccctcgagcc cggtggatac      540
gtgctccgcc acgagatcat tgccctgcac tctgctggcc agctcaacgg tgctcagaac    600
tacccccagt gcatcaacat ccagatcacc cagggtggca gcgttgagcc cactggtacc    660
aagggtgaag cgctctacac cgacaccgac cccggtatct tgattgatat ctacgagact    720
attgccacct acgacatccc cggtcctgct gagcccactt tctaa                    765
```

<210> SEQ ID NO 46
<211> LENGTH: 254
<212> TYPE: PRT
<213> ORGANISM: Artificial sequence
<220> FEATURE:
<223> OTHER INFORMATION: Full length sequence of enzyme having
      cellulolytic enhancing activity

<400> SEQUENCE: 46

```
Met Leu Ser Ser Lys Ala Pro Val Thr Leu Ala Phe Ala Gly Leu Ala
1               5                   10                  15

Gly Leu Leu Ser Ala Pro Leu Val Lys Ala His Gly Phe Val Ser Gly
            20                  25                  30
```

Ile Val Val Asp Gly Thr Phe Tyr Ser Gly Tyr Ile Val Asp Glu Tyr
                35                  40                  45

Pro Tyr Met Ser Asn Pro Pro Val Ile Gly Trp Ser Thr Thr Ala
 50                  55                  60

Thr Asp Leu Gly Phe Val Asp Gly Thr Glu Tyr Gln Glu Pro Asp Ile
 65                  70                  75                  80

Ile Cys His Arg Asn Ala Thr Pro Ala Leu Leu Thr Ala Glu Val Lys
                 85                  90                  95

Ala Gly Gly Asp Val Glu Leu Gln Trp Thr Pro Trp Pro Ser Ser His
                100                 105                 110

His Gly Pro Val Ile Thr Tyr Leu Ala Asn Cys Gly Gly Asp Cys Ser
                115                 120                 125

Asp Val Asp Lys Thr Gln Leu Glu Phe Phe Lys Ile Glu Gln Ser Gly
130                 135                 140

Leu Ile Asn Asp Ser Asp Pro Pro Gly Thr Trp Ala Thr Asp Asn Leu
145                 150                 155                 160

Ile Ser Asn Asn Asn Thr Trp Thr Val Thr Ile Pro Ser Thr Leu Glu
                165                 170                 175

Pro Gly Asn Tyr Val Leu Arg His Glu Ile Ile Ala Leu His Ser Ala
                180                 185                 190

Gly Gln Lys Asp Gly Ala Gln Asn Tyr Pro Gln Cys Ile Asn Ile Gln
                195                 200                 205

Ile Thr Gln Gly Gly Thr Val Glu Pro Thr Gly Ala Lys Gly Glu Ala
                210                 215                 220

Leu Tyr Thr Asn Thr Asp Pro Gly Ile Leu Ile Asp Ile Tyr Glu Thr
225                 230                 235                 240

Ile Ala Thr Tyr Asp Ile Pro Gly Pro Ala Glu Pro Thr Phe
                245                 250

<210> SEQ ID NO 47
<211> LENGTH: 228
<212> TYPE: PRT
<213> ORGANISM: Artificial sequence
<220> FEATURE:
<223> OTHER INFORMATION: Mature sequence of enzyme having cellulolytic
      enhancing activity

<400> SEQUENCE: 47

His Gly Phe Val Ser Gly Ile Val Val Asp Gly Thr Phe Tyr Ser Gly
 1               5                  10                  15

Tyr Ile Val Asp Glu Tyr Pro Tyr Met Ser Asn Pro Pro Val Ile
                20                  25                  30

Gly Trp Ser Thr Thr Ala Thr Asp Leu Gly Phe Val Asp Gly Thr Glu
                35                  40                  45

Tyr Gln Glu Pro Asp Ile Ile Cys His Arg Asn Ala Thr Pro Ala Leu
 50                  55                  60

Leu Thr Ala Glu Val Lys Ala Gly Gly Asp Val Glu Leu Gln Trp Thr
 65                  70                  75                  80

Pro Trp Pro Ser Ser His His Gly Pro Val Ile Thr Tyr Leu Ala Asn
                 85                  90                  95

Cys Gly Gly Asp Cys Ser Asp Val Asp Lys Thr Gln Leu Glu Phe Phe
                100                 105                 110

Lys Ile Glu Gln Ser Gly Leu Ile Asn Asp Ser Asp Pro Pro Gly Thr
                115                 120                 125

Trp Ala Thr Asp Asn Leu Ile Ser Asn Asn Asn Thr Trp Thr Val Thr

```
                    130                 135                 140
Ile Pro Ser Thr Leu Glu Pro Gly Asn Tyr Val Leu Arg His Glu Ile
145                 150                 155                 160

Ile Ala Leu His Ser Ala Gly Gln Lys Asp Gly Ala Gln Asn Tyr Pro
                165                 170                 175

Gln Cys Ile Asn Ile Gln Ile Thr Gln Gly Gly Thr Val Glu Pro Thr
            180                 185                 190

Gly Ala Lys Gly Glu Ala Leu Tyr Thr Asn Thr Asp Pro Gly Ile Leu
        195                 200                 205

Ile Asp Ile Tyr Glu Thr Ile Ala Thr Tyr Asp Ile Pro Gly Pro Ala
    210                 215                 220

Glu Pro Thr Phe
225

<210> SEQ ID NO 48
<211> LENGTH: 765
<212> TYPE: DNA
<213> ORGANISM: Artificial sequence
<220> FEATURE:
<223> OTHER INFORMATION: Coding sequence for full length enzyme having
      cellulolytic enhancing activity

<400> SEQUENCE: 48
atgctgagca gcaaggcccc cgtgaccctg gctttcgctg gtcttgctgg cttgctttct      60
gctcctctgg tcaaggccca cggattcgtc tccggcattg ttgttgatgg caccttctac    120
tctggctaca tcgtcgatga gtacccctac atgagcaacc ctcctcccgt cattggctgg    180
tcgaccactg ccaccgacct tggattcgtc gatggcaccg aataccagga gcccgacatc    240
atctgccacc gcaacgccac tcctgctctc ttgactgctg aggtcaaggc cggtggtgat    300
gttgagctcc agtggactcc ctggccctcc tcccaccacg gtcccgtcat cacctacctt    360
gccaactgcg gtggtgactg ctcggatgtt gacaagaccc agctcgagtt cttcaagatt    420
gagcagtccg gtctgatcaa cgactccgac cctcctggta cctgggccac cgacaacctg    480
atctccaaca caacacctg gactgtcacc atcccctcca ccctcgagcc cggcaactac    540
gtgctccgtc acgaaatcat tgccctccac tctgctggcc agaaggatgg tgcccagaac    600 taccccagt gcatcaacat ccagatcacc cagggtggca ccgttgagcc cactggtgcc    660
aagggtgaag cgctctacac caacaccgac cccggtatcc tgatcgacat ctacgagact    720
attgccacct acgacatccc cggtcctgct gagcccacct tttaa                    765
```

POLYPEPTIDES HAVING CELLULOLYTIC ENHANCING ACTIVITY AND USES THEREOF

CROSS-REFERENCE TO RELATED APPLICATIONS

This application is a National Stage entry of International Application No. PCT/EP2017/069049, filed 27 Jul. 2017, which claims priority to European Patent Application Nos. 16181977.6, 16181978.4, 16181980.0, 16181985.9, 16181982.6, 16181984.2, 16181987.5, 16181991.7, 16181919.8, 16181920.6, 16181921.4, 16181922.2, 16181927.1, 16181929.7, 16181930.5, and 16181931.3, all filed 29 Jul. 2016.

REFERENCE TO SEQUENCE LISTING SUBMITTED AS A COMPLIANT ASCII TEXT FILE (.TXT)

Pursuant to the EFS-Web legal framework and 37 CFR §§ 1.821-825 (see MPEP § 2442.03(a)), a Sequence Listing in the form of an ASCII-compliant text file (entitled "Sequence_Listing_2919208-495000_ST25.txt" created on 16 Jan. 2019, and 91,383 bytes in size) is submitted via CD and concurrently with the instant application, and the entire contents of the Sequence Listing are incorporated herein by reference.

BACKGROUND

Field of the Invention

The invention relates to a polypeptide having cellulolytic enhancing activity and to variants and fragments thereof. Moreover, the invention relates to polynucleotides encoding the polypeptide and to variants and fragments thereof. Also included in the invention are nucleic acid constructs and cells comprising such a polynucleotide as well as methods for producing and using the polypeptides, variants and fragments thereof. The invention further concerns compositions comprising the polypeptides, variants and fragments thereof and to processes in which they are used.

Description of Related Art

Carbohydrates constitute the most abundant organic compounds on earth. However, much of this carbohydrate is sequestered in complex polymers including starch and a collection of carbohydrates and lignin known as lignocellulose. The main carbohydrate components of lignocellulose are cellulose, hemicellulose and pectins. These complex polymers are often referred to collectively as lignocellulose.

Bioconversion of lignocellulosic biomass to a sugar that is subsequently fermented to produce alcohol as an alternative to liquid fuels has attracted an intensive attention of researchers since 1970s, when the oil crisis broke out because of decreasing the output of petroleum by OPEC.

Ethanol has been widely used as a 10% blend to gasoline in the USA or as a neat fuel for vehicles in Brazil in the last two decades. More recently, the use of E85, an 85% ethanol blend has been implemented especially for clean city applications. The importance of biofuel will increase in parallel with increases in prices for oil and the gradual depletion of its sources.

Additionally, fermentable sugars are being used to produce plastics, polymers and other bio-based products and this industry is expected to grow substantially, therefore increasing the demand for abundant low cost fermentable sugars which can be used as a feedstock in lieu of petroleum-based feedstocks.

The sequestration of large amounts of carbohydrates in plant biomass provides a plentiful source of potential energy in the form of sugars, both five carbon and six carbon sugars, that could be utilized for numerous industrial processes. However, the enormous energy potential of these carbohydrates is currently under-utilized, because the sugars are locked in complex polymers and hence are not readily accessible for fermentation.

Regardless of the type of cellulosic feedstock, the cost and hydrolytic efficiency of enzymes are major factors that restrict the commercialization of the biomass bioconversion processes. The production costs of microbially produced enzymes are tightly connected with productivity of the enzyme-producing strain, the specific activity of the enzymes, the mode of action of the enzyme and the final activity yield in the fermentation broth.

In spite of the continued research of the last few decades to understand enzymatic lignocellulosic biomass degradation and enzyme production, it remains desirable to discover or to engineer new highly active enzymes and enzyme compositions that can be used to degrade (ligno)cellulosic material. The present invention provides such enzymes.

SUMMARY OF THE INVENTION

The present invention provides a polypeptide which has the ability to modify a cellulosic material. The present invention provides polypeptides having cellulolytic enhancing activity and polynucleotides encoding the polypeptides of the invention. The polypeptides of the invention may have lytic polysaccharide monooxygenase (LPMO) activity.

The polypeptides of the present invention may be used in industrial processes such as the degradation of cellulosic material. They may also be used in the production of sugar from cellulosic material.

Sugars produced in this way may be used in fermentation processes. Accordingly, the invention also provides a process for producing a fermentation product, such as ethanol.

The polypeptides of the current invention may also be used, for example, in the preparation of a food product, in the preparation of a detergent, in the preparation of an animal feed product, in the treatment of pulp, in the manufacture of paper or in the preparation of a fabric or textile or in the cleaning thereof.

According to the invention, there is thus provided a polypeptide having cellulolytic enhancing activity, wherein the polypeptide is selected from the group consisting of:

(a) a polypeptide comprising an amino acid sequence having at least 60% sequence identity with the amino acid sequence of SEQ ID NO: 2, 5, 8, 11, 14, 17, 20, 23, 26, 29, 32, 35, 38, 41, 44 and/or 47;

(b) a polypeptide encoded by a polynucleotide comprising a nucleotide sequence having at least 60% sequence identity to the nucleotide sequence of SEQ ID NO: 3, 6, 9, 12, 15, 18, 21, 24, 27, 30, 33, 36, 39, 42, 45 and/or 48, (c) a polypeptide encoded by a polynucleotide comprising a nucleotide sequence which hybridises under at least high stringency conditions with the complementary strand of SEQ ID NO: 3, 6, 9, 12, 15, 18, 21, 24, 27, 30, 33, 36, 39, 42, 45 and/or 48, and (d) a fragment of the polypeptide of (a), (b), or (c), that has cellulolytic enhancing activity.

The invention further provides:
a polynucleotide, wherein the polynucleotide comprises a nucleotide sequence that is selected from the group consisting of:
  (a) a nucleotide sequence having at least 60% sequence identity with the nucleotide sequence of SEQ ID NO: 3, 6, 9, 12, 15, 18, 21, 24, 27, 30, 33, 36, 39, 42, 45 and/or 48,
  (b) a nucleotide sequence which hybridises under at least high stringency conditions with the complementary strand of SEQ ID NO: 3, 6, 9, 12, 15, 18, 21, 24, 27, 30, 33, 36, 39, 42, 45 and/or 48,
  (c) a fragment which is at least 100 nucleotides in length of a nucleotide sequence as defined in (a) or (b),
  (d) a nucleotide sequence which is degenerate as a result of the genetic code to a nucleotide sequence as defined in any one of (a), (b), or (c), and
  (e) a nucleotide sequence which is the complement of a nucleotide sequence as defined in (a), (b), (c), or (d);
a nucleic acid construct comprising a polynucleotide of the invention;
a host cell comprising a polypeptide, a polynucleotide or a nucleic acid construct according to the invention;
a process for producing a polypeptide of the invention, which process comprises the steps of:
  (a) cultivating a host cell according to the invention under conditions conducive to the production of the polypeptide, and
  (b) optionally, recovering the polypeptide;
a composition comprising:
  (a) a polypeptide of the invention, and
  (b) a cellulase and/or a hemicellulase and/or a pectinase;
a process for degrading cellulosic material, the process comprising the step of contacting the cellulosic material with a polypeptide or a composition of the invention; and
a process for producing a fermentation product, the process comprising the steps of:
  (a) enzymatically hydrolysing a cellulosic material with a polypeptide or a composition of the invention,
  (b) fermenting the enzymatically hydrolysed cellulosic material to produce a fermentation product, and
  (c) optionally, recovering of the fermentation product.

BRIEF DESCRIPTION OF THE SEQUENCES

Figure 1:
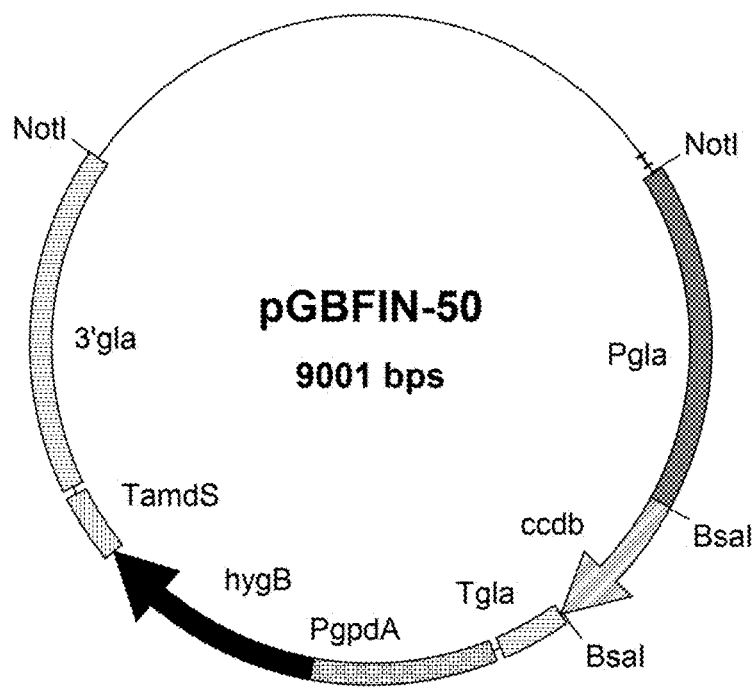
FIG. 1 sets out a schematic representation of the *Aspergillus* expression vector pGBFIN-50.

SEQ ID NOs: 1, 4, 7, 10, 13, 16, 19, 22, 25, 28, 31, 34, 37, 40, 43, 46 set out full-length amino acid sequences (including signal peptide) of the polypeptides of the invention.

SEQ ID NOs: 2, 5, 8, 11, 14, 17, 20, 23, 26, 29, 32, 35, 38, 41, 44, 47 set out mature amino acid sequences of the polypeptides of the invention.

SEQ ID NOs: 3, 6, 9, 12, 15, 18, 21, 24, 27, 30, 33, 36, 39, 42, 45, 48 set out nucleotide sequences (including stop codon) encoding the full-length polypeptides of the invention (SEQ ID NO: 1).

DETAILED DESCRIPTION OF A PREFERRED EMBODIMENT

Throughout the present specification and the accompanying claims, the words "comprise" and "include" and variations such as "comprises", "comprising", "includes" and "including" are to be interpreted inclusively. That is, these words are intended to convey the possible inclusion of other elements or integers not specifically recited, where the context allows.

The articles "a" and "an" are used herein to refer to one or to more than one (i.e. to one or at least one) of the grammatical object of the article. By way of example, "an element" may mean one element or more than one element.

The term "derived from" also includes the terms "originated from", "obtained from", "obtainable from", "isolated from", and "created from", and generally indicates that one specified material find its origin in another specified material or has features that can be described with reference to the other specified material. As used herein, a substance (e.g. a nucleic acid molecule or polypeptide) "derived from" a microorganism preferably means that the substance is native to that microorganism.

Polypeptide

The present invention provides a polypeptide which has the ability to modify a cellulosic material. The present invention provides a polypeptide which has the ability to degrade cellulosic material. In an embodiment, the polypeptide of the present invention has cellulolytic enhancing activity. In an embodiment the polypeptide of the present invention has LPMO activity. In an embodiment the polypeptide of the present invention is an isolated polypeptide.

Endo-1,4-β-glucanases (EG) and exo-cellobiohydrolases (CBH) catalyze the hydrolysis of insoluble cellulose to cellooligosaccharides (cellobiose as a main product), while β-glucosidases (BGL) convert the oligosaccharides, mainly cellobiose and cellotriose, to glucose.

Xylanases together with other accessory enzymes, for example α-L-arabinofuranosidases, feruloyl and acetyl-xylan esterases, glucuronidases, and β-xylosidases catalyze the hydrolysis of part of the hemicelluloses.

Pectic substances include pectins, arabinans, galactans and arabinogalactans. Pectins are the most complex polysaccharides in the plant cell wall. They are built up around a core chain of α(1,4)-linked D-galacturonic acid units interspersed to some degree with L-rhamnose. In any one cell wall there are a number of structural units that fit this description and it has generally been considered that in a single pectic molecule the core chains of different structural units are continuous with one another.

Pectinases include, for example an endo-polygalacturonase, a pectin methyl esterase, an endo-galactanase, a β-galactosidase, a pectin acetyl esterase, an endo-pectin lyase, pectate lyase, α-rhamnosidase, an exo-galacturonase, an exo-polygalacturonate lyase, a rhamnogalacturonan hydrolase, a rhamnogalacturonan lyase, a rhamnogalacturonan acetyl esterase, a rhamnogalacturonan galacturonohydrolase, a xylogalacturonase, an α-arabinofuranosidase.

Lytic polysaccharide monooxygenases (LPMO) are recently classified by CAZy in family AA9 (Auxiliary Activity Family 9), family AA10 (Auxiliary Activity Family 10), family AA11 (Auxiliary Activity Family 11) or family AA13 (Auxiliary Activity Family 13). Lytic polysaccharide monooxygenases are able to open a crystalline glucan structure. Lytic polysaccharide monooxygenases may also affect cello-oligosaccharides. PMO and LPMO are used herein interchangeably. Often in literature these proteins are mentioned to enhance the action of cellulases on cellulosic material, i.e. have cellulolytic enhancing activity. Thus, a polypeptide of the invention may be one which enhances the hydrolysis of a cellulosic material by proteins having cellulolytic acfivity.

As set out above, a polypeptide of the invention will typically have cellulolytic enhancing activity. In an embodiment they will have LPMO activity. In an embodiment they display catalytic activity via an oxidative cleavage reaction on cellulosic material.

The polypeptides of the invention may however also have one or more alternative and/or additional activities as mentioned above. Also, a composition of the invention as described herein may comprise one or more of the activities mentioned above in addition to the activity provided by the polypeptide of the invention.

In an embodiment the polypeptide of the present invention has cellulolytic enhancing activity, wherein the polypeptide is selected from the group consisting of (a) a polypeptide comprising an amino acid sequence having at least 60% sequence identity with the amino acid sequence of SEQ ID NO: 2, 5, 8, 11, 14, 17, 20, 23, 26, 29, 32, 35, 38, 41, 44 and/or 47, (b) a polypeptide encoded by a polynucleotide comprising a nucleotide sequence having at least 60% sequence identity to the nucleotide sequence of SEQ ID NO: 3, 6, 9, 12, 15, 18, 21, 24, 27, 30, 33, 36, 39, 42, 45 and/or 48, (c) a polypeptide encoded by a polynucleotide comprising a nucleotide sequence which hybridises under at least high stringency conditions with the complementary strand of SEQ ID NO: 3, 6, 9, 12, 15, 18, 21, 24, 27, 30, 33, 36, 39, 42, 45 and/or 48, and (d) a fragment of the polypeptide of (a), (b), or (c), that has cellulolytic enhancing activity.

Advantageously, the polypeptide of the invention has cellulolytic enhancing activity. The polypeptide of the invention may enhance the hydrolysis of a cellulosic material catalyzed by one or more polypeptides having cellulolytic activity by reducing the amount of cellulolytic enzyme required to reach the same degree of hydrolysis, preferably at least 1.01-fold, e.g., at least 1.05-fold, at least 1.10-fold, at least 1.25-fold, at least 1.5-fold, at least 2-fold, at least 3-fold, at least 4-fold, at least 5-fold, at least 10-fold, or at least 20-fold.

The cellulolytic enhancing activity can be determined by measuring the increase in sugar release (e.g. glucose release) during hydrolysis of a cellulosic material by a cellulolytic enzyme composition (e.g. the *Rasamsonia* enzyme compositions as used in the Examples or commercial enzyme compositions such as Celluclast® combined with Novozyme 188 (obtainable from Novozymes, Denmark or Sigma-Aldrich®, USA), Accellerase® 1000 (obtainable from Genencor, USA or Sigma-Aldrich®, USA), and Methaplus® (obtainable from DSM, The Netherlands)) in the presence or absence of a polypeptide of the present invention.

In an embodiment a polypeptide of the invention may be added on top of the enzyme composition. Alternatively, a polypeptide of the invention may be replacing part of the enzyme composition by an equal amount (based on protein). Typical conditions include using 0.9 mg/g dry matter of acid-pretreated corn stover of the polypeptide of the invention on top of 1.6 mg/g dry matter of acid-pretreated corn stover of a cellulolytic enzyme composition (comprising 0.225 mg/g dry matter of acid-pretreated corn stover of beta-glucosidase (SEQ ID NO:2 from WO 2012/000890), 0.75 mg/g dry matter of acid-pretreated corn stover of cellobiohydrolase I (SEQ ID NO: 2 from WO 2010/122141), 0.625 mg/g dry matter of acid-pretreated corn stover of cellobiohydrolase II (SEQ ID NO: 2 from WO 2011/098580)) in a hydrolysis for 72 hours at pH 4.5 and a temperature of 62° C.

Dilute-acid pre-treated corn stover may be obtained as described in Schell, D. J., Applied Biochemistry and Biotechnology (2003), vol. 105-108, pp 69-85. A pilot scale pretreatment reactor can be used operating at steady state conditions of 190° C., 1 min residence time and an effective $H_2SO_4$ acid concentration of 1.45% (w/w) in the liquid phase. For the preparation of low acid pretreated corn stover, also referred to as mildly pretreated corn stover, a pilot scale pretreatment reactor may be used operating at steady state conditions of 182° C., 4.7 min residence time and an effective $H_2SO_4$ acid concentration of 0.35% (w/w) in the liquid aiming at a pH of 2.5.

According to a preferred embodiment the polypeptide of the invention is a "thermostable" enzyme. In another preferred embodiment, the polynucleotide according to the invention encodes a "thermostable" enzyme. Herein, "thermostable" enzyme means that the enzyme has a temperature optimum of 60° C. or higher. In an embodiment the enzyme has a temperature optimum of 65° C. or higher, 70° C. or higher, 75° C. or higher, 80° C. or higher, or 85° C. or higher. In general, the temperature optimum will be lower than 95° C. The temperature optimum can be measured when using the enzyme in a hydrolysis for 72 hours at optimum pH conditions.

According to a preferred embodiment the polypeptide of the invention has a pH optimum in between pH 2 and pH 8. Preferably, the enzyme has a pH optimum of 6 or lower, 5.5 or lower, 5.0 or lower, 4.5 or lower, 4.0 or lower, or 3.5 or lower. Preferably, the enzyme has a pH optimum of 2.0 or higher, preferably 2.5 or higher. The pH optimum can be measured when using the enzyme in a hydrolysis for 72 hours at optimum temperature conditions.

In an embodiment the polypeptide of the invention comprises an amino acid sequence having at least 60% sequence identity with the amino acid sequence of SEQ ID NO: 1, 4, 7, 10, 13, 16, 19, 22, 25, 28, 31, 34, 37, 40, 43 and/or 46 or SEQ ID NO: 2, 5, 8, 11, 14, 17, 20, 23, 26, 29, 32, 35, 38, 41, 44 and/or 47. In an embodiment the polypeptide of the invention comprises an amino acid sequence having at least 65% sequence identity, at least 70% sequence identity, at least 75% sequence identity, at least 76% sequence identity, at least 77% sequence identity, at least 78% sequence identity, at least 79% sequence identity, at least 80% sequence identity, at least 81% sequence identity, at least 82% sequence identity, at least 83% sequence identity, at least 84% sequence identity, at least 85% sequence identity, at least 86% sequence identity, at least 87% sequence identity, at least 88% sequence identity, at least 89% sequence identity, at least 90% sequence identity, at least 91% sequence identity, at least 92% sequence identity, at least 93% sequence identity, at least 94% sequence identity, at least 95% sequence identity, at least 96% sequence identity, at least 97% sequence identity, at least 98% sequence identity, at least 99% sequence identity, with the amino acid sequence of SEQ ID NO: 1, 4, 7, 10, 13, 16, 19, 22, 25, 28, 31, 34, 37, 40, 43 and/or 46 or SEQ ID NO: 2, 5, 8, 11, 14, 17, 20, 23, 26, 29, 32, 35, 38, 41, 44 and/or 47. In an embodiment the polypeptide of the invention comprises or consists of the amino acid sequence of SEQ ID NO: 1, 4, 7, 10, 13, 16, 19, 22, 25, 28, 31, 34, 37, 40, 43 or 46 or SEQ ID NO: 2, 5, 8, 11, 14, 17, 20, 23, 26, 29, 32, 35, 38, 41, 44 or 47. SEQ ID NO: 2, 5, 8, 11, 14, 17, 20, 23, 26, 29, 32, 35, 38, 41, 44 and 47 are the mature forms of the polypeptides set out by amino acid sequences SEQ ID NO: 1, 4, 7, 10, 13, 16, 19, 22, 25, 28, 31, 34, 37, 40, 43 and 46, respectively.

The invention also features biologically active fragments of the polypeptides according to the invention. Biologically active fragments of a polypeptide of the invention include polypeptides comprising amino acid sequences sufficiently identical to or derived from the amino acid sequence of SEQ ID NO: 1, 4, 7, 10, 13, 16, 19, 22, 25, 28, 31, 34, 37, 40, 43 and/or 46 or SEQ ID NO: 2, 5, 8, 11, 14, 17, 20, 23, 26, 29, 32, 35, 38, 41, 44 and/or 47, which include fewer amino acids than the full-length polypeptides as given in SEQ ID NO: 1, 4, 7, 10, 13, 16, 19, 22, 25, 28, 31, 34, 37, 40, 43 and/or 46 or SEQ ID NO: 2, 5, 8, 11, 14, 17, 20, 23, 26, 29, 32, 35, 38, 41, 44 and/or 47, but which exhibit at least one biological activity of the corresponding full-length polypeptide. Typically, biologically active fragments comprise a domain or motif with at least one activity of the polypeptide of the invention. A biologically active fragment of a polypeptide of the invention can be a polypeptide which is, for example, about 10, about 25, about 50, about 100 or more amino acids in length or at least about 100 amino acids, at least 150, 200, 250, 300, 350, 400 amino acids in length, or of a length up to the total number of amino acids of the polypeptide of the invention. Moreover, other biologically active portions, in which other regions of the polypeptide are deleted, can be prepared by recombinant techniques and evaluated for one or more of the biological activities of the native form of a polypeptide of the invention. The invention also features nucleic acid fragments which encode the above biologically active fragments of the polypeptide of the invention.

In an embodiment the polypeptide of the invention is improved. Improved polypeptides are polypeptides, wherein at least one biological activity is improved compared to the polypeptides known in the art, such as a wild type polypeptide.

The cellulolytic enhancing activity of the polypeptide of the invention may be analysed according to the assays as described in the Examples.

A polypeptide of the invention may have one or more improved properties, such as enhanced thermostability, enhanced activity in presence of dissolved glucose, enhanced activity in presence of dissolved gluconic acid, enhanced activity in presence of dissolved ammonium sulphate, enhanced activity in presence of dissolved sodium chloride, enhanced activity in presence of ethanol, enhanced activity in presence of dimethyl sulfoxide (DMSO) or the ability to be produced at higher titers in the heterologous expression organisms *Aspergillus niger* or *Talaromyces emersonii*.

The properties of a polypeptide of the invention may be determined using the assay described above.

As used herein, the term "polypeptide" refers to a molecule comprising amino acid residues linked by peptide bonds and containing more than five amino acid residues. The amino acids are identified by either the single letter or three letter designations. The term "protein" as used herein is synonymous with the term "polypeptide" and may also refer to two or more polypeptides. Thus, the terms "protein", "peptide" and "polypeptide" can be used interchangeably. Polypeptides may optionally be modified (e.g., glycosylated, phosphorylated, acylated, farnesylated, prenylated, sulfonated, and the like) to add functionality. Polypeptides exhibiting activity may be referred to as enzymes. It will be understood that, as a result of the degeneracy of the genetic code, a multitude of nucleotide sequences encoding a given polypeptide may be produced.

The term "mature polypeptide" or "mature form of a polypeptide" is defined herein as a polypeptide in its final form and is obtained after translation of mRNA into polypeptide and post-translational modifications of the polypeptide. Post-translational modifications include N-terminal processing, C-terminal truncation, glycosylation, phosphorylation and removal of leader sequences such as signal peptides, pro-peptides and/or prepro-peptides by cleavage.

The term "a fragment of the polypeptide" is defined herein as a polypeptide having one or more amino acids deleted from the amino and/or carboxyl terminus of the parent polypeptide or a homologous sequence thereof. The term refers to biologically active fragments. The fragment has cellulolytic enhancing activity. As indicated herein the fragment may be for example, about 10, about 25, about 50, about 100 or more amino acids in length or at least about 100 amino acids, at least 150, 200, 250, 300, 350, 400 amino acids in length, or may be of a length up to the total number of amino acids of the polypeptide of the invention.

The term "prepro-peptide" is defined herein as a signal peptide and pro-peptide present at the amino terminus of a polypeptide, where the pro-peptide is linked (or fused) in frame to the amino terminus of a polypeptide and the signal peptide is linked in frame (or fused) to the amino terminus of the pro-peptide region. The term "signal peptide" is defined herein as a peptide linked (fused) in frame to the amino terminus of a polypeptide and directs the polypeptide into the cell secretory pathway. A pro-peptide may be present between the signal peptide and the amino terminus of the polypeptide. The term "pro-peptide" is an amino acid sequence linked (fused) in frame to the amino terminus of a polypeptide having biological activity, wherein the resultant polypeptide is known as a proenzyme or pro-polypeptide (or a zymogen in some cases), A pro-polypeptide is generally biologically inactive and can be converted to a mature active polypeptide by catalytic or autocatalytic cleavage of the pro-peptide from the pro-polypeptide.

A peptide or polypeptide that is a variant of the polypeptide of the present invention, such as a functional equivalent, is also comprised within the present invention. The above polypeptides are collectively comprised in the term "polypeptides according to the invention".

As used herein, the terms "variant, "derivative", "mutant" or "homologue" can be used interchangeably. They can refer to either polypeptides or polynucleotides. Variants include substitutions, insertions, deletions, truncations, transversions, and/or inversions, at one or more locations relative to a reference sequence. Variants can be made for example by site-saturation mutagenesis, scanning mutagenesis, insertional mutagenesis, random mutagenesis, site-directed mutagenesis, and directed-evolution, as well as various other recombination approaches. Variant polypeptides may differ from a reference polypeptide by a small number of amino acid residues and may be defined by their level of primary amino acid sequence homology/identity with a reference polypeptide. In general, related polypeptides may have several essential amino acids in common (which are sometimes referred to as motif). The identity of those essential amino acids can be identified from the alignment of related polypeptides. Mutating of one or more of the essential amino acids may change the properties of the polypeptide such as substrate specificity, thermostability or change of pH-optimum. Mutating of one or more of the non-essential amino acids may have smaller effect on the properties of the polypeptide such as substrate specificity, thermostability or change of pH-optimum.

In an embodiment variant polypeptides have at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, or even at least 99% amino acid sequence identity with a reference polypeptide. Methods for determining percent identity are known in the art and described herein. Generally, the variants retain the characteristic nature of the reference polypeptide, but have altered properties in some specific aspects. For example, a variant may have a modified pH-optimum, a modified substrate binding ability, a modified resistance to enzymatic degradation or other degradation, an increased or decreased activity, a modified temperature or oxidative stability, but retains its characteristic functionality. Variants further include polypeptides with chemical modifications that change the characteristics of a reference polypeptide.

According to one aspect of the invention the polypeptide of the invention may comprise the amino acid sequence set out in SEQ ID NO: 1, 4, 7, 10, 13, 16, 19, 22, 25, 28, 31, 34, 37, 40, 43 or 46 or SEQ ID NO: 2, 5, 8, 11, 14, 17, 20, 23, 26, 29, 32, 35, 38, 41, 44 or 47 or an amino acid sequence that differs in 1, 2, 3, 4, 5, 6, 7, 8, 9, 10, 11 or 12 amino acids from the amino acid sequence set out in SEQ ID NO: 1, 4, 7, 10, 13, 16, 19, 22, 25, 28, 31, 34, 37, 40, 43 or 46 or SEQ ID NO: 2, 5, 8, 11, 14, 17, 20, 23, 26, 29, 32, 35, 38, 41, 44 or 47 and wherein the polypeptide still has the cellulolytic enhancing activity of the polypeptide of the invention. The skilled person will appreciate that these minor amino acid changes in the polypeptide of the invention may be present (for example, naturally occurring mutations) or made (for example, using r-DNA technology) without loss of the function or activity. In case these mutations are present in a binding domain, active site, or other functional domain of the polypeptide, a property of the polypeptide may change (for example its thermostability), but the polypeptide may keep its cellulolytic enhancing activity. In case a mutation is present which is not close to the active site, binding domain, or other functional domain, less effect may be expected.

Functional equivalents of a polypeptide according to the invention can also be identified by screening combinatorial libraries of mutants, e.g. truncation mutants, of the polypeptide of the invention for cellulolytic enhancing activity. In one embodiment a variegated library of variants is generated by combinatorial mutagenesis at the nucleic acid level. Several techniques are known in the art for screening gene products of combinatorial libraries made by point mutations of truncation, and for screening cDNA libraries for gene products having a selected property. The most widely used techniques, which are amenable to high through-put analysis, for screening large gene libraries typically include cloning the gene library into replicable expression vectors, transforming appropriate cells with the resulting library of vectors, and expressing the combinatorial genes under conditions in which detection of a desired activity facilitates isolation of the vector encoding the gene whose product was detected.

In addition to the nucleotide sequences shown in SEQ ID NO: 3, 6, 9, 12, 15, 18, 21, 24, 27, 30, 33, 36, 39, 42, 45 and 48, it will be apparent for the person skilled in the art that DNA sequence polymorphisms may exist within a given population, which may lead to changes in the amino acid sequence of the polypeptide. Such genetic polymorphisms may exist in cells from different populations or within a population due to natural allelic variation. Allelic variants may also include functional equivalents. Fragments of a polynucleotide according to the invention may also comprise polynucleotides not encoding functional polypeptides. Such polynucleotides may function as probes or primers for a PCR reaction.

With regard to polynucleotides, the terms "variant, "derivative", "mutant" or "homologue" refer to a polynucleotide that encodes a variant polypeptide, that has a specified degree of homology/identity with a reference polynucleotide, or that hybridizes under stringent conditions to a reference polynucleotide or the complement thereof. Preferably, a variant polynucleotide has at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, or even at least 99% nucleotide sequence identity with a reference polynucleotide. Methods for determining percent identity are known in the art and described herein.

Homology and Identity

The terms "sequence homology" or "sequence identity" are used interchangeably herein. For the purpose of this invention, it is defined here that in order to determine the percentage of sequence homology or sequence identity of two amino acid sequences or of two nucleotide sequences, the sequences are aligned for optimal comparison purposes. In order to optimize the alignment between the two sequences, gaps may be introduced in any of the two sequences that are compared. Such alignment can be carried out over the full-length of the sequences being compared. Alternatively, the alignment may be carried out over a shorter length, for example over about 20, about 50, about 100 or more nucleotides or amino acids. The sequence identity is the percentage of identical matches between the two sequences over the reported aligned region.

A comparison of sequences and determination of percentage of sequence identity between two sequences can be accomplished using a mathematical algorithm. The skilled person will be aware of the fact that several different computer programs are available to align two sequences and determine the identity between two sequences (Kruskal, J. B. (1983) An overview of sequence comparison. In D. Sankoff and J. B. Kruskal, (ed.), Time warps, string edits and macromolecules: the theory and practice of sequence comparison, pp. 1-44 Addison Wesley). The percent sequence identity between two amino acid sequences or between two nucleotide sequences may be determined using the Needleman and Wunsch algorithm for the alignment of two sequences. (Needleman, S. B. and Wunsch, C. D. (1970) J. Mol. Biol. 48, 443-453). Both amino acid sequences and nucleotide sequences can be aligned by the algorithm. The Needleman-Wunsch algorithm has been implemented in the computer program NEEDLE. For the purpose of this invention, the NEEDLE program from the EMBOSS package was used (version 2.8.0 or higher, EMBOSS: The European Molecular Biology Open Software Suite (2000) Rice,P. Longden,I. and Bleasby,A. Trends in Genetics 16, (6) pp 276-277, http://emboss.bioinformatics.nl/). For amino acid sequences, EBLOSUM62 is used for the substitution matrix. For nucleotide sequence, EDNAFULL is used. The optional parameters used are a gap-open penalty of 10 and a gap extension penalty of 0.5. The skilled person will appreciate that all these different parameters will yield slightly different results but that the overall percentage identity of two sequences is not significantly altered when using different algorithms.

After alignment by the program NEEDLE as described above the percentage of sequence identity between a query sequence of the invention and a sequence of the invention is calculated as follows: Number of corresponding positions in the alignment showing an identical amino acid or identical nucleotide in both sequences divided by the total length of the alignment after subtraction of the total number of gaps in the alignment. The identity defined as herein can be obtained from NEEDLE by using the NOBRIEF option and is labeled in the output of the program as "longest-identity".

The nucleotide and amino acid sequences of the present invention can further be used as a "query sequence" to perform a search against sequence databases to, for example, identify other family members or related sequences. Such searches can be performed using the NBLAST and XBLAST programs (version 2.0) of Altschul, et al. (1990) J. Mol. Biol. 215:403-10. BLAST nucleotide searches can be performed with the NBLAST program, score=100, word length=12 to obtain nucleotide sequences homologous to polynucleotides of the invention. BLAST protein searches can be performed with the XBLAST program, score=50, word length=3 to obtain amino acid sequences homologous to polypeptides of the invention. To obtain gapped alignments for comparison purposes, Gapped BLAST can be utilized as described in Altschul et al., (1997) Nucleic Acids Res. 25(17): 3389-3402. When utilizing BLAST and Gapped BLAST programs, the default parameters of the respective programs (e.g., XBLAST and NBLAST) can be used.

Compositions

The polypeptide of the invention may be comprised in a composition. Preferably, the composition is enriched in the polypeptide. By "enriched" is meant that the polypeptide in the composition is increased, for example with at least a factor of 1.1, preferably 1.5, more preferably 2 on protein level compared to the composition without the overexpressed polypeptide of the invention. The composition may comprise a polypeptide of the present invention as the major enzymatic component, e.g. a mono-component composition. Alternatively, the composition may comprise multiple enzymatic activities. The polypeptide compositions may be prepared in accordance with methods known in the art and may be in the form of a liquid or a dry composition. For instance, the polypeptide composition may be in the form of a granulate or a microgranulate. The polypeptide to be included in the composition may be stabilized in accordance with methods known in the art. The dosage of the composition of the invention and other conditions under which the composition is used depend on the ultimate use of the composition.

The invention is concerned with a composition comprising (a) a polypeptide according to the invention, and (b) a cellulase and/or a hemicellulase and/or a pectinase. In an embodiment the cellulase is a cellobiohydrolase I, a cellobiohydrolase II, an endo-β-1,4-glucanase, a β-glucosidase or a β-(1,3)(1,4)-glucanase. In an embodiment the hemicellulase is an endoxylanase, a β-xylosidase, an α-L-arabinofuranosidase, an α-D-glucuronidase, an acetyl-xylan esterase, a feruloyl esterase, a coumaroyl esterase, an α-galactosidase, a β-galactosidase, a β-mannanase or a β-mannosidase. Of course, the composition may also comprise more than one cellulase and/or a hemicellulase and/or a pectinase. For example, two cellulases, two hemicellulases and one pectinase or five cellulases, one hemicellulose and three pectinases. Any combination is possible. Suitable cellulases and/or hemicellulases and/or pectinases are described herein.

Polypeptides can be produced by different processes and mixed into an optimal composition or the compositions can be made directly as a mixture by one fermentation.

A composition of the invention may comprise one, two or three or more classes of cellulase, for example a polypeptide of the invention, an endo-1,4-β-glucanase (EG), an exo-cellobiohydrolase (CBH) and a β-glucosidase (BG).

A composition of the invention may comprise a polypeptide which has the same enzymatic activity, for example cellulolytic enhancing activity, as that provided by a polypeptide of the invention.

A composition of the invention may comprise a polypeptide which has a different type of cellulase activity and/or hemicellulase activity and/or pectinase activity than that provided by a polypeptide of the invention. For example, a composition of the invention may comprise one type of cellulase and/or hemicellulase activity and/or pectinase activity provided by a polypeptide of the invention and a second type of cellulase and/or hemicellulase activity and/or pectinase activity provided by an additional cellulose/hemicellulase/pectinase.

Herein, a cellulase is any polypeptide which is capable of degrading and/or hydrolysing cellulose or enhancing the degradation and/or hydrolysis of cellulose. A polypeptide which is capable of degrading cellulose is a polypeptide which is capable of catalysing the process of breaking down cellulose into smaller units, either partially, for example into cellodextrins, or completely into glucose monomers. Degradation will typically take place by a hydrolysis reaction.

Herein, a hemicellulase is any polypeptide which is capable of degrading and/or hydrolysing hemicellulose or enhancing the degradation and/or hydrolysis of hemicellulose. That is to say, a hemicellulase may be capable of degrading one or more of xylan, glucuronoxylan, arabinoxylan, glucomannan and xyloglucan. A polypeptide which is capable of degrading a hemicellulose is a polypeptide which is capable of catalysing the process of breaking down the hemicellulose into smaller polysaccharides, either partially, for example into oligosaccharides, or completely into sugar monomers, for example hexose or pentose sugar monomers. A hemicellulase may give rise to a mixed population of oligosaccharides and sugar monomers. Degradation will typically take place by a hydrolysis reaction.

Herein, a pectinase is any polypeptide which is capable of degrading pectin. A polypeptide which is capable of degrading pectin is a polypeptide which is capable of catalysing the process of breaking down pectin into smaller units, either partially, for example into oligosaccharides, or completely into sugar monomers. A pectinase according to the invention may give rise to a mixed population of oligosaccharides and sugar monomers. Degradation will typically take place by a hydrolysis reaction.

The composition may comprise a cellulase and/or a hemicellulase and/or a pectinase from *Rasamsonia* or a source other than *Rasamsonia*. They may be used together with one or more *Rasamsonia* enzymes or they may be used without additional *Rasamsonia* enzymes being present.

For example, the composition of the invention may comprise a beta-glucosidase (BG) from *Aspergillus*, such as *Aspergillus oryzae*, such as the one disclosed in WO 02/095014 or the fusion protein having beta-glucosidase activity disclosed in WO 2008/057637, or *Aspergillus*

*fumigatus*, such as the one disclosed as SEQ ID NO:2 in WO 2005/047499 or SEQ ID NO:5 in WO 2014/130812 or an *Aspergillus fumigatus* beta-glucosidase variant, such as one disclosed in WO 2012/044915, such as one with the following substitutions: F100D, S283G, N456E, F512Y (using SEQ ID NO: 5 in WO 2014/130812 for numbering), or *Aspergillus aculeatus*, *Aspergillus niger* or *Aspergillus kawachi*. In another embodiment the beta-glucosidase is derived from *Penicillium*, such as *Penicillium brasilianum* disclosed as SEQ ID NO:2 in WO 2007/019442, or from *Trichoderma*, such as *Trichoderma reesei*, such as ones described in U.S. Pat. Nos. 6,022,725, 6,982,159, 7,045,332, 7,005,289, US 2006/0258554 US 2004/0102619. In an embodiment even a bacterial beta-glucosidase can be used. In another embodiment the beta-glucosidase is derived from *Thielavia terrestris* (WO 2011/035029) or *Trichophaea saccata* (WO 2007/019442). In an embodiment the enzyme composition comprises a beta-glucosidase from *Rasamsonia*, such as *Rasamsonia emersonii* (see WO 2012/000886).

For example, the composition of the invention may comprise an endoglucanase (EG) from *Trichoderma*, such as *Trichoderma reesei*; from *Humicola*, such as a strain of *Humicola insolens*; from *Aspergillus*, such as *Aspergillus aculeatus* or *Aspergillus kawachii*; from *Erwinia*, such as *Erwinia carotovara*; from *Fusarium*, such as *Fusarium oxysporum*; from *Thielavia*, such as *Thielavia terrestris*; from *Humicola*, such as *Humicola grisea* var. *thermoidea* or *Humicola insolens*; from *Melanocarpus*, such as *Melanocarpus albomyces*; from *Neurospora*, such as *Neurospora crassa*; from *Myceliophthora*, such as *Myceliophthora thermophila*; from *Cladorrhinum*, such as *Cladorrhinum foecundissimum* and/or from *Chrysosporium*, such as a strain of *Chrysosporium lucknowense*. In an embodiment the endoglucanase is from *Rasamsonia*, such as a strain of *Rasamsonia emersonii* (see WO 01/70998). In an embodiment even a bacterial endoglucanase can be used including, but are not limited to, *Acidothermus cellulolyticus* endoglucanase (see WO 91/05039; WO 93/15186; U.S. Pat. No. 5,275,944; WO 96/02551; U.S. Pat. No. 5,536,655, WO 00/70031, WO 05/093050); *Thermobifida fusca* endoglucanase III (see WO 05/093050); and *Thermobifida fusca* endoglucanase V (see WO 05/093050).

For example, the composition of the invention may comprise a cellobiohydrolase I from *Aspergillus*, such as *Aspergillus fumigatus*, such as the Cel7A CBH I disclosed in SEQ ID NO:6 in WO 2011/057140 or SEQ ID NO:6 in WO 2014/130812, or from *Trichoderma*, such as *Trichoderma reesei*; from *Chaetomium*, such as *Chaetomium thermophilum*; from *Talaromyces*, such as *Talaromyces leycettanus* or from *Penicillium*, such as *Penicillium emersonii*. In an embodiment the enzyme composition comprises a cellobiohydrolase I from *Rasamsonia*, such as *Rasamsonia emersonii* (see WO 2010/122141).

For example, the composition of the invention may comprise a cellobiohydrolase II from *Aspergillus*, such as *Aspergillus fumigatus*, such as the one in SEQ ID NO:7 in WO 2014/130812 or from *Trichoderma*, such as *Trichoderma reesei*, or from *Talaromyces*, such as *Talaromyces leycettanus*, or from *Thielavia*, such as *Thielavia terrestris*, such as cellobiohydrolase II CEL6A from *Thielavia terrestris*. In an embodiment the enzyme composition comprises a cellobiohydrolase II from *Rasamsonia*, such as *Rasamsonia emersonii* (see WO 2011/098580).

For example, the composition of the invention may comprise a polypeptide having cellulolytic enhancing activity from *Thermoascus*, such as *Thermoascus aurantiacus*, such as the one described in WO 2005/074656 as SEQ ID NO:2 and SEQ ID NO: 3 in WO2014/130812 and in WO 2010/065830; or from *Thielavia*, such as *Thielavia terrestris*, such as the one described in WO 2005/074647 as SEQ ID NO: 8 or SEQ ID NO:4 in WO2014/130812 and in WO 2008/148131, and WO 2011/035027; or from *Aspergillus*, such as *Aspergillus fumigatus*, such as the one described in WO 2010/138754 as SEQ ID NO:2 or SEQ ID NO: 3 in WO2014/130812; or from *Penicillium*, such as *Penicillium emersonii*, such as the one disclosed as SEQ ID NO:2 in WO 2011/041397 or SEQ ID NO:2 in WO2014/130812. Other suitable polypeptides having cellulolytic enhancing activity include, but are not limited to, *Trichoderma reesei* (see WO 2007/089290), *Myceliophthora thermophila* (see WO 2009/085935, WO 2009/085859, WO 2009/085864, WO 2009/085868), *Penicillium pinophilum* (see WO 2011/005867), *Thermoascus* sp. (see WO 2011/039319), and *Thermoascus crustaceous* (see WO 2011/041504). In an embodiment, the lytic polysaccharide monooxygenase is from *Rasamsonia*, e.g. *Rasamsonia emersonii* (see WO 2012/000892). In one aspect, the polypeptide having cellulolytic enhancing activity is used in the presence of a soluble activating divalent metal cation according to WO 2008/151043, e.g. manganese sulfate. In one aspect, the polypeptide having cellulolytic enhancing activity is used in the presence of a dioxy compound, a bicyclic compound, a heterocyclic compound, a nitrogen-containing compound, a quinone compound, a sulfur-containing compound, or a liquor obtained from a pretreated cellulosic material such as pretreated corn stover.

Other cellulolytic enzymes that may be comprised in the composition of the invention are described in WO 98/13465, WO 98/015619, WO 98/015633, WO 99/06574, WO 99/10481, WO 99/025847, WO 99/031255, WO 2002/101078, WO 2003/027306, WO 2003/052054, WO 2003/052055, WO 2003/052056, WO 2003/052057, WO 2003/052118, WO 2004/016760, WO 2004/043980, WO 2004/048592, WO 2005/001065, WO 2005/028636, WO 2005/093050, WO 2005/093073, WO 2006/074005, WO 2006/117432, WO 2007/071818, WO 2007/071820, WO 2008/008070, WO 2008/008793, U.S. Pat. Nos. 5,457,046, 5,648, 263, and 5,686,593, to name just a few.

In addition, examples of xylanases that may be comprised in the composition of the invention include, but are not limited to, xylanases from *Aspergillus aculeatus* (see WO 94/21785), *Aspergillus fumigatus* (see WO 2006/078256), *Penicillium pinophilum* (see WO 2011/041405), *Penicillium* sp. (see WO 2010/126772), *Thielavia terrestris* NRRL 8126 (see WO 2009/079210), *Talaromyces leycettanus, Thermobifida fusca*, or *Trichophaea saccata* GH10 (see WO 2011/057083). In an embodiment the enzyme composition comprises an endoxylanase from *Rasamsonia*, such as *Rasamsonia emersonii* (see WO 02/24926). Examples of beta-xylosidases that may be comprised in the composition of the invention include, but are not limited to, beta-xylosidases from *Neurospora crassa, Aspergillus fumigatus* and *Trichoderma reesei*. Examples of acetylxylan esterases that may be comprised in the enzyme composition include, but are not limited to, acetylxylan esterases from *Aspergillus aculeatus* (see WO 2010/108918), *Chaetomium globosum, Chaetomium gracile, Humicola insolens* DSM 1800 (see WO 2009/073709), *Hypocrea jecorina* (see WO 2005/001036), *Myceliophtera thermophila* (see WO 2010/014880), *Neurospora crassa, Phaeosphaeria nodorum* and *Thielavia terrestris* NRRL 8126 (see WO 2009/042846). In an embodiment the enzyme composition comprises an acetyl xylan esterase from *Rasamsonia*, such as *Rasamsonia emersonii* (see WO 2010/000888). Examples of feruloyl esterases (ferulic acid esterases) that may be comprised in the enzyme composition include, but are not limited to, feruloyl esterases form *Humicola insolens* DSM 1800 (see WO 2009/076122), *Neosartorya fischeri, Neurospora crassa, Penicillium aurantiogriseum* (see WO 2009/127729), and *Thielavia terrestris* (see WO 2010/053838 and WO 2010/065448). Examples of arabinofuranosidases that may be comprised in the enzyme composition include, but are not limited to, arabinofuranosidases from *Aspergillus niger, Humicola insolens* DSM 1800 (see WO 2006/114094 and WO 2009/073383) and *M. giganteus* (see WO 2006/114094). Examples of alpha-glucuronidases that may be comprised in the enzyme composition include, but are not limited to, alpha-glucuronidases from *Aspergillus clavatus, Aspergillus fumigatus, Aspergillus niger, Aspergillus terreus, Humicola insolens* (see WO 2010/014706), *Penicillium aurantiogriseum* (see WO 2009/068565) and *Trichoderma reesei*.

A composition of the current invention may comprise, in addition to one or more polypeptides of the invention, one, two, three, four classes or more of cellulase, for example one, two, three or four or all of a lytic polysaccharide monooxygenase (LPMO), an endoglucanase (EG), one or two exo-cellobiohydrolases (CBH) and a beta-glucosidase (BG). An enzyme composition of the current invention may comprise two or more of any of these classes of cellulase.

A composition of the current invention may comprise, in addition to one or more polypeptides of the invention, one type of cellulase activity and/or hemicellulase activity and/or pectinase activity provided by a composition as described herein and a second type of cellulase activity and/or hemicellulase activity and/or pectinase activity provided by an additional cellulase/hemicellulase/pectinase.

Accordingly, a composition of the current invention may comprise, in addition to one or more polypeptides of the invention, any cellulase, for example, a lytic polysaccharide monooxygenase, a cellobiohydrolase, an endo-β-1,4-glucanase, a beta-glucosidase or a β-(1,3)(1,4)-glucanase.

In an embodiment the enzyme composition as described herein comprises a polypeptide according to the invention, an endoglucanase, a cellobiohydrolase I, a cellobiohydrolase II, a beta-glucosidase, a beta-xylosidase and an endoxylanase.

As used herein, a cellobiohydrolase (EC 3.2.1.91) is any polypeptide which is capable of catalyzing the hydrolysis of 1,4-β-D-glucosidic linkages in cellulose or cellotetraose, releasing cellobiose from the ends of the chains. This enzyme may also be referred to as cellulase 1,4-β-cellobiosidase, 1,4-β-cellobiohydrolase, 1,4-β-D-glucan cellobiohydrolase, avicelase, exo-1,4-β-D-glucanase, exocellobiohydrolase or exoglucanase.

As used herein, an endo-β-1,4-glucanase (EC 3.2.1.4) is any polypeptide which is capable of catalyzing the endohydrolysis of 1,4-β-D-glucosidic linkages in cellulose, lichenin or cereal β-D-glucans. Such a polypeptide may also be capable of hydrolyzing 1,4-linkages in β-D-glucans also containing 1,3-linkages. This enzyme may also be referred to as cellulase, avicelase, β-1,4-endoglucan hydrolase, β-1,4-glucanase, carboxymethyl cellulase, celludextrinase, endo-1,4-β-D-glucanase, endo-1,4-β-D-glucanohydrolase, endo-1,4-β-glucanase or endoglucanase.

As used herein, a beta-glucosidase (EC 3.2.1.21) is any polypeptide which is capable of catalysing the hydrolysis of terminal, non-reducing β-D-glucose residues with release of β-D-glucose. Such a polypeptide may have a wide specificity for β-D-glucosides and may also hydrolyze one or more of the following: a β-D-galactoside, an α-L-arabinoside, a β-D-xyloside or a β-D-fucoside. This enzyme may also be referred to as amygdalase, β-D-glucoside glucohydrolase, cellobiase or gentobiase.

As used herein, a β-(1,3)(1,4)-glucanase (EC 3.2.1.73) is any polypeptide which is capable of catalysing the hydrolysis of 1,4-β-D-glucosidic linkages in β-D-glucans containing 1,3- and 1,4-bonds. Such a polypeptide may act on lichenin and cereal β-D-glucans, but not on β-D-glucans containing only 1,3- or 1,4-bonds. This enzyme may also be referred to as licheninase, 1,3-1,4-β-D-glucan 4-glucanohydrolase, β-glucanase, endo-β-1,3-1,4 glucanase, lichenase or mixed linkage β-glucanase. An alternative for this type of enzyme is EC 3.2.1.6, which is described as endo-1,3(4)-beta-glucanase. This type of enzyme hydrolyses 1,3- or 1,4-linkages in beta-D-glucanse when the glucose residue whose reducing group is involved in the linkage to be hydrolysed is itself substituted at C-3. Alternative names include endo-1,3-beta-glucanase, laminarinase, 1,3-(1,3;1,4)-beta-D-glucan 3 (4) glucanohydrolase. Substrates include laminarin, lichenin and cereal beta-D-glucans.

A composition of the current invention may comprise any hemicellulase, for example, an endoxylanase, a β-xylosidase, a α-L-arabinofuranosidase, an α-D-glucuronidase, an acetyl xylan esterase, a feruloyl esterase, a coumaroyl esterase, an α-galactosidase, a β-galactosidase, a β-mannanase or a β-mannosidase.

As used herein, an endoxylanase (EC 3.2.1.8) is any polypeptide which is capable of catalysing the endohydrolysis of 1,4-β-D-xylosidic linkages in xylans. This enzyme may also be referred to as endo-1,4-β-xylanase or 1,4-β-D-xylan xylanohydrolase. An alternative is EC 3.2.1.136, a glucuronoarabinoxylan endoxylanase, an enzyme that is able to hydrolyze 1,4 xylosidic linkages in glucuronoarabinoxylans.

As used herein, a β-xylosidase (EC 3.2.1.37) is any polypeptide which is capable of catalysing the hydrolysis of 1,4-β-D-xylans, to remove successive D-xylose residues from the non-reducing termini. Such enzymes may also hydrolyze xylobiose. This enzyme may also be referred to as xylan 1,4-β-xylosidase, 1,4-β-D-xylan xylohydrolase, exo-1,4-β-xylosidase or xylobiase. As used herein, an α-L-arabinofuranosidase (EC 3.2.1.55) is any polypeptide which is capable of acting on α-L-arabinofuranosides, α-L-arabinans containing (1,2) and/or (1,3)- and/or (1,5)-linkages, arabinoxylans and arabinogalactans. This enzyme may also be referred to as α-N-arabinofuranosidase, arabinofuranosidase or arabinosidase.

As used herein, an α-D-glucuronidase (EC 3.2.1.139) is any polypeptide which is capable of catalysing a reaction of the following form: alpha-D-glucuronoside+H$_2$)O=an alcohol+D-glucuronate. This enzyme may also be referred to as alpha-glucuronidase or alpha-glucosiduronase. These enzymes may also hydrolyse 4-O-methylated glucoronic acid, which can also be present as a substituent in xylans. An alternative is EC 3.2.1.131: xylan alpha-1,2-glucuronosidase, which catalyses the hydrolysis of alpha-1,2-(4-O-methyl)glucuronosyl links. As used herein, an acetyl xylan esterase (EC 3.1.1.72) is any polypeptide which is capable of catalysing the deacetylation of xylans and xylo-oligosaccharides. Such a polypeptide may catalyze the hydrolysis of acetyl groups from polymeric xylan, acetylated xylose, acetylated glucose, alpha-napthyl acetate or p-nitrophenyl acetate but, typically, not from triacetylglycerol. Such a polypeptide typically does not act on acetylated mannan or pectin.

As used herein, a feruloyl esterase (EC 3.1.1.73) is any polypeptide which is capable of catalysing a reaction of the form: feruloyl-saccharide+$H_2O$=ferulate+saccharide. The saccharide may be, for example, an oligosaccharide or a polysaccharide. It may typically catalyse the hydrolysis of the 4-hydroxy-3-methoxycinnamoyl (feruloyl) group from an esterified sugar, which is usually arabinose in 'natural' substrates. p-nitrophenol acetate and methyl ferulate are typically poorer substrates. This enzyme may also be referred to as cinnamoyl ester hydrolase, ferulic acid esterase or hydroxycinnamoyl esterase. It may also be referred to as a hemicellulase accessory enzyme, since it may help xylanases and pectinases to break down plant cell wall hemicellulose and pectin.

As used herein, a coumaroyl esterase (EC 3.1.1.73) is any polypeptide which is capable of catalysing a reaction of the form: coumaroyl-saccharide+H(2)O=coumarate+saccharide. The saccharide may be, for example, an oligosaccharide or a polysaccharide. This enzyme may also be referred to as trans-4-coumaroyl esterase, trans-p-coumaroyl esterase, p-coumaroyl esterase or p-coumaric acid esterase. This enzyme also falls within EC 3.1.1.73 so may also be referred to as a feruloyl esterase.

As used herein, an α-galactosidase (EC 3.2.1.22) is any polypeptide which is capable of catalysing the hydrolysis of terminal, non-reducing α-D-galactose residues in α-D-galactosides, including galactose oligosaccharides, galactomannans, galactans and arabinogalactans. Such a polypeptide may also be capable of hydrolyzing α-D-fucosides. This enzyme may also be referred to as melibiase.

As used herein, a β-galactosidase (EC 3.2.1.23) is any polypeptide which is capable of catalysing the hydrolysis of terminal non-reducing β-D-galactose residues in β-D-galactosides. Such a polypeptide may also be capable of hydrolyzing α-L-arabinosides. This enzyme may also be referred to as exo-(1->4)-β-D-galactanase or lactase.

As used herein, a β-mannanase (EC 3.2.1.78) is any polypeptide which is capable of catalysing the random hydrolysis of 1,4-β-D-mannosidic linkages in mannans, galactomannans and glucomannans. This enzyme may also be referred to as mannan endo-1,4-β-mannosidase or endo-1,4-mannanase.

As used herein, a β-mannosidase (EC 3.2.1.25) is any polypeptide which is capable of catalysing the hydrolysis of terminal, non-reducing β-D-mannose residues in β-D-mannosides. This enzyme may also be referred to as mannanase or mannase.

A composition of the current invention may comprise any pectinase, for example an endo-polygalacturonase, a pectin methyl esterase, an endo-galactanase, a beta galactosidase, a pectin acetyl esterase, an endo-pectin lyase, pectate lyase, alpha rhamnosidase, an exo-galacturonase, an expolygalacturonate lyase, a rhamnogalacturonan hydrolase, a rhamnogalacturonan lyase, a rhamnogalacturonan acetyl esterase, a rhamnogalacturonan galacturonohydrolase, a xylogalacturonase.

As used herein, an endo-polygalacturonase (EC 3.2.1.15) is any polypeptide which is capable of catalysing the random hydrolysis of 1,4-α-D-galactosiduronic linkages in pectate and other galacturonans. This enzyme may also be referred to as polygalacturonase pectin depolymerase, pectinase, endopolygalacturonase, pectolase, pectin hydrolase, pectin polygalacturonase, poly-α-1,4-galacturonide glycanohydrolase, endogalacturonase; endo-D-galacturonase or poly(1,4-α-D-galacturonide) glycanohydrolase.

As used herein, a pectin methyl esterase (EC 3.1.1.11) is any enzyme which is capable of catalysing the reaction: pectin+n $H_2O$=n methanol+pectate. The enzyme may also been known as pectinesterase, pectin demethoxylase, pectin methoxylase, pectin methylesterase, pectase, pectinoesterase or pectin pectylhydrolase.

As used herein, an endo-galactanase (EC 3.2.1.89) is any enzyme capable of catalysing the endohydrolysis of 1,4-β-D-galactosidic linkages in arabinogalactans. The enzyme may also be known as arabinogalactan endo-1,4-β-galactosidase, endo-1,4-β-galactanase, galactanase, arabinogalactanase or arabinogalactan 4-β-D-galactanohydrolase.

As used herein, a pectin acetyl esterase is defined herein as any enzyme which has an acetyl esterase activity which catalyses the deacetylation of the acetyl groups at the hydroxyl groups of GalUA residues of pectin.

As used herein, an endo-pectin lyase (EC 4.2.2.10) is any enzyme capable of catalysing the eliminative cleavage of (1→4)-α-D-galacturonan methyl ester to give oligosaccharides with 4-deoxy-6-O-methyl-α-D-galact-4-enuronosyl groups at their non-reducing ends. The enzyme may also be known as pectin lyase, pectin trans-eliminase; endo-pectin lyase, polymethylgalacturonic transeliminase, pectin methyltranseliminase, pectolyase, PL, PNL or PMGL or (1→4)-6-O-methyl-α-D-galacturonan lyase.

As used herein, a pectate lyase (EC 4.2.2.2) is any enzyme capable of catalysing the eliminative cleavage of (1→4)-α-D-galacturonan to give oligosaccharides with 4-deoxy-α-D-galact-4-enuronosyl groups at their non-reducing ends. The enzyme may also be known polygalacturonic transeliminase, pectic acid transeliminase, polygalacturonate lyase, endopectin methyltranseliminase, pectate transeliminase, endogalacturonate transeliminase, pectic acid lyase, pectic lyase, α-1,4-D-endopolygalacturonic acid lyase, PGA lyase, PPase-N, endo-α-1,4-polygalacturonic acid lyase, polygalacturonic acid lyase, pectin trans-eliminase, polygalacturonic acid trans-eliminase or (1→4)-α-D-galacturonan lyase.

As used herein, an alpha rhamnosidase (EC 3.2.1.40) is any polypeptide which is capable of catalysing the hydrolysis of terminal non-reducing α-L-rhamnose residues in α-L-rhamnosides or alternatively in rhamnogalacturonan. This enzyme may also be known as α-L-rhamnosidase T, α-L-rhamnosidase N or α-L-rhamnoside rhamnohydrolase.

As used herein, exo-galacturonase (EC 3.2.1.82) is any polypeptide capable of hydrolysis of pectic acid from the non-reducing end, releasing digalacturonate. The enzyme may also be known as exo-poly-α-galacturonosidase, exopolygalacturonosidase or exopolygalacturanosidase.

As used herein, exo-galacturonase (EC 3.2.1.67) is any polypeptide capable of catalysing: (1,4-α-D-galacturonide) $_{n+}H_2O$=(1,4-α-D-galacturonide)$_{n-1+}$D-galacturonate. The enzyme may also be known as galacturan 1,4-α-galacturonidase, exopolygalacturonase, poly(galacturonate) hydrolase, exo-D-galacturonase, exo-D-galacturonanase, exopoly-D-galacturonase or poly(1,4-α-D-galacturonide) galacturonohydrolase.

As used herein, exopolygalacturonate lyase (EC 4.2.2.9) is any polypeptide capable of catalysing eliminative cleavage of 4-(4-deoxy-α-D-galact-4-enuronosyl)-D-galacturonate from the reducing end of pectate, i.e. de-esterified pectin. This enzyme may be known as pectate disaccharide-lyase, pectate exo-lyase, exopectic acid transeliminase, exopectate lyase, exopolygalacturonic acid-trans-eliminase, PATE, exo-PATE, exo-PGL or (1→4)-α-D-galacturonan reducing-end-disaccharide-lyase.

As used herein, rhamnogalacturonan hydrolase is any polypeptide which is capable of hydrolyzing the linkage between galactosyluronic acid and rhamnopyranosyl in an endo-fashion in strictly alternating rhamnogalacturonan structures, consisting of the disaccharide [(1,2-alpha-L-rhamnoyl-(1,4)-alpha-galactosyluronic acid].

As used herein, rhamnogalacturonan lyase is any polypeptide which is any polypeptide which is capable of cleaving α-L-Rhap-(1→4)-α-D-GalpA linkages in an endo-fashion in rhamnogalacturonan by beta-elimination.

As used herein, rhamnogalacturonan acetyl esterase is any polypeptide which catalyses the deacetylation of the backbone of alternating rhamnose and galacturonic acid residues in rhamnogalacturonan.

As used herein, rhamnogalacturonan galacturonohydrolase is any polypeptide which is capable of hydrolyzing galacturonic acid from the non-reducing end of strictly alternating rhamnogalacturonan structures in an exo-fashion.

As used herein, xylogalacturonase is any polypeptide which acts on xylogalacturonan by cleaving the β-xylose substituted galacturonic acid backbone in an endo-manner. This enzyme may also be known as xylogalacturonan hydrolase.

As used herein, endo-arabinanase (EC 3.2.1.99) is any polypeptide which is capable of catalysing endohydrolysis of 1,5-α-arabinofuranosidic linkages in 1,5-arabinans. The enzyme may also be known as endo-arabinase, arabinan endo-1,5-α-L-arabinosidase, endo-1,5-α-L-arabinanase, endo-α-1,5-arabanase; endo-arabanase or 1,5-α-L-arabinan 1,5-α-L-arabinanohydrolase.

A composition of the current invention will typically comprise at least two cellulases, at least one of which may be a polypeptide of the invention, and optionally at least one hemicellulase and optionally at least one pectinase. An enzyme composition of the current invention may comprise a lytic polysaccharide monooxygenases, a cellobiohydrolase, an endoglucanase and/or a beta-glucosidase. Such an enzyme composition may also comprise one or more hemicellulases and/or one or more pectinases.

In addition, one or more (for example two, three, four or all) of an amylase, a protease, a lipase, a ligninase, a hexosyltransferase, a glucuronidase, an expansin, a cellulose induced protein or a cellulose integrating protein or like protein may be present in a composition of the current invention.

"Protease" includes enzymes that hydrolyze peptide bonds (peptidases), as well as enzymes that hydrolyze bonds between peptides and other moieties, such as sugars (glycopeptidases). Many proteases are characterized under EC 3.4 and are suitable for use in the processes of the current invention. Some specific types of proteases include, cysteine proteases including pepsin, papain and serine proteases including chymotrypsins, carboxypeptidases and metalloendopeptidases.

"Lipase" includes enzymes that hydrolyze lipids, fatty acids, and acylglycerides, including phospoglycerides, lipoproteins, diacylglycerols, and the like. In plants, lipids are used as structural components to limit water loss and pathogen infection. These lipids include waxes derived from fatty acids, as well as cutin and suberin.

"Ligninese" includes enzymes that can hydrolyze or break down the structure of lignin polymers. Enzymes that can break down lignin include lignin peroxidases, manganese peroxidases, laccases and feruloyl esterases, and other enzymes described in the art known to depolymerize or otherwise break lignin polymers. Also included are enzymes capable of hydrolyzing bonds formed between hemicellulosic sugars (notably arabinose) and lignin. Ligninases include but are not limited to the following group of enzymes: lignin peroxidases (EC 1.11.1.14), manganese peroxidases (EC 1.11.1.13), laccases (EC 1.10.3.2) and feruloyl esterases (EC 3.1.1.73).

"Hexosyltransferase" (2.4.1-) includes enzymes which are capable of catalysing a transferase reaction, but which can also catalyze a hydrolysis reaction, for example of cellulose and/or cellulose degradation products. An example of a hexosyltransferase which may be used in the invention is a f3-glucanosyltransferase. Such an enzyme may be able to catalyze degradation of (1,3)(1,4)glucan and/or cellulose and/or a cellulose degradation product.

"Glucuronidase" includes enzymes that catalyze the hydrolysis of a glucoronoside, for example β-glucuronoside to yield an alcohol. Many glucuronidases have been characterized and may be suitable for use in the invention, for example β-glucuronidase (EC 3.2.1.31), hyalurono-glucuronidase (EC 3.2.1.36), glucuronosyl-disulfoglucosamine glucuronidase (3.2.1.56), glycyrrhizinate β-glucuronidase (3.2.1.128) or α-D-glucuronidase (EC 3.2.1.139).

A composition of the current invention may comprise an expansin or expansin-like protein, such as a swollenin (see Salheimo et al., Eur. J. Biochem. 269, 4202-4211, 2002) or a swollenin-like protein.

Expansins are implicated in loosening of the cell wall structure during plant cell growth. Expansins have been proposed to disrupt hydrogen bonding between cellulose and other cell wall polysaccharides without having hydrolytic activity. In this way, they are thought to allow the sliding of cellulose fibers and enlargement of the cell wall. Swollenin, an expansin-like protein contains an N-terminal Carbohydrate Binding Module Family 1 domain (CBD) and a C-terminal expansin-like domain. For the purposes of this invention, an expansin-like protein or swollenin-like protein may comprise one or both of such domains and/or may disrupt the structure of cell walls (such as disrupting cellulose structure), optionally without producing detectable amounts of reducing sugars.

A composition of the current invention may comprise a cellulose induced protein, for example the polypeptide product of the cip1 or cip2 gene or similar genes (see Foreman et al., J. Biol. Chem. 278(34), 31988-31997, 2003), a cellulose/cellulosome integrating protein, for example the polypeptide product of the cipA or cipC gene, or a scaffoldin or a scaffoldin-like protein. Scaffoldins and cellulose integrating proteins are multi-functional integrating subunits which may organize cellulolytic subunits into a multi-enzyme complex. This is accomplished by the interaction of two complementary classes of domain, i.e. a cohesion domain on scaffoldin and a dockerin domain on each enzymatic unit. The scaffoldin subunit also bears a cellulose-binding module (CBM) that mediates attachment of the cellulosome to its substrate. A scaffoldin or cellulose integrating protein for the purposes of this invention may comprise one or both of such domains.

A composition of the current invention may also comprise a catalase. The term "catalase" means a hydrogen-peroxide:hydrogen-peroxide oxidoreductase (EC 1.11.1.6 or EC 1.11.1.21) that catalyzes the conversion of two hydrogen peroxides to oxygen and two waters. Catalase activity can be determined by monitoring the degradation of hydrogen peroxide at 240 nm based on the following reaction: $2H_2O_2 \rightarrow 2H_2O+O_2$. The reaction is conducted in 50 mM phosphate pH 7.0 at 25° C. with 10.3 mM substrate ($H_2O_2$) and approximately 100 units of enzyme per ml. Absorbance is monitored spectrophotometrically within 16-24 seconds, which should correspond to an absorbance reduction from 0.45 to 0.4. One catalase activity unit can be expressed as one micromole of $H_2O_2$ degraded per minute at pH 7.0 and 25° C.

A composition of the current invention may also comprise an amylase. The term "amylase" as used herein means enzymes that hydrolyze alpha-1,4-glucosidic linkages in starch, both in amylose and amylopectin, such as alpha-amylase (EC 3.2.1.1), beta-amylase (EC 3.2.1.2), glucan 1,4-alpha-glucosidase (EC 3.2.1.3), glucan 1,4-alpha-maltotetraohydrolase (EC 3.2.1.60), glucan 1,4-alpha-maltohexaosidase (EC 3.2.1.98), glucan 1,4-alpha-maltotriohydrolase (EC 3.2.1.116) and glucan 1,4-alpha-maltohydrolase (EC 3.2.1.133), and enzymes that hydrolyze alpha-1,6-glucosidic linkages, being the branch-points in amylopectin, such as pullulanase (EC 3.2.1.41) and limit dextinase (EC 3.2.1.142).

A composition of the current invention may be composed of a member of each of the classes of enzymes mentioned above, several members of one enzyme class, or any combination of these enzymes classes or helper proteins (i.e. those proteins mentioned herein which do not have enzymatic activity per se, but do nevertheless assist in lignocellulosic degradation).

A composition of the current invention may be composed of enzymes from (1) commercial suppliers; (2) cloned genes expressing enzymes; (3) broth (such as that resulting from growth of a microbial strain in media, wherein the strains secrete proteins and enzymes into the media; (4) cell lysates of strains grown as in (3); and/or (5) plant material expressing enzymes. Different enzymes in a composition of the invention may be obtained from different sources.

In the uses and processes described herein, the components of the compositions described above may be provided concomitantly (i.e. as a single composition per se) or separately or sequentially.

The enzymes can be produced either exogenously in microorganisms, yeasts, fungi, bacteria or plants, then isolated and added, for example, to lignocellulosic material. Alternatively, the enzyme may be produced in a fermentation that uses (pretreated) lignocellulosic material (such as corn stover or wheat straw) to provide nutrition to an organism that produces an enzyme(s). In this manner, plants that produce the enzymes may themselves serve as a lignocellulosic material and be added into lignocellulosic material.

In an embodiment the composition is a whole fermentation broth. In an embodiment the composition is in the form of a whole fermentation broth of a fungus, preferably *Rasamsonia*. The whole fermentation broth can be prepared from fermentation of recombinant filamentous fungi. In an embodiment the filamentous fungus is a recombinant filamentous fungus comprising one or more genes which can be homologous or heterologous to the filamentous fungus. In an embodiment, the filamentous fungus is a recombinant filamentous fungus comprising one or more genes which can be homologous or heterologous to the filamentous fungus wherein the one or more genes encode enzymes that can degrade a cellulosic substrate. The whole fermentation broth may comprise any of the polypeptides described above or any combination thereof.

Preferably, the composition is a whole fermentation broth wherein the cells are killed. The whole fermentation broth may contain organic acid(s) (used for killing the cells), killed cells and/or cell debris, and culture medium.

Generally, the filamentous fungi is cultivated in a cell culture medium suitable for production of at least a polypeptide of the invention and preferably one or more enzymes capable of hydrolyzing a cellulosic substrate. The cultivation takes place in a suitable nutrient medium comprising carbon and nitrogen sources and inorganic salts, using procedures known in the art. Suitable culture media, temperature ranges and other conditions suitable for growth and expression of a polypeptide of the invention and, optionally, cellulase and/or hemicellulase and/or pectinase production are known in the art. The whole fermentation broth can be prepared by growing the filamentous fungi to stationary phase and maintaining the filamentous fungi under limiting carbon conditions for a period of time sufficient to express a polypeptide of the invention and/or one or more cellulases and/or hemicellulases and/or pectinases. Once enzymes, such as the polypeptide of the invention and/or cellulases and/or hemicellulases and/or pectinases, are secreted by the filamentous fungi into the fermentation medium, the whole fermentation broth can be used. The whole fermentation broth of the present invention may comprise filamentous fungi. In some embodiments, the whole fermentation broth comprises the unfractionated contents of the fermentation materials derived at the end of the fermentation. Typically, the whole fermentation broth comprises the spent culture medium and cell debris present after the filamentous fungi is grown to saturation, incubated under carbon-limiting conditions to allow protein synthesis (particularly, expression of cellulases and/or hemicellulases and/or pectinases). In some embodiments, the whole fermentation broth comprises the spent cell culture medium, extracellular enzymes and filamentous fungi. In some embodiments, the filamentous fungi present in whole fermentation broth can be lysed, permeabilized, or killed using methods known in the art to produce a cell-killed whole fermentation broth. In an embodiment, the whole fermentation broth is a cell-killed whole fermentation broth, wherein the whole fermentation broth containing the filamentous fungi cells are lysed or killed. In some embodiments, the cells are killed by lysing the filamentous fungi by chemical and/or pH treatment to generate the cell-killed whole broth of a fermentation of the filamentous fungi. In some embodiments, the cells are killed by lysing the filamentous fungi by chemical and/or pH treatment and adjusting the pH of the cell-killed fermentation mix to a suitable pH. In an embodiment, the whole fermentation broth comprises a first organic acid component comprising at least one 1-5 carbon organic acid and/or a salt thereof and a second organic acid component comprising at least 6 or more carbon organic acid and/or a salt thereof. In an embodiment, the first organic acid component is acetic acid, formic acid, propionic acid, a salt thereof, or any combination thereof and the second organic acid component is benzoic acid, cyclohexanecarboxylic acid, 4-methylvaleric acid, phenylacetic acid, a salt thereof, or any combination thereof.

The term "whole fermentation broth" as used herein refers to a preparation produced by cellular fermentation that undergoes no or minimal recovery and/or purification. For example, whole fermentation broths are produced when microbial cultures are grown to saturation, incubated under carbon-limiting conditions to allow protein synthesis (e.g., expression of enzymes by host cells) and secretion into cell culture medium. Typically, the whole fermentation broth is unfractionated and comprises spent cell culture medium, extracellular enzymes, and microbial, preferably non-viable, cells.

If needed, the whole fermentation broth can be fractionated and the one or more of the fractionated contents can be used. For instance, the killed cells and/or cell debris can be removed from a whole fermentation broth to provide a composition that is free of these components.

The whole fermentation broth may further comprise a preservative and/or anti-microbial agent. Such preservatives and/or agents are known in the art.

The whole fermentation broth as described herein is typically a liquid, but may contain insoluble components, such as killed cells, cell debris, culture media components, and/or insoluble enzyme(s). In some embodiments, insoluble components may be removed to provide a clarified whole fermentation broth.

In an embodiment, the whole fermentation broth may be supplemented with one or more enzyme activities that are not expressed endogenously, or expressed at relatively low level by the filamentous fungi, to improve the degradation of the cellulosic substrate, for example, to fermentable sugars such as glucose or xylose. The supplemental enzyme(s) can be added as a supplement to the whole fermentation broth and the enzymes may be a component of a separate whole fermentation broth, or may be purified, or minimally recovered and/or purified.

In an embodiment, the whole fermentation broth comprises a whole fermentation broth of a fermentation of recombinant filamentous fungi overexpressing one or more enzymes to improve the degradation of the cellulosic substrate. Alternatively, the whole fermentation broth can comprise a mixture of a whole fermentation broth of a fermentation of a non-recombinant filamentous fungus and a recombinant filamentous fungus overexpressing one or more enzymes to improve the degradation of the cellulosic substrate. In an embodiment, the whole fermentation broth comprises a whole fermentation broth of a fermentation of filamentous fungi overexpressing a polypeptide of the invention. In an embodiment, the whole fermentation broth comprises a whole fermentation broth of a fermentation of filamentous fungi overexpressing a beta-glucosidase. Alternatively, the whole fermentation broth for use in the present methods and reactive compositions can comprise a mixture of a whole fermentation broth of a fermentation of a non-recombinant filamentous fungus and a whole fermentation broth of a fermentation of recombinant filamentous fungi overexpressing a polypeptide of the invention and/or a beta-glucosidase.

Polynucleotide Sequence

The invention relates to a polynucleotide, wherein the polynucleotide comprises a nucleotide sequence that is selected from the group consisting of (a) a nucleotide sequence having at least 60% sequence identity with the nucleotide sequence of SEQ ID NO: 3, 6, 9, 12, 15, 18, 21, 24, 27, 30, 33, 36, 39, 42, 45 and/or 48, (b) a nucleotide sequence which hybridises under at least high stringency conditions with the complementary strand of SEQ ID NO: 3, 6, 9, 12, 15, 18, 21, 24, 27, 30, 33, 36, 39, 42, 45 and/or 48, (c) a fragment which is at least 100 nucleotides in length of a nucleotide sequence as defined in (a) or (b), (d) a nucleotide sequence which is degenerate as a result of the genetic code to a nucleotide sequence as defined in any one of (a), (b), or (c), and (e) a nucleotide sequence which is the complement of a nucleotide sequence as defined in (a), (b), (c), or (d).

In an embodiment the polynucleotide encodes a polypeptide according to the invention. In an embodiment the polynucleotide of the present invention is isolated.

In an embodiment the polynucleotide of the invention comprises a nucleotide sequence having at least 60% sequence identity with the nucleotide sequence of SEQ ID NO: 3, 6, 9, 12, 15, 18, 21, 24, 27, 30, 33, 36, 39, 42, 45 and/or 48. In an embodiment the polynucleotide of the invention comprises a nucleotide sequence having at least 65% sequence identity, at least 70% sequence identity, at least 75% sequence identity, at least 76% sequence identity, at least 77% sequence identity, at least 78% sequence identity, at least 79% sequence identity, at least 80% sequence identity, at least 81% sequence identity, at least 82% sequence identity, at least 83% sequence identity, at least 84% sequence identity, at least 85% sequence identity, at least 86% sequence identity, at least 87% sequence identity, at least 88% sequence identity, at least 89% sequence identity, at least 90% sequence identity, at least 91% sequence identity, at least 92% sequence identity, at least 93% sequence identity, at least 94% sequence identity, at least 95% sequence identity, at least 96% sequence identity, at least 97% sequence identity, at least 98% sequence identity, at least 99% sequence identity, with the nucleotide sequence of SEQ ID NO: 3, 6, 9, 12, 15, 18, 21, 24, 27, 30, 33, 36, 39, 42, 45 and/or 48. In an embodiment the polynucleotide of the invention comprises or consists of the nucleotide sequence of SEQ ID NO: 3, 6, 9, 12, 15, 18, 21, 24, 27, 30, 33, 36, 39, 42, 45 or 48.

The invention also relates to a polynucleotide comprising a nucleotide sequence which encodes at least one functional domain of a polypeptide according to SEQ ID NO: 1, 4, 7, 10, 13, 16, 19, 22, 25, 28, 31, 34, 37, 40, 43 and/or 46 or SEQ ID NO: 2, 5, 8, 11, 14, 17, 20, 23, 26, 29, 32, 35, 38, 41, 44 and/or 47 or a variant thereof, such as a functional equivalent, or a fragment of either thereof.

A polynucleotide of the present invention, such as a polynucleotide having the nucleotide sequence of SEQ ID NO: 3, 6, 9, 12, 15, 18, 21, 24, 27, 30, 33, 36, 39, 42, 45 or 48 can be isolated using standard molecular biology techniques and the sequence information provided herein. For example, using all or a portion of the nucleotide sequence of SEQ ID NO: 3, 6, 9, 12, 15, 18, 21, 24, 27, 30, 33, 36, 39, 42, 45 or 48 as a hybridization probe, polynucleotides according to the invention can be isolated using standard hybridization and cloning techniques (e.g., as described in Sambrook, J., Fritsh, E. F., and Maniatis, T. Molecular Cloning: A Laboratory Manual.2nd, ed., Cold Spring Harbor Laboratory, Cold Spring Harbor Laboratory Press, Cold Spring Harbor, N.Y., 1989).

Moreover, a polynucleotide encompassing all or a portion of SEQ ID NO: 3, 6, 9, 12, 15, 18, 21, 24, 27, 30, 33, 36, 39, 42, 45 or 48 may be isolated by the polymerase chain reaction (PCR) using synthetic oligonucleotide primers designed based upon the sequence information contained in SEQ ID NO: 3, 6, 9, 12, 15, 18, 21, 24, 27, 30, 33, 36, 39, 42, 45 or 48.

A polynucleotide of the invention can be amplified using cDNA, mRNA or alternatively, genomic DNA, as a template and appropriate oligonucleotide primers according to standard PCR amplification techniques. The polynucleotide so amplified can be cloned into an appropriate vector and characterized by DNA sequence analysis.

Furthermore, oligonucleotides corresponding to or hybridizing to a nucleotide sequence according to the invention can be prepared by standard synthetic techniques, e.g. using an automated DNA synthesizer.

In a preferred embodiment, an isolated polynucleotide of the invention comprises the nucleotide sequence shown in SEQ ID NO: 3, 6, 9, 12, 15, 18, 21, 24, 27, 30, 33, 36, 39, 42, 45 or 48.

In another preferred embodiment, an isolated polynucleotide of the invention comprises a polynucleotide which is the reverse complement of the nucleotide sequence shown in SEQ ID NO: 3, 6, 9, 12, 15, 18, 21, 24, 27, 30, 33, 36, 39, 42, 45 or 48.

A polynucleotide which is complementary to a nucleotide sequence is one which is sufficiently complementary to the other nucleotide sequence such that it can hybridize to the other nucleotide sequence thereby forming a stable duplex. The term "cDNA" (complementary DNA) is defined herein as a DNA molecule which can be prepared by reverse transcription from a mRNA molecule. cDNA derived from mRNA only contains coding sequences and can be directly translated into the corresponding polypeptide product. The term "complementary strand" can be used interchangeably with the term "complement". The complement of a nucleotide strand can be the complement of a coding strand or the complement of a non-coding strand. When referring to double-stranded polynucleotides, the complement of a polynucleotide encoding a polypeptide refers to the complementary strand of the strand encoding the amino acid sequence or to any polynucleotide containing the same.

As used herein, the term "hybridization" means the pairing of substantially complementary strands of oligomeric compounds. One mechanism of pairing involves hydrogen bonding, which may be Watson-Crick, Hoogsteen or reversed Hoogsteen hydrogen bonding, between complementary nucleotide bases (nucleotides) of the strands of oligomeric compounds. For example, adenine and thymine are complementary nucleic acids which pair through the formation of hydrogen bonds. Hybridization can occur under varying circumstances. "Stringency hybridization" or "hybridizes under low stringency, medium stringency, high stringency, or very high stringency conditions" is used herein to describe conditions for hybridization and washing, more specifically conditions under which an oligomeric compound will hybridize to its target sequence, but to a minimal number of other sequences. So, the oligomeric compound will hybridize to the target sequence to a detectably greater degree than to other sequences. Guidance for performing hybridization reactions can be found in Current Protocols in Molecular Biology, John Wiley & Sons, N.Y. (1989), 6.3.1-6:3.6. Aqueous and non-aqueous methods are described in that reference and either can be used. Stringency conditions are sequence-dependent and will be different in different circumstances. Generally, stringency conditions are selected to be about 5° C. lower than the thermal melting point (Tm) for the oligomeric compound at a defined ionic strength and pH. The Tm is the temperature (under defined ionic strength and pH) at which 50% of an oligomeric compound hybridizes to a perfectly matched probe. Stringency conditions may also be achieved with the addition of destabilizing agents such as formamide.

Examples of specific hybridization conditions are as follows: 1) low stringency hybridization conditions in 6× sodium chloride/sodium citrate (SSC) at about 45° C., followed by two washes in 0.2×SSC, 0.1% SDS at least at 50° C. (the temperature of the washes can be increased to 55° C. for low stringency conditions); 2) medium stringency hybridization conditions in 6×SSC at about 45° C., followed by one or more washes in 0.2×SSC, 0.1% SDS at 60° C.; 3) high stringency hybridization conditions in 6×SSC at about 45° C., followed by one or more washes in 0.2×SSC, 0.1% SDS at 65° C.; and 4) very high stringency hybridization conditions are 0.5M sodium phosphate, 7% SDS at 65° C., followed by one or more washes at 0.2×SSC, 1% SDS at 65° C.

In general, high stringency conditions, such as high hybridization temperature and optionally low salt concentrations, permit only hybridization between sequences that are highly similar, whereas low stringency conditions, such as low hybridization temperature and optionally high salt concentrations, allow hybridization when the sequences are less similar.

One aspect of the invention pertains to isolated polynucleotides that encode a polypeptide of the invention as well as polynucleotides sufficient for use as hybridization probes to identify polynucleotides encoding a polypeptide of the invention.

The term "naturally-occurring" as used herein refers to processes, events, or things that occur in their relevant form in nature. By contrast, "not naturally-occurring" refers to processes, events, or things whose existence or form involves the hand of man. Generally, the term "naturally-occurring" with regard to polypeptides or polynucleotides can be used interchangeable with the term "wild-type" or "native". It refers to polypeptide or polynucleotides encoding a polypeptide, having an amino acid sequence or nucleotide sequence, respectively, identical to that found in nature. Naturally occurring polypeptides include native polypeptides, such as those polypeptides naturally expressed or found in a particular host. Naturally occurring polynucleotides include native polynucleotides such as those polynucleotides naturally found in the genome of a particular host. Additionally, a sequence that is wild-type or naturally-occurring may refer to a sequence from which a variant or a synthetic sequence is derived.

The polypeptides of the present invention and the polynucleotides of the present invention are not naturally-occurring.

As used herein, a "synthetic" molecule is produced by in vitro chemical or enzymatic synthesis. It includes, but is not limited to, polynucleotides made with optimal codon usage for host organisms of choice.

The term "recombinant" when used in reference to a cell, polynucleotide, polypeptide or vector, indicates that the cell, polynucleotide, polypeptide or vector, has been modified by the introduction of a heterologous polynucleotide or polypeptide or the alteration of a native polynucleotide or polypeptide, or that the cell is derived from a cell so modified. Thus, for example, recombinant cells express polynucleotides that are not found within the native (non-recombinant) form of the cell or express native genes that are otherwise abnormally expressed, under expressed or not expressed at all. The term "recombinant" is synonymous with "genetically modified".

The term "isolated polypeptide" as used herein means a polypeptide that is removed from at least one component, e.g. other polypeptide material, with which it is naturally associated. Thus, an isolated polypeptide may contain at most 10%, at most 8%, more preferably at most 6%, more preferably at most 5%, more preferably at most 4%, more preferably at most 3%, even more preferably at most 2%, even more preferably at most 1% and most preferably at most 0.5% as determined by SDS-PAGE of other polypeptide material with which it is natively associated. The isolated polypeptide may be free of any other impurities. The isolated polypeptide may be at least 50% pure, at least 60% pure, at least 70% pure, at least 75% pure, at least 80% pure, at least 85% pure, at least 90% pure, at least 95% pure, at least 96% pure, at least 97% pure, at least 98% pure, at least 99% pure, at least 99.5% pure, at least 99.9% pure as determined by SDS-PAGE or any other analytical method suitable for this purpose and known to the person skilled in the art.

An "isolated polynucleotide" or "isolated nucleic acid" is a polynucleotide removed from other polynucleotides with which it is naturally associated. Thus, an isolated polynucleotide may contain at most 10%, at most 8%, more preferably at most 6%, more preferably at most 5%, more preferably at most 4%, more preferably at most 3%, even more preferably at most 2%, even more preferably at most 1% and most preferably at most 0.5% by weight of other polynucleotide material with which it is naturally associated. The isolated polynucleotide may be free of any other impurities. The isolated polynucleotide may be at least 50% pure, at least 60% pure, at least 70% pure, at least 75% pure, at least 80% pure, at least 85% pure, at least 90% pure, or at least 95% pure, at least 96% pure, at least 97% pure, at least 98% pure, at least 99% pure, at least 99.5% pure, at least 99.9% pure by weight.

The term "substantially pure" with regard to polypeptides refers to a polypeptide preparation which contains at the most 50% by weight of other polypeptide material. The polypeptides disclosed herein are preferably in a substantially pure form. In particular, it is preferred that the polypeptides disclosed herein are in "essentially pure form", i.e. that the polypeptide preparation is essentially free of other polypeptide material. Optionally, the polypeptide may also be essentially free of non-polypeptide material such as nucleic acids, lipids, media components, and the like. Herein, the term "substantially pure polypeptide" is synonymous with the terms "isolated polypeptide" and "polypeptide in isolated form". The term "substantially pure" with regard to polynucleotide refers to a polynucleotide preparation which contains at the most 50% by weight of other polynucleotide material. The polynucleotides disclosed herein are preferably in a substantially pure form. In particular, it is preferred that the polynucleotide disclosed herein are in "essentially pure form", i.e. that the polynucleotide preparation is essentially free of other polynucleotide material. Optionally, the polynucleotide may also be essentially free of non-polynucleotide material such as polypeptides, lipids, media components, and the like. Herein, the term "substantially pure polynucleotide" is synonymous with the terms "isolated polynucleotide" and "polynucleotide in isolated form".

The term "nucleic acid" as used in the present invention refers to a nucleotide polymer including at least 5 nucleotide units. A nucleic acid refers to a ribonucleotide polymer (RNA), deoxynucleotide polymer (DNA) or a modified form of either type of nucleic acid or synthetic form thereof or mixed polymers of any of the above. Nucleic acids may include either or both naturally-occurring and modified nucleic acids linked together by naturally-occurring and/or non-naturally occurring nucleic acid linkages. The nucleic acid molecules may be modified chemically or biochemically or may contain non-natural or derivatized nucleic acid bases, as will be readily appreciated by those of skill in the art. Such modifications include, for example, labels, methylation, substitution of one or more of the naturally occurring nucleic acids with an analog, internucleotide modifications such as uncharged linkages (e.g., methyl phosphonates, phosphotriesters, phosphoramidates, carbamates, etc.), charged linkages (e.g., phosphorothioates, phosphorodithioates, etc.), pendent moieties (e.g., polypeptides), intercalators (e.g., acridine, psoralen, etc.), chelators, alkylators, and modified linkages (e.g., alpha anomeric nucleic acids, etc.) The term nucleic acid is also intended to include any topological conformation, including single-stranded (sense strand and antisense strand), double-stranded, partially duplexed, triplex, hairpinned, circular and padlocked conformations. Also included are synthetic molecules that mimic nucleic acids in their ability to bind to a designated sequence via hydrogen bonding and other chemical interactions. Such molecules are known in the art and include, for example, those in which peptide linkages substitute for phosphate linkages in the backbone of the molecule. A reference to a nucleic acid sequence encompasses its complement unless otherwise specified. Thus, a reference to a nucleic acid molecule having a particular sequence should be understood to encompass its complementary strand, with its complementary sequence. The complementary strand is also useful, e.g., for antisense therapy, hybridization probes and PCR primers. The term "nucleic acid", "nucleic acid molecule" and "polynucleotide" can be used interchangeably herein. The term "nucleic acid sequence" and "nucleotide sequence" can also be used interchangeably herein.

A "substitution", as used herein in relation to polypeptides or polynucleotides, denotes the replacement of one or more amino acids in a polypeptide sequence or of one or more nucleotides in a nucleotide sequence, respectively, by different amino acids or nucleotides, respectively.

Another embodiment of the invention provides an isolated polynucleotide which is antisense to a polynucleotide according to the invention, e.g. the coding strand of a polynucleotide of the present invention. Also included within the scope of the invention are the complementary strands of the polynucleotides described herein.

Unless otherwise indicated, all nucleotide sequences determined by sequencing a DNA molecule herein were determined using an automated DNA sequencer and all amino acid sequences of polypeptides encoded by DNA molecules determined herein were predicted by translation of a DNA sequence determined as above. Therefore, as is known in the art for any DNA sequence determined by this automated approach, any nucleotide sequence determined herein may contain some errors. Nucleotide sequences determined by automation are typically at least about 90% identical, more typically at least about 95% to at least about 99.9% identical to the actual nucleotide sequence of the sequenced DNA molecule.

The actual sequence can be more precisely determined by other approaches including manual DNA sequencing methods well known in the art. As is also known in the art, a single insertion or deletion in a determined nucleotide sequence compared to the actual sequence will cause a frame shift in translation of the nucleotide sequence such that the predicted amino acid sequence encoded by a determined nucleotide sequence will be completely different from the amino acid sequence actually encoded by the sequenced DNA molecule, beginning at the point of such an insertion or deletion.

The term "deletion" as used herein denotes a change in either amino acid or nucleotide sequence in which one or more amino acids or nucleotides, respectively, are absent as compared to the parent, often the naturally-occurring, amino acid or nucleotide sequence.

The term "insertion", also known as the term "addition", denotes a change in an amino acid or nucleotide sequence resulting in the addition of one or more amino acids or nucleotides, respectively, as compared to the parent, often the naturally-occurring, amino acid or nucleotide sequence.

A person skilled in the art is capable of identifying such erroneously identified bases and knows how to correct for such errors, for example by sequencing the relevant gene.

A polynucleotide according to the invention may comprise only a portion or a fragment of the nucleotide sequence shown in SEQ ID NO: 3, 6, 9, 12, 15, 18, 21, 24, 27, 30, 33, 36, 39, 42, 45 or 48, for example a fragment which can be used as a probe or primer or a fragment encoding a portion of a polypeptide according to the invention.

The probe/primer typically comprises a substantially purified oligonucleotide which typically comprises a nucleotide sequence that hybridizes preferably under highly stringent conditions to at least from about 12 to about 15, preferably from about 18 to about 20, preferably from about 22 to about 25, more preferably about 30, about 35, about 40, about 45, about 50, about 55, about 60, about 65, or about 75 or more consecutive nucleotides of the nucleotide sequence shown in SEQ ID NO: 3, 6, 9, 12, 15, 18, 21, 24, 27, 30, 33, 36, 39, 42, 45 or 48.

Probes can be used to detect nucleotide sequences encoding the same or homologous polypeptides, for instance in other organisms. In preferred embodiments, the probe further comprises a label group attached thereto, e.g. the label group can be a radioisotope, a fluorescent compound, an enzyme, or an enzyme cofactor. Such probes can also be used as part of a diagnostic test kit for identifying cells which express a polypeptide according to the invention.

The polynucleotides may be synthetic polynucleotides. The synthetic polynucleotides may be optimized in codon use, preferably according to the methods described in WO 2006/077258 and/or PCT/EP2007/055943, which are herein incorporated by reference. PCT/EP2007/055943 addresses codon-pair optimization. Codon-pair optimization is a method wherein the nucleotide sequences encoding a polypeptide have been modified with respect to their codon usage, in particular the codon pairs that are used, to obtain improved expression of the nucleotide sequence encoding the polypeptide and/or improved production of the encoded polypeptide. Codon pairs are defined as a set of two subsequent triplets (codons) in a coding sequence. Those skilled in the art will know that the codon usage needs to be adapted depending on the host species, possibly resulting in variants with significant homology deviation from SEQ ID NO: 3, 6, 9, 12, 15, 18, 21, 24, 27, 30, 33, 36, 39, 42, 45 and/or 48, but still encoding the polypeptide of the invention.

The term "expression" includes any step involved in the production of the polypeptide including, but not limited to, transcription, post-transcriptional modification, translation, post-translational modification, and secretion.

Nucleic Acid Construct

The invention further relates to a nucleic acid construct comprising the polynucleotide of the present invention. The term "nucleic acid construct" is herein referred to as a nucleic acid molecule, either single- or double-stranded, which is isolated from a naturally-occurring gene or which has been modified to contain segments of nucleic acids which are combined and juxtaposed in a manner which would not otherwise exist in nature. The term nucleic acid construct is synonymous with the term "expression cassette" when the nucleic acid construct contains all the control sequences required for expression of a coding sequence, wherein said control sequences are operably linked to said coding sequence.

The term "coding sequence" as defined herein is a sequence, which is transcribed into mRNA and translated into a polypeptide. The boundaries of the coding sequence are generally determined by the ATG start codon at the 5'-end of the mRNA and a translation stop codon sequence terminating the open reading frame at the 3'-end of the mRNA. A coding sequence can include, but is not limited to, DNA, cDNA, and recombinant nucleotide sequences. Preferably, the nucleic acid has high GC content. The GC content herein indicates the number of G and C nucleotides in the construct, divided by the total number of nucleotides, expressed in %. The GC content is preferably 56% or more, 57% or more, 58% or more, 59% or more, 60% or more, or in the range of 56-70% or the range of 58-65%. Preferably, the nucleic acid construct comprises a promoter sequence, a coding sequence in operative association with said promoter sequence and control sequences, such as (a) a translational termination sequence orientated in 5' towards 3' direction, and/or (b) a translational initiator coding sequence orientated in 5' towards 3' direction, and/or (c) a translational initiator sequence In the context of this invention, the term "translational initiator coding sequence" is defined as the nucleotides immediately downstream of the initiator or start codon of the open reading frame of a coding sequence. The initiator or start codon encodes for the AA methionine. The initiator codon is typically ATG, but may also be any functional start codon such as GTG.

In the context of this invention, the term "translational termination sequence" is defined as the nucleotides starting from the translational stop codon at the 3' end of the open reading frame or nucleotide coding sequence and oriented in 5' towards 3' direction.

In the context of this invention, the term "translational initiator sequence" is defined as the nucleotides immediately upstream of the initiator or start codon of the open reading frame of a sequence coding for a polypeptide.

In an embodiment the nucleic acid construct is an expression vector, wherein the polynucleotide according to the invention is operably linked to at least one control sequence for the expression of the polynucleotide in a host cell.

An expression vector comprises a polynucleotide coding for a polypeptide, operably linked to the appropriate control sequences (such as a promoter, and transcriptional and translational stop signals) for expression and/or translation in vitro or in a host cell. Certain vectors are capable of directing the expression of genes to which they are operatively linked. Such vectors are referred to herein as "expression vectors". In general, expression vectors of utility in recombinant DNA techniques are often in the form of plasmids.

The expression vector may be any vector (e.g. a plasmid or virus), which can be conveniently subjected to recombinant DNA procedures and can bring about the expression of the polynucleotide. The choice of the vector will typically depend on the compatibility of the vector with the cell into which the vector is to be introduced. The vectors may be linear or closed circular plasmids. The vector may be an autonomously replicating vector, i.e. a vector which exists as an extra-chromosomal entity, the replication of which is independent of chromosomal replication, e.g. a plasmid, an extra-chromosomal element, a mini-chromosome, or an artificial chromosome. Alternatively, the vector may be one which, when introduced into the host cell, is integrated into the genome and replicated together with the chromosome(s) into which it has been integrated. The integrative cloning vector may integrate at random or at a predetermined target locus in the chromosomes of the host cell.

The vector system may be a single vector or plasmid or two or more vectors or plasmids, which together contain the total DNA to be introduced into the genome of the host cell, or a transposon.

The vectors preferably contain one or more selectable markers which permit easy selection of transformed cells.

Another aspect of the invention pertains to vectors, including cloning and expression vectors, comprising a polynucleotide of the invention encoding and methods of growing, transforming or transfecting such vectors in a suitable host cell, for example under conditions in which expression of a polypeptide of the invention occurs.

As used herein, the term "vector" refers to a nucleic acid molecule capable of transporting another nucleic acid to which it has been linked. Thus in a further embodiment the invention provides a method of making polynucleotides of the invention by introducing a polynucleotide of the invention into a replicable vector, introducing the vector into a compatible host cell, and growing the host cell under conditions which bring about replication of the vector. The vector may be recovered from the host cell. Suitable host cells are described below.

One type of vector is a "plasmid", which refers to a circular double stranded DNA loop into which additional DNA segments can be ligated. Another type of vector is a viral vector, wherein additional DNA segments can be ligated into the viral genome. The terms "plasmid" and "vector" can be used interchangeably herein as the plasmid is the most commonly used form of vector. However, the invention is intended to include such other forms of expression vectors, such as cosmids, viral vectors (e.g. replication defective retroviruses, adenoviruses and adeno-associated viruses) and phage vectors which serve equivalent functions.

Vectors according to the invention may be used in vitro, for example for the production of RNA or used to transfect or transform a host cell.

A vector of the invention may comprise two or more, for example three, four or five polynucleotides of the invention, for example for overexpression.

The recombinant expression vectors of the invention comprise a polynucleotide of the invention in a form suitable for expression of the polynucleotide in a host cell, which means that the recombinant expression vector includes one or more regulatory sequences selected on the basis of the host cells to be used for expression, which is operably linked to the nucleotide sequence to be expressed.

The term "operably linked", "operatively linked" or "in operative association" as used herein refers to two or more nucleotide sequence elements that are physically linked and are in a functional relationship with each other. For instance, a promoter is operably linked to a coding sequence, if the promoter is able to initiate or regulate the transcription or expression of a coding sequence, in which case the coding sequence should be understood as being "under the control of" the promoter. Generally, when two nucleotide sequences are operably linked, they will be in the same orientation and usually also in the same reading frame. They usually will be essentially contiguous, although this may not be required.

A vector or nucleic construct for a given host cell may thus comprise the following elements operably linked to each other in a consecutive order from the 5'-end to the 3'-end relative to the coding strand of the sequence encoding the polypeptide of the invention: (1) a promoter sequence capable of directing transcription of the nucleotide sequence encoding the polypeptide in the given host cell, (2) optionally, a signal sequence capable of directing secretion of the polypeptide from the given host cell into a culture medium, (3) a nucleotide sequence of the invention encoding a mature and preferably active form of the polypeptide of the invention, and preferably also (4) a transcription termination region (terminator) capable of terminating transcription downstream of the nucleotide sequence encoding the polypeptide of the invention.

Downstream of the nucleotide sequence according to the invention there may be a 3'-untranslated region containing one or more transcription termination sites (e.g. a terminator). The terminator can, for example, be native to the nucleotide sequence encoding the polypeptide. However, preferably a yeast terminator is used in yeast host cells and a filamentous fungal terminator is used in filamentous fungal host cells. More preferably, the terminator is endogenous to the host cell (in which the nucleotide sequence encoding the polypeptide is to be expressed). In the transcribed region, a ribosome binding site for translation may be present. The coding portion of the mature transcripts expressed by the constructs will include a translation initiating AUG at the beginning and a termination codon appropriately positioned at the end of the polypeptide to be translated.

Enhanced expression of the polynucleotide of the invention may also be achieved by the selection of heterologous regulatory regions, e.g. promoter, secretion leader and/or terminator regions, which may serve to increase expression and, if desired, secretion levels of the polypeptide of the invention from the expression host and/or to provide for the inducible control of the expression of the polypeptide of the invention.

It will be appreciated by those skilled in the art that the design of the expression vector can depend on such factors as the choice of the host cell to be transformed, the level of expression of the polypeptide, etc.

The vectors, such as expression vectors, of the invention can be introduced into host cells to produce the polypeptide of the invention. The vectors, such as recombinant expression vectors, of the invention can be designed for expression of the polypeptides in prokaryotic or eukaryotic cells.

The recombinant expression vector can also be transcribed and translated in vitro, for example using T7 promoter regulatory sequences and T7 polymerase.

For most filamentous fungi and yeast, the vector or nucleic acid construct is preferably integrated in the genome of the host cell in order to obtain stable transformants. However, for certain yeasts also suitable episomal vectors are available into which the expression construct can be incorporated for stable and high-level expression. Examples thereof include vectors derived from the 2μ and pKD1 plasmids of *Saccharomyces* and *Kluyveromyces*, respectively, or vectors containing an AMA sequence (e.g. AMA1 from *Aspergillus*). In case the expression constructs are integrated in the host cells genome, the constructs are either integrated at random loci in the genome or at predetermined target loci using homologous recombination, in which case the target loci preferably comprise a highly expressed gene.

Accordingly, expression vectors useful in the present invention include chromosomal-, episomal- and virus-derived vectors, e.g. vectors derived from bacterial plasmids, bacteriophage, yeast episome, yeast chromosomal elements, viruses such as baculoviruses, papova viruses, vaccinia viruses, adenoviruses, fowl pox viruses, pseudorabies viruses and retroviruses, and vectors derived from combinations thereof, such as those derived from plasmid and bacteriophage genetic elements, such as cosmids and phagemids.

The term "control sequence" or "regulatory sequence" can be used interchangeably with the term "expression-regulating nucleic acid sequence". The term as used herein refers to nucleotide sequences necessary for and/or affecting the expression of an operably linked coding sequence in a particular host organism or in vitro. When two nucleic acid sequences are operably linked, they usually will be in the same orientation and also in the same reading frame. They usually will be essentially contiguous, although this may not be required. The expression-regulating nucleic acid sequences, such as inter alia appropriate transcription initiation, termination, promoter, leader, signal peptide, propeptide, prepro-peptide, or enhancer sequences; Shine-Delgarno sequence, repressor or activator sequences; efficient RNA processing signals such as splicing and polyadenylation signals; sequences that stabilize cytoplasmic mRNA; sequences that enhance translation efficiency (e.g. ribosome binding sites); sequences that enhance protein stability; and when desired, sequences that enhance protein secretion, can be any nucleotide sequence showing activity in the host organism of choice and can be derived from genes encoding proteins, which are either homologous or heterologous to the host organism. Each control sequence may be native or foreign to the nucleotide sequence encoding the polypeptide. When desired, the control sequence may be provided with linkers for the purpose of introducing specific restriction sites facilitating ligation of the control sequences with the coding region of the nucleic acid sequence encoding a polypeptide. Control sequences may be optimized to their specific purpose.

The control sequence may be an appropriate promoter sequence, a nucleotide sequence, which is recognized by a host cell for expression of the nucleotide sequence. The promoter sequence contains transcriptional control sequences, which mediate the expression of the polypeptide. The promoter may be any nucleotide sequence, which shows transcriptional activity in the cell including mutant, truncated, and hybrid promoters, and may be obtained from genes encoding extracellular or intracellular polypeptides, either homologous or heterologous to the cell.

The term "promoter" is defined herein as a nucleotide sequence that binds RNA polymerase and directs the polymerase to the correct downstream transcriptional start site of a nucleotide sequence encoding a biological compound to initiate transcription. RNA polymerase effectively catalyses the assembly of messenger RNA complementary to the appropriate DNA strand of a coding region. The term "promoter" will also be understood to include the 5'-non-coding region (between promoter and translation start) for translation after transcription into mRNA, cis-acting transcription control elements such as enhancers, and other nucleotide sequences capable of interacting with transcription factors. The promoter may be any appropriate promoter sequence suitable for a eukaryotic or prokaryotic host cell, which shows transcriptional activity, including mutant, truncated, and hybrid promoters, and may be obtained from polynucleotides encoding extra-cellular or intracellular polypeptides either homologous (native) or heterologous (foreign) to the cell.

The promoter may be a constitutive or inducible promoter. Preferably, the promoter is an inducible promoter. More preferably the promoter is a carbohydrate inducible promoter. Carbohydrate inducible promoters are known in the art. In a preferred embodiment the promoter is suitable in filamentous fungi. Such promoters are known in the art. In a preferred embodiment the promoter is a *Rasamsonia* promoter. Preferably, the promoter sequence is from a highly expressed gene. Highly expressed genes are known in the art.

The promoters used in the host cells of the invention may be modified, if desired, to affect their control characteristics. Suitable promoters in this context include both constitutive and inducible natural promoters as well as engineered promoters, which are well known to the person skilled in the art.

Transcription of the nucleotide sequence encoding the polypeptides of the present invention by higher eukaryotes may be increased by inserting an enhancer sequence into the vector. Enhancers are cis-acting elements of DNA, usually about from 10 to 300 base pairs, that act to increase transcriptional activity of a promoter in a given host cell type. Examples of suitable enhancers are well known to the person skilled in the art.

The control sequence may also be a suitable transcription terminator sequence, a sequence recognized by a host cell to terminate transcription. The terminator sequence is operably linked to the 3'-terminus of the nucleotide sequence encoding the polypeptide. Any terminator, which is functional in the cell, may be used in the present invention. Examples of suitable transcription terminator sequences are well known to the person skilled in the art.

The control sequence may also include a suitable leader sequence, a non-translated region of a mRNA which is important for translation by the host cell. The leader sequence is operably linked to the 5'-terminus of the nucleotide sequence encoding the polypeptide. Any leader sequence, which is functional in the cell, may be used in the present invention. Examples of suitable leader sequences are well known to the person skilled in the art.

The control sequence may also be a polyadenylation sequence, a sequence which is operably linked to the 3'-terminus of the nucleotide sequence and which, when transcribed, is recognized by the host cell as a signal to add poly-adenosine residues to transcribed mRNA. Any polyadenylation sequence, which is functional in the cell, may be used in the present invention. Examples of suitable polyadenylation sequences are well known to the person skilled in the art.

When the polypeptide according to the invention is to be secreted from the host cell into the cultivation medium, an appropriate signal sequence can be added to the polypeptide in order to direct the de novo synthesized polypeptide to the secretion route of the host cell. The person skilled in the art knows to select an appropriate signal sequence for a specific host. The signal sequence may be native to the host cell, or may be foreign to the host cell. As an example, a signal sequence from a protein native to the host cell can be used. Preferably, said native protein is a highly secreted protein. Examples of suitable signal sequences are well known to the person skilled in the art.

As an alternative for a signal sequence, the polypeptide of the invention can be fused to a secreted carrier protein, or part thereof. Such chimeric construct is directed to the secretion route by means of the signal sequence of the carrier protein or part thereof. In addition, the carrier protein will provide a stabilizing effect to the polypeptide according to the invention and or may enhance solubility. Such carrier protein may be any protein. Preferably, a highly secreted protein is used as a carrier protein. The carrier protein may be native or foreign to the polypeptide according to the invention. The carrier protein may be native of may be foreign to the host cell. The carrier protein and polypeptide according to the invention may contain a specific amino acid motif to facilitate isolation of the polypeptide. The polypeptide according to the invention may be released by a special releasing agent. The releasing agent may be a proteolytic enzyme or a chemical agent. Examples of suitable carrier proteins are well known to the person skilled in the art.

As an alternative for secretion of the polypeptide of the invention into the medium, the polypeptide of the invention can be fused to a localisation sequence to target the polypeptide of the invention to a desired cellular compartment, organelle of a cell, or membrane. Such sequences are known to the person skilled in the art and include organelle targeting sequences.

Alternatively, the polypeptide of the invention is fused to another protein that has carbohydrate degrading activity.

Optionally, the polypeptide of the invention is flanked on the C-terminal and/or the N-terminal side by an amino acid motif that facilitates identification, isolation and/or purification.

Host Cells

In an embodiment the host cell comprises a polypeptide according to the invention, a polynucleotide according to the invention or a nucleic acid construct according to the invention.

The term "host cell" as used herein means any type of cell that is susceptible to transformation, transfection, transduction or the like with a polynucleotide according to the invention or a nucleic acid construct according to the invention. It encompasses any progeny of a parent cell that is not identical to the parent cell due to mutations that occur during replication.

The polypeptides of the present invention can be expressed in both prokaryotic and eukaryotic cells.

A prokaryotic host cell includes, but is not limited to, a bacterial host cell. The term "bacterial cell" includes both Gram-negative and Gram-positive microorganisms. Examples of bacteria include, but are not limited to, bacteria belonging to the genus *Bacillus* (e.g. *B. subtilis, B. amyloliquefaciens, B. licheniformis, B. puntis, B. megaterium, B. halodurans, B. pumilus*), *Acinetobacter, Nocardia, Xanthobacter, Escherichia* (e.g. *E. coli*), *Streptomyces, Erwinia, Klebsiella, Serratia* (e.g. *S. marcessans*), *Pseudomonas* (e.g. *P. aeruginosa*), *Salmonella* (e.g. *S. typhimurium, S. typhi*). Bacteria also include, but are not limited to, photosynthetic bacteria (e.g. green non-sulfur bacteria (e.g. *Choroflexus, Chloronema*), green sulfur bacteria (e.g. *Chlorobium, Pelodictyon*), purple sulfur bacteria (e.g. *Chromatium*), and purple non-sulfur bacteria (e.g. *Rhodospirillum, Rhodobacter*, and *Rhodomicrobium*).

A eukaryotic host cell includes, but is not limited to, a yeast host cell, a nematode host cell, a fungal host cell, an amoeba host cell, an avian host cell, an amphibian host cell, a reptilian host cell, an algal host cell, a mammalian host cell and an insect host cell.

Suitable host cells are discussed further in Goeddel, Gene Expression Technology: Methods in Enzymology 185, Academic Press, San Diego, Calif. (1990). Representative examples of appropriate host cells are described below. Appropriate culture mediums and conditions for the below-described host cells are known in the art.

In a preferred embodiment the host cells are fungal cells, preferably filamentous fungal cells, more preferably *Rasamsonia* cells, most preferred *Rasamsonia emersonii* cells.

"Filamentous fungi" are herein defined as eukaryotic microorganisms that include all filamentous forms of the subdivision *Eumycotina* and *Oomycota* (as defined by Hawksworth et al., 1995). Filamentous fungal strains include, but are not limited to, strains of *Acremonium, Aspergillus, Agaricus, Aureobasidium, Cryptococcus, Corynascus, Chrysosporium, Filibasidium, Fusarium, Humicola, Magnaporthe, Monascus, Mucor, Myceliophthora, Mortierella, Neocallimastix, Neurospora, Paecilomyces, Penicillium, Piromyces, Phanerochaete Podospora, Pycnoporus,* *Rhizopus, Schizophyllum, Sordaria, Talaromyces, Rasamsonia, Thermoascus, Thielavia, Tolypocladium, Trametes* and *Trichoderma*. Preferred filamentous fungal strains that may serve as host cells belong to the species *Aspergillus niger, Aspergillus oryzae, Aspergillus fumigatus, Penicillium chrysogenum, Penicillium citrinum, Acremonium chrysogenum, Trichoderma reesei, Rasamsonia emersonii* (formerly known as *Talaromyces emersonii*), *Aspergillus sojae, Chrysosporium lucknowense, Myceliophtora thermophyla*.

Preferred yeast host cells may be selected from the genera: *Saccharomyces* (e.g. *S. cerevisiae, S. bayanus, S. pastorianus, S. carlsbergensis*), *Kluyveromyces, Candida* (e.g. *C. revkaufi, C. pulcherrima, C. tropicalis, C. utilis*), *Pichia* (e.g. *P. pastoris*), *Schizosaccharomyces, Hansenula, Kloeckera, Schwanniomyces,* and *Yarrowia* (e.g. *Y. lipolytica* (formerly classified as *Candida lipolytica*)).

Examples of insect cells, include, but are not limited to, *Drosophila, Spodoptera* and *Trichoplusa*. Examples of nematode cells, include, but are not limited to, *C. elegans* cells. Examples of amphibian cells, include, but are not limited to, *Xenopus laevis* cells). Examples of mammalian cells, include, but are not limited to, NIH3T3, 293, CHO, COS, VERO, C127, BHK, Per-C6, Bowes melanoma and HeLa cells.

In the context of the present invention the "parent host cell" and the "mutant host cell" may be any type of host cell. The specific embodiments of the mutant host cell are described below. It will be clear to those skilled in the art that embodiments applicable to the mutant host cell are as well applicable to the parent host cell, unless otherwise indicated.

The polynucleotide may be heterologous to the genome of the host cell. The term "heterologous" as used herein refers to nucleotide or amino acid sequences not naturally occurring in a host cell. In other words, the nucleotide or amino acid sequence is not identical to that naturally found in the host cell. As used herein, the term "endogenous" or "homologous" refers to a nucleotide or amino acid sequence naturally occurring in a host.

In another embodiment, the invention features host cells, e.g. transformed host cells or recombinant host cells that contain a nucleic acid encompassed by the invention. A "transformed cell" or "recombinant cell" is a cell into which (or into an ancestor of which) has been introduced, by means of recombinant DNA techniques, a nucleic acid according to the invention.

As used herein, the terms "transformed" or "transgenic" with reference to a cell mean that the cell has a non-native (heterologous) nucleotide sequence integrated into its genome or has an episomal plasmid that is maintained through multiple generations. The term is synonymous with the term "recombinant" or "genetically modified".

A host cell can be chosen that modulates the expression of the inserted sequences or modifies and processes the gene product in a specific, desired fashion. Such modifications (e.g. glycosylation) and processing (e.g. cleavage) of polypeptide products may facilitate optimal functioning of the polypeptides.

Various host cells have characteristic and specific mechanisms for post-translational processing and modification of polypeptides and gene products. Appropriate cell lines or host systems familiar to those of skill in the art of molecular biology and/or microbiology can be chosen to ensure the desired and correct modification and processing of the foreign polypeptide expressed. To this end, eukaryotic host cells that possess the cellular machinery for proper processing of the primary transcript, glycosylation, and phosphorylation of the gene product can be used. Such host cells are well known in the art.

A host cell as defined herein is an organism suitable for genetic manipulation and one which may be cultured at cell densities useful for industrial production of a target product. A suitable organism may be a microorganism, for example one which may be maintained in a fermentation device. A host cell may be a host cell found in nature or a host cell derived from a parent host cell after genetic manipulation or classical mutagenesis.

According to one embodiment of the invention, when the mutant host cell according to the invention is a filamentous fungal host cell, the mutant host cell may comprise one or more modifications in its genome such that the mutant host cell is deficient in the production of at least one product selected from glucoamylase (glaA), acid stable alpha-amylase (amyA), neutral alpha-amylase (amyBI and amyBII), oxalic acid hydrolase (oahA), a toxin, preferably ochratoxin and/or fumonisin, a protease transcriptional regulator prtT, PepA, a product encoded by the gene hdfA and/or hdfB, a non-ribosomal peptide synthase npsE if compared to a parent host cell and measured under the same conditions.

Therefore, when the mutant microbial host cell according to the invention is a filamentous fungal host cell, the host cell may comprise one or more modifications in its genome to result in a deficiency in the production of the major extracellular aspartic protease PepA. For example, the host cell according to the invention may further comprise a disruption of the pepA gene encoding the major extracellular aspartic protease PepA.

When the mutant microbial host cell according to the invention is a filamentous fungal host cell, the host cell according to the invention may additionally comprises one or more modifications in its genome to result in a deficiency in the production of the product encoded by the hdfA (Ku70) and/or hdfB (Ku80) gene. For example, the host cell according to the invention may further comprise a disruption of the hdfA and/or hdfB gene.

When the mutant host cell according to the invention is a filamentous fungal host cell, the host cell according to the invention may additionally comprise a modification in its genome which results in the deficiency in the production of the non-ribosomal peptide synthase npsE.

Host cells according to the invention include plant cells and the invention therefore extends to transgenic organisms, such as plants and parts thereof, which contain one or more cells of the invention. The cells may heterologous express the polypeptide of the invention or may heterologous contain one or more of the polynucleotides of the invention. The transgenic (or genetically modified) plant may therefore have inserted (e.g. stably) into its genome a sequence encoding one or more of the polypeptides of the invention. The transformation of plant cells can be performed using known techniques.

In an embodiment the gene encoding for the endogenous LPMO is deleted or modified in such a way that the endogenous LPMO polypeptide is no longer produced by the host cells of the invention. Consequently, the only LPMO comprised in the host cells may be the polypeptide of the invention.

Polypeptide Production

The invention also relates to a process for producing a polypeptide according to the invention, which method comprises the steps of (a) cultivating a host cell according to the invention under conditions conducive to the production of the polypeptide, and (b) optionally, recovering the polypeptide.

The host cells according to the invention may be cultured using procedures known in the art. For each combination of a promoter and a host cell, culture conditions are available which are conducive to the expression of the polynucleotide sequence encoding the polypeptide of the invention. After reaching the desired cell density or titer of the polypeptide, the culture is stopped and the polypeptide is recovered using known procedures.

The fermentation medium can comprise a known culture medium containing a carbon source, a nitrogen source, and an inorganic nutrient sources. Optionally, an inducer may be included.

The selection of the appropriate medium may be based on the choice of expression host and/or based on the regulatory requirements of the nucleic acid construct. Such media are known to those skilled in the art. The medium may, if desired, contain additional components favoring the transformed host cell over other potentially contaminating microorganisms.

The fermentation can be performed over a period of from about 0.5 to about 30 days. It may be a batch, continuous or fed-batch process, suitably at a temperature in the range of 0-100° C. or 0-80° C., for example from 0 to 50° C. and/or at a pH from 2 to 10. Preferred fermentation conditions are a temperature in the range of from 20° C. to 45° C. and/or at a pH of from 3 to 9. The appropriate conditions are usually selected based on the choice of the host cell and the polypeptide to be expressed.

After fermentation, if necessary, the cells can be removed from the fermentation broth by means of centrifugation or filtration. After fermentation has stopped or after removal of the cells, the polypeptide of the invention may then be recovered and, if desired, purified and isolated by conventional means.

The polypeptide according to the invention can be recovered and purified from recombinant host cell cultures by methods known in the art. Most preferably, high performance liquid chromatography ("HPLC") is employed for purification.

If desired, a host cell as described above may be used to in the preparation of a polypeptide according to the invention. Such a method typically comprises cultivating a host cell (e.g. transformed or transfected with a nucleic acid construct as described above) under conditions to provide for expression of a coding sequence encoding the polypeptide, and optionally recovering the expressed polypeptide. Polynucleotides of the invention can be incorporated into a recombinant replicable vector, e.g. an expression vector. The vector may be used to replicate the nucleic acid in a compatible host cell. Thus, in a further embodiment, the invention provides a method of making a polynucleotide of the invention by introducing a polynucleotide of the invention into a replicable vector, introducing the vector into a compatible host cell, and growing the host cell under conditions which bring about the replication of the vector. The vector may be recovered from the host cell.

Preferably, the polypeptide is produced as a secreted protein in which case the nucleotide sequence encoding the polypeptide in the expression construct is operably linked to a nucleotide sequence encoding a signal sequence. Preferably, the signal sequence is native (homologous) to the nucleotide sequence encoding the polypeptide. Alternatively, the signal sequence is foreign (heterologous) to the nucleotide sequence encoding the polypeptide, in which case the signal sequence is preferably endogenous to the host cell in which the nucleotide sequence according to the invention is expressed.

In an embodiment the polypeptides of the present invention may be overexpressed in a host cell compared to the parent host cell in which the polypeptide is not overexpressed. Overexpression of a polypeptide is defined herein as the expression of the polypeptide which results in an activity of the polypeptide in the host cell being at least 1.1-, at least 1.25- or at least 1.5-fold the activity of the polypeptide in the parent host cell wherein the polypeptide is not overexpressed.

Preferably, the activity of the polypeptide is at least 2-fold, more preferably at least 3-fold, more preferably at least 4-fold, more preferably at least 5-fold, even more preferably at least 10-fold and most preferably at least 20-fold the activity of the polypeptide in the parent host cell.

Transformation of the host cell may be conducted by any suitable known methods, including electroporation methods, particle bombardment or micro projectile bombardment, protoplast methods and Agrobacterium mediated transformation (AMT).

In order to enhance the amount of copies of the polynucleotide coding for the polypeptide or coding for a compound involved in the production by the cell of the polypeptide in the mutated host cell, multiple transformations of the host cell may be required. In this way, the ratios of the different polypeptides produced by the host cell may be influenced. Also, an expression vector may comprise multiple expression cassettes to increase the amount of copies of the polynucleotide(s) to be transformed.

Another way could be to choose different control sequences for the different polynucleotides, which—depending on the choice—may cause a higher or a lower production of the desired polypeptide(s).

The host cells transformed with the selectable marker can be selected based on the presence of the selectable marker.

For stable transfection of mammalian cells, it is known that, depending upon the expression vector and transfection technique used, only a small fraction of cells may integrate the foreign polynucleotide into their genome. In order to identify and select these integrants, a gene that encodes a selectable marker (e.g. resistance to antibiotics) is generally introduced into the host cells along with the polynucleotide of interest. Preferred selectable markers include, but are not limited to, those which confer resistance to drugs or which complement a defect in the host cell. The selectable marker may be introduced into the cell on the expression vector as the expression cassette or may be introduced on a separate expression vector.

Preferred selectable markers include, but are not limited to, those which confer resistance to drugs or which complement a defect in the host cell. Alternatively, specific selection markers can be used such as auxotrophic markers which require corresponding mutant host cells. In a preferred embodiment the selection marker is deleted from the transformed host cell after introduction of the expression construct, so as to obtain transformed host cells which are free of selection marker genes.

As indicated, the expression vectors will preferably contain selectable markers.

Vectors preferred for use in bacteria are for example disclosed in WO-A1-2004/074468, which are hereby enclosed by reference. Other suitable vectors will be readily apparent to the skilled artisan.

The invention provides a polypeptide having the amino acid sequence according to SEQ ID NO: 1, 4, 7, 10, 13, 16, 19, 22, 25, 28, 31, 34, 37, 40, 43 and/or 46 or SEQ ID NO: 2, 5, 8, 11, 14, 17, 20, 23, 26, 29, 32, 35, 38, 41, 44, and/or 47. The invention also provides an amino acid sequence obtainable by expressing the polynucleotide of SEQ ID NO: 3, 6, 9, 12, 15, 18, 21, 24, 27, 30, 33, 36, 39, 42, 45 and/or 48 in an appropriate host.

An example of a protein or polypeptide having biological activity in an industrial application is an enzyme. Enzymes are used in the chemical industry and other industrial applications when specific catalysts are required. Enzymes in general are limited in the number of reactions they have evolved to catalyze and their deactivation at high temperatures. As a consequence, protein engineering is an active area of research and involves attempts to create new enzymes with novel properties, either through rational design or in vitro evolution. These efforts have begun to be successful, and a few enzymes have now been designed to improve enzymatic reactions. For designing it is essential to have starting sequences from useful microorganisms especially thermophilic microorganisms like fungi.

Enzymes can be categorized using their Enzyme Commission number (EC number) which is a numerical classification scheme for enzymes, based on the chemical reactions they catalyze.

Cellulosic Material

Cellulosic materials (also called "biomass" or "feedstock" or "lignocellulosic material" herein) are abundant in nature and have great value as alternative energy source. Second generation biofuels, also known as advanced biofuels, are fuels that can be manufactured from various types of biomass. Biomass can be derived from plant materials, but can also include animal materials. The composition of biomass varies, the major component is cellulose (in general 35-50%), followed by xylan (a type of hemicellulose, in general 20-35%) and lignin (in general 10-25%), in addition to minor components such as proteins, oils and ash (or inorganic compounds) that make up the remaining fraction of biomass. Biomass contains a variety of carbohydrates. The term carbohydrate is most common in biochemistry, where it is a synonym of saccharide. Carbohydrates (saccharides) are divided into four chemical groupings: monosaccharides, disaccharides, oligosaccharides, and polysaccharides. In general, monosaccharides and disaccharides, which are smaller (lower molecular weight) carbohydrates, are commonly referred to as sugars. The enzymatic conversion (such as hydrolysis) of polysaccharides to soluble sugars, for example glucose, gluconic acid, xylose, arabinose, galactose, fructose, mannose, rhamnose, ribose, D-galacturonic acid and other hexoses and pentoses occurs under the action of different enzymes acting in concert.

A composition of the invention may be tailored in view of the particular feedstock which is to be used. That is to say, the spectrum of activities in a composition of the invention may vary depending on the feedstock in question.

The enzymes used to hydrolyze the feedstock can be produced either exogenously in microorganisms such as yeasts, fungi, bacteria or plants, then isolated and added to the feedstock. Alternatively, the enzymes can be produced, but not isolated, and a whole fermentation broth, or a combination of enzymes and a whole fermentation broth, can be added to the feedstock. Alternatively, the whole fermentation broth may be treated to prevent further microbial growth (for example, by heating or addition of antimicrobial agents), then added to the feedstock. The whole fermentation broth may include the organism producing the enzyme(s). Alternatively, the enzyme may be produced in a fermentation that uses feedstock (such as corn stover) to provide nutrition to an organism that produces an enzyme(s). In this manner, plants that produce the enzymes may serve as the feedstock and be added to feedstock.

Example of suitable cellulosic materials include, but are not limited to, virgin biomass and/or non-virgin biomass such as agricultural biomass, commercial organics, construction and demolition debris, municipal solid waste, waste paper and yard waste. Common forms of biomass include trees, shrubs and grasses, wheat, wheat straw, sugar cane bagasse, corn, corn husks, corn cobs, corn kernel including fiber from kernels, distillers dried grains, products and by-products from milling of grains such as corn, wheat and barley (including wet milling and dry milling) often called "bran or fiber" as well as municipal solid waste, waste paper and yard waste. The biomass can also be, but is not limited to, herbaceous material, agricultural residues, forestry residues, municipal solid wastes, waste paper, and pulp and paper mill residues. "Agricultural biomass" includes branches, bushes, canes, corn and corn husks, energy crops, forests, fruits, flowers, grains, grasses, herbaceous crops, leaves, bark, needles, logs, roots, saplings, short rotation woody crops, shrubs, switch grasses, trees, vegetables, fruit peels, vines, sugar beet pulp, wheat middlings, oat hulls, and hard and soft woods (not including woods with deleterious materials). In addition, agricultural biomass includes organic waste materials generated from agricultural processes including farming and forestry activities, specifically including forestry wood waste. Agricultural biomass may be any of the afore-stated singularly or in any combination or mixture thereof. Further examples of suitable biomass are orchard primings, chaparral, mill waste, urban wood waste, municipal waste, logging waste, forest thinnings, short-rotation woody crops, industrial waste, wheat straw, oat straw, rice straw, cane straw, barley straw, rye straw, flax straw, soy hulls, rice hulls, rice straw, corn gluten feed, oat hulls, sugar cane, corn stover, corn stalks, corn cobs, corn husks, prairie grass, gama grass, foxtail; sugar beet pulp, citrus fruit pulp, seed hulls, cellulosic animal wastes, lawn clippings, cotton, seaweed, trees, shrubs, grasses, wheat, wheat straw, sugar cane bagasse, corn, corn husks, corn hobs, corn kernel, fiber from kernels, products and by-products from wet or dry milling of grains, municipal solid waste, waste paper, yard waste, herbaceous material, agricultural residues, forestry residues, municipal solid waste, waste paper, pulp, paper mill residues, branches, bushes, canes, corn, corn husks, an energy crop, forest, a fruit, a flower, a grain, a grass, a herbaceous crop, a leaf, bark, a needle, a log, a root, a sapling, a shrub, switch grass, a tree, a vegetable, fruit peel, a vine, sugar beet pulp, wheat middlings, oat hulls, hard or soft wood, organic waste material generated from an agricultural process, forestry wood waste, or a combination of any two or more thereof.

Apart from virgin biomass or feedstocks already processed in food and feed or paper and pulping industries, the biomass/feedstock may additionally be pretreated with heat, mechanical and/or chemical modification or any combination of such methods in order to enhance enzymatic degradation.

Pretreatment

Before enzymatic treatment, the feedstock may optionally be pretreated with heat, mechanical and/or chemical modification or any combination of such methods in order to enhance the accessibility of the substrate to enzymatic hydrolysis and/or hydrolyse the hemicellulose and/or solubilize the hemicellulose and/or cellulose and/or lignin, in any way known in the art. The pretreatment may comprise exposing the cellulosic material to (hot) water, steam (steam explosion), an acid, a base, a solvent, heat, a peroxide, ozone, mechanical shredding, grinding, milling or rapid depressurization, or a combination of any two or more thereof. This chemical pretreatment is often combined with heat-pretreatment, e.g. between 150 and 220° C. for 1 to 30 minutes.

In an embodiment the cellulosic material is pretreated before and/or during the enzymatic hydrolysis. Pretreatment methods are known in the art and include, but are not limited to, heat, mechanical, chemical modification, biological modification and any combination thereof.

Pretreatment is typically performed in order to enhance the accessibility of the cellulosic material to enzymatic hydrolysis and/or hydrolyse the hemicellulose and/or solubilize the hemicellulose and/or cellulose and/or lignin, in the cellulosic material. In an embodiment, the pretreatment comprises treating the cellulosic material with steam explosion, hot water treatment or treatment with dilute acid or dilute base. Examples of pretreatment methods include, but are not limited to, steam treatment (e.g. treatment at 100-260° C., at a pressure of 7-45 bar, at neutral pH, for 1-10 minutes), dilute acid treatment (e.g. treatment with 0.1-5% $H_2SO_4$ and/or $SO_2$ and/or $HNO_3$ and/or HCl, in presence or absence of steam, at 120-200° C., at a pressure of 2-15 bar, at acidic pH, for 2-30 minutes), organosolv treatment (e.g. treatment with 1-1.5% $H_2SO_4$ in presence of organic solvent and steam, at 160-200° C., at a pressure of 7-30 bar, at acidic pH, for 30-60 minutes), lime treatment (e.g. treatment with 0.1-2% $NaOH/Ca(OH)_2$ in the presence of water/steam at 60-160° C., at a pressure of 1-10 bar, at alkaline pH, for 60-4800 minutes), ARP treatment (e.g. treatment with 5-15% $NH_3$, at 150-180° C., at a pressure of 9-17 bar, at alkaline pH, for 10-90 minutes), AFEX treatment (e.g. treatment with >15% $NH_3$, at 60-140° C., at a pressure of 8-20 bar, at alkaline pH, for 5-30 minutes).

Hydrolysis

The invention also relates to a process for degrading cellulosic material, the process comprising the step of contacting the cellulosic material with a polypeptide according to the invention or a composition according to the invention. The degradation may result in the production of a sugar.

The invention also relates to a process for the treatment of a cellulosic material which process comprises the step of contacting the cellulosic material with a polypeptide according to the invention or a composition according to the invention. The treatment may result in the production of a sugar.

The invention also relates to a process for the preparation of a sugar product from cellulosic material, comprising the steps of (a) enzymatic hydrolysis of the cellulosic material using a polypeptide according to the invention or a composition according to the invention to obtain enzymatically hydrolysed cellulosic material, and, optionally, recovery of the enzymatically hydrolysed cellulosic material.

In an embodiment the pH of the above processes is between 3.0 and 6.5, preferably between 3.5 and 5.5, more preferably between 4.0 and 5.0.

After the processes have been performed, the cellulosic material may be subjected to at least one solid/liquid separation. The methods and conditions of solid/liquid separation will depend on the type of cellulosic material used and are well within the scope of the skilled artisan. Examples include, but are not limited to, centrifugation, cyclonic separation, filtration, decantation, sieving and sedimentation. In a preferred embodiment the solid/liquid separation is performed by centrifugation or sedimentation. During solid/liquid separation, means and/or aids for improving the separation may be used.

In an embodiment the cellulosic material is subjected to a pretreatment step before the above processes. In an embodiment the cellulosic material is subjected to a washing step before the above processes. In an embodiment the cellulosic material is subjected to at least one solid/liquid separation before the above processes. So, before subjecting the cellulosic material to any of the above processes, it can be subjected to at least one solid/liquid separation. The solid/liquid separation may be done before and/or after the pretreatment step. Suitable methods and conditions for a solid/liquid separation have been described above.

In an embodiment the invention relates to processes wherein the enzymatically hydrolysed cellulosic material is subjected to a solid/liquid separation step followed by a detoxification step and/or a concentration step.

In the processes according to the present invention cellulosic material may be added to the one or more containers. In an embodiment the polypeptide of the invention or composition of the invention is already present in the one or more containers before the cellulosic material is added. In another embodiment the polypeptide of the invention or composition of the invention may be added to the one or more containers. In an embodiment the cellulosic material is already present in the one or more containers before the polypeptide of the invention or the composition of the invention is added. In an embodiment both the cellulosic material and the polypeptide of the invention or the composition of the invention are added simultaneously to the one or more containers. The composition present in the one or more containers may be an aqueous composition.

The above processes may comprise a liquefaction step wherein the cellulosic material is liquefied, and a saccharification step wherein the liquefied cellulosic material is saccharified. The liquefaction step is sometimes called pre-saccharification step. In an embodiment the processes comprise at least a liquefaction step wherein the cellulosic material is liquefied in at least a first container, and a saccharification step wherein the liquefied cellulosic material is saccharified in the at least first container and/or in at least a second container. Saccharification can be done in the same container as the liquefaction (i.e. the at least first container), it can also be done in a separate container (i.e. the at least second container). So, in the processes according to the present invention liquefaction and saccharification may be combined. Alternatively, the liquefaction and saccharification may be separate steps. Liquefaction and saccharification may be performed at different temperatures, but may also be performed at a single temperature. In an embodiment the temperature of the liquefaction is higher than the temperature of the saccharification. Liquefaction is preferably carried out at a temperature of 60-75° C. and saccharification is preferably carried out at a temperature of 50-65° C.

The processes can be performed in one or more containers, but can also be performed in one or more tubes or any other continuous system. This also holds true when the above processes comprise a liquefaction step and a saccharification step. The liquefaction step can be performed in one or more containers, but can also be performed in one or more tubes or any other continuous system and/or the saccharification step can be performed in one or more containers, but can also be performed in one or more tubes or any other continuous system. Examples of containers to be used in the present invention include, but are not limited to, fed-batch stirred containers, batch stirred containers, continuous flow stirred containers with ultrafiltration, and continuous plug-flow column reactors. Stirring can be done by one or more impellers, pumps and/or static mixers.

The polypeptides or compositions used in the above processes may be added before and/or during the processes. As indicated above, when the cellulosic material is subjected to a solid/liquid separation before the above processes, the polypeptides or compositions used in the above processes may be added before the solid/liquid separation. Alternatively, they may also be added after solid/liquid separation or before and after solid/liquid separation. The polypeptides or compositions may also be added during the above processes. In case the above processes comprise a liquefaction step and saccharification step, additional polypeptides or compositions may be added during and/or after the liquefaction step. The additional polypeptides or compositions may be added before and/or during the saccharification step. Additional polypeptides or compositions may also be added after the saccharification step.

In an embodiment the total process time is 10 hours or more, 12 hours or more, 14 hours or more, 16 hours or more, 18 hours or more, 20 hours or more, 30 hours or more, 40 hours or more, 50 hours or more, 60 hours or more, 70 hours or more, 80 hours or more, 90 hours or more, 100 hours or more, 110 hours or more, 120 hours or more, 130 hours or more, 140 hours or more, 150 hours or more, 160 hours or more, 170 hours or more, 180 hours or more, 190 hours or more, 200 hours or more.

In an embodiment, the total process time is 10 to 300 hours, 16 to 275 hours, preferably 20 to 250 hours, more preferably 30 to 200 hours, most preferably 40 to 150 hours.

The viscosity of the cellulosic material in the one or more containers used for the above processes is kept between 10 and 4000 cP, between 10 and 2000 cP, preferably between 10 and 1000 cP.

Incubation of cellulosic material under the above conditions results in release or liberation of a substantial amount of the sugars from the cellulosic material. By substantial amount is meant at least 20%, 30%, 40%, 50%, 60%, 70%, 80%, 90%, 95% or more of the available sugasr.

In case the processes comprise a liquefaction step and a saccharification step, the viscosity of the cellulosic material in the liquefaction step is kept between 10 and 4000 cP, between 10 and 2000 cP, preferably between 10 and 1000 cP and/or the viscosity of the cellulosic material in the saccharification step is kept between 10 and 1000 cP, between 10 and 900 cP, preferably between 10 and 800 cP.

The viscosity can be determined with a Brookfield DV III Rheometer at the temperature used for the above processes.

Significantly, the above processes may be carried out using high levels of dry matter (of the cellulosic material). In an embodiment the dry matter content at the end of the above processes is 5 wt % or higher, 6 wt % or higher, 7 wt % or higher, 8 wt % or higher, 9 wt % or higher, 10 wt % or higher, 11 wt % or higher, 12 wt % or higher, 13 wt % or higher, 14 wt % or higher, 15 wt % or higher, 16 wt % or higher, 17 wt % or higher, 18 wt % or higher, 19 wt % or higher, 20 wt % or higher, 21 wt % or higher, 22 wt % or higher, 23 wt % or higher, 24 wt % or higher, 25 wt % or higher, 26 wt % or higher, 27 wt % or higher, 28 wt % or higher, 29 wt % or higher, 30 wt % or higher, 31 wt % or higher, 32 wt % or higher, 33 wt % or higher, 34 wt % or higher, 35 wt % or higher, 36 wt % or higher, 37 wt % or higher, 38 wt % or higher or 39 wt % or higher. In an embodiment the dry matter content at the end of the above processes is between 5 wt %-40 wt %, 6 wt %-40 wt %, 7 wt %-40 wt %, 8 wt %-40 wt %, 9 wt %-40 wt %, 10 wt %-40 wt %, 11 wt %-40 wt %, 12 wt %-40 wt %, 13 wt %-40 wt %, 14 wt %-40 wt %, 15 wt %-40 wt %, 16 wt %-40 wt %, 17 wt %-40 wt %, 18 wt %-40 wt %, 19 wt %-40 wt %, 20 wt %-40 wt %, 21 wt %-40 wt %, 22 wt %-40 wt %, 23 wt %-40 wt %, 24 wt %-40 wt %, 25 wt %-40 wt %, 26 wt %-40 wt %, 27 wt %-40 wt %, 28 wt %-40 wt %, 29 wt %-40 wt %, 30 wt %-40 wt %, 31 wt %-40 wt %, 32 wt %-40 wt %, 33 wt %-40 wt %, 34 wt %-40 wt %, 35 wt %-40 wt %, 36 wt %-40 wt %, 37 wt %-40 wt %, 38 wt %-40 wt %, 39 wt %-40 wt %. In a preferred embodiment the dry matter content is from 10 wt % to 25 wt %.

In an embodiment the dry matter content at the end of the liquefaction step of the above processes is 5 wt % or higher, 6 wt % or higher, 7 wt % or higher, 8 wt % or higher, 9 wt % or higher, 10 wt % or higher, 11 wt % or higher, 12 wt % or higher, 13 wt % or higher, 14 wt % or higher, 15 wt % or higher, 16 wt % or higher, 17 wt % or higher, 18 wt % or higher, 19 wt % or higher, 20 wt % or higher, 21 wt % or higher, 22 wt % or higher, 23 wt % or higher, 24 wt % or higher, 25 wt % or higher, 26 wt % or higher, 27 wt % or higher, 28 wt % or higher, 29 wt % or higher, 30 wt % or higher, 31 wt % or higher, 32 wt % or higher, 33 wt % or higher, 34 wt % or higher, 35 wt % or higher, 36 wt % or higher, 37 wt % or higher, 38 wt % or higher or 39 wt % or higher. In an embodiment the dry matter content at the end of the liquefaction step of the the above processes is between 5 wt %-40 wt %, 6 wt %-40 wt %, 7 wt %-40 wt %, 8 wt %-40 wt %, 9 wt %-40 wt %, 10 wt %-40 wt %, 11 wt %-40 wt %, 12 wt %-40 wt %, 13 wt %-40 wt %, 14 wt %-40 wt %, 15 wt %-40 wt %, 16 wt %-40 wt %, 17 wt %-40 wt %, 18 wt %-40 wt %, 19 wt %-40 wt %, 20 wt %-40 wt %, 21 wt %-40 wt %, 22 wt %-40 wt %, 23 wt %-40 wt %, 24 wt %-40 wt %, 25 wt %-40 wt %, 26 wt %-40 wt %, 27 wt %-40 wt %, 28 wt %-40 wt %, 29 wt %-40 wt %, 30 wt %-40 wt %, 31 wt %-40 wt %, 32 wt %-40 wt %, 33 wt %-40 wt %, 34 wt %-40 wt %, 35 wt %-40 wt %, 36 wt %-40 wt %, 37 wt %-40 wt %, 38 wt %-40 wt %, 39 wt %-40 wt %. In a preferred embodiment the dry matter content is from 10 wt % to 25 wt %.

In an embodiment the dry matter content at the end of the saccharification step of the above processes is 5 wt % or higher, 6 wt % or higher, 7 wt % or higher, 8 wt % or higher, 9 wt % or higher, 10 wt % or higher, 11 wt % or higher, 12 wt % or higher, 13 wt % or higher, 14 wt % or higher, 15 wt % or higher, 16 wt % or higher, 17 wt % or higher, 18 wt % or higher, 19 wt % or higher, 20 wt % or higher, 21 wt % or higher, 22 wt % or higher, 23 wt % or higher, 24 wt % or higher, 25 wt % or higher, 26 wt % or higher, 27 wt % or higher, 28 wt % or higher, 29 wt % or higher, 30 wt % or higher, 31 wt % or higher, 32 wt % or higher, 33 wt % or higher, 34 wt % or higher, 35 wt % or higher, 36 wt % or higher, 37 wt % or higher, 38 wt % or higher or 39 wt % or higher. In an embodiment the dry matter content at the end of the saccharification step of the above processes is between 5 wt %-40 wt %, 6 wt %-40 wt %, 7 wt %-40 wt %, 8 wt %-40 wt %, 9 wt %-40 wt %, 10 wt %-40 wt %, 11 wt %-40 wt %, 12 wt %-40 wt %, 13 wt %-40 wt %, 14 wt %-40 wt %, 15 wt %-40 wt %, 16 wt %-40 wt %, 17 wt %-40 wt %, 18 wt %-40 wt %, 19 wt %-40 wt %, 20 wt %-40 wt %, 21 wt %-40 wt %, 22 wt %-40 wt %, 23 wt %-40 wt %, 24 wt %-40 wt %, 25 wt %-40 wt %, 26 wt %-40 wt %, 27 wt %-40 wt %, 28 wt %-40 wt %, 29 wt %-40 wt %, 30 wt %-40 wt %, 31 wt %-40 wt %, 32 wt %-40 wt %, 33 wt %-40 wt %, 34 wt %-40 wt %, 35 wt %-40 wt %, 36 wt %-40 wt %, 37 wt %-40 wt %, 38 wt %-40 wt %, 39 wt %-40 wt %. In a preferred embodiment the dry matter content is from 10 wt % to 25 wt %.

In an embodiment oxygen is added during the above processes. In an embodiment oxygen is added during at least a part of the above processes. Oxygen can be added continuously or discontinuously during the above processes. In an embodiment oxygen is added one or more times during the above processes. In an embodiment oxygen may be added before the above processes, during the addition of cellulosic material to a container used for the above processes, during the addition of enzyme to a container used for the above processes, during a part of the above processes, during the whole processes or any combination thereof. Oxygen is added to the one or more containers used in the above processes.

Oxygen can be added in several forms. For example, oxygen can be added as oxygen gas, oxygen-enriched gas, such as oxygen-enriched air, or air. Oxygen may also be added by means of in situ oxygen generation. For example, oxygen may be generated by electrolysis, oxygen may be produced enzymatically, e.g. by the addition of peroxide, or oxygen may be produced chemically, e.g. by an oxygen generating system such as $KHSO_5$. For example, oxygen is produced from peroxide by catalase. The peroxide can be added in the form of dissolved peroxide or generated by an enzymatic or chemical reaction. In case catalase is used as enzyme to produce oxygen, catalase present in the enzyme composition for the hydrolysis can be used or catalase can be added for this purpose.

Examples how to add oxygen include, but are not limited to, addition of oxygen by means of sparging, electrolysis, chemical addition of oxygen, filling the one or more containers used in the the above processes from the top (plunging the hydrolysate into the tank and consequently introducing oxygen into the hydrolysate) and addition of oxygen to the headspace of said one or more containers. When oxygen is added to the headspace of the container(s), sufficient oxygen necessary for the hydrolysis reaction may be supplied. In general, the amount of oxygen added to the container(s) can be controlled and/or varied. Restriction of the oxygen supplied is possible by adding only oxygen during part of the hydrolysis time in said container(s). Another option is adding oxygen at a low concentration, for example by using a mixture of air and recycled air (air leaving the container) or by "diluting" air with an inert gas. Increasing the amount of oxygen added can be achieved by addition of oxygen during longer periods of the hydrolysis time, by adding the oxygen at a higher concentration or by adding more air. Another way to control the oxygen concentration is to add an oxygen consumer and/or an oxygen generator. Oxygen can be introduced, for example blown, into the liquid hydrolysis container contents of cellulosic material. It can also be blown into the headspace of the container.

In an embodiment oxygen is added to the one or more containers used in the above processes before and/or during and/or after the addition of the cellulosic material to said one or more containers. The oxygen may be introduced together with the cellulosic material that enters the hydrolysis container(s). The oxygen may be introduced into the material stream that will enter the container(s) or with part of the container(s) contents that passes an external loop of the container(s).

In an embodiment the container(s) used in the the above processes and/or the fermentation have a volume of at least 1 m³. Preferably, the containers have a volume of at least 1 m³, at least 2 m³, at least 3 m³, at least 4 m³, at least 5 m³, at least 6 m³, at least 7 m³, at least 8 m³, at least 9 m³, at least 10 m³, at least 15 m³, at least 20 m³, at least 25 m³, at least 30 m³, at least 35 m³, at least 40 m³, at least 45 m³, at least 50 m³, at least 60 m³, at least 70 m³, at least 75 m³, at least 80 m³, at least 90 m³, at least 100 m³, at least 200 m³, at least 300 m³, at least 400 m³, at least 500 m³, at least 600 m³, at least 700 m³, at least 800 m³, at least 900 m³, at least 1000 m³, at least 1500 m³, at least 2000 m³, at least 2500 m³. In general, the container(s) will be smaller than 3000 m³ or 5000 m³. In a preferred embodiment the containers used in the processes of the invention have a volume of 10 m³ to 5000 m³, preferably 50 m³ to 5000 m³. In case several containers are used in the the above processes, they may have the same volume, but also may have a different volume. In case the above processes comprise a separate liquefaction step and saccharification step the container(s) used for the liquefaction step and the container(s) used for the saccharification step may have the same volume, but also may have a different volume.

Hydrolysis and fermentation (see below), separate or simultaneous, include, but are not limited to, separate hydrolysis and fermentation (SHF); simultaneous saccharification and fermentation (SSF); simultaneous saccharification and co-fermentation (SSCF); hybrid hydrolysis and fermentation (HHF); separate hydrolysis and co-fermentation (SHCF); hybrid hydrolysis and co-fermentation (HHCF); and direct microbial conversion (DMC), also sometimes called consolidated bioprocessing (CBP).

Fermentation

The present invention also relates to a process for producing a fermentation product, the process comprising the steps of (a) enzymatically hydrolysing a cellulosic material with a polypeptide according to the present invention or a composition according to the present invention, (b) fermenting the enzymatically hydrolysed cellulosic material to produce a fermentation product, and (c) optionally, recovering of the fermentation product.

For instance, in the process of the invention a polypeptide according to the present invention or a composition according to the present invention acts on a cellulosic material, so as to convert this complex substrate to simple sugars and oligosaccharides for the production of fermentation products.

The invention thus also provides a process for the preparation of a fermentation product, which method comprises (a) degrading cellulosic material using a process as described herein, and (b) fermentation of the resulting material, thereby to prepare a fermentation product. The process for the preparation of a fermentation product may optionally comprise recovery of the fermentation product.

In an embodiment the fermentation (i.e. step b) is performed in one or more containers. In an embodiment the fermentation is done by an alcohol producing microorganism to produce alcohol. The alcohol producing microorganism may produce, for example, ethanol. In an embodiment the fermentation is done by an organic acid producing microorganism to produce an organic acid. The fermentation by an alcohol producing microorganism to produce alcohol can be done in the same container(s) wherein the step (a) is performed. Alternatively, the fermentation by an alcohol producing microorganism to produce alcohol and the fermentation by an organic acid producing microorganism to produce an organic acid can be performed in one or more separate containers, but may also be done in one or more of the same containers.

In an embodiment the fermentation is done by a yeast. In an embodiment the alcohol producing microorganism and/or the organic acid producing microorganism is a yeast. In an embodiment the alcohol producing microorganism is able to ferment at least a C5 sugar and at least a C6 sugar. In an embodiment the organic acid producing microorganism is able to ferment at least a C6 sugar. In an embodiment the alcohol producing microorganism and the organic acid producing microorganism are different microorganisms. In another embodiment the alcohol producing microorganism and the organic acid producing microorganism are the same microorganism, i.e. the alcohol producing microorganism is also able to produce organic acid such as succinic acid.

In a further aspect, the invention thus includes fermentation processes in which a microorganism is used for the fermentation of a carbon source comprising sugar(s), e.g. glucose, L-arabinose and/or xylose. The carbon source may include any carbohydrate oligo- or polymer comprising L-arabinose, xylose or glucose units, such as e.g. lignocellulose, xylans, cellulose, starch, arabinan and the like. For release of xylose or glucose units from such carbohydrates, appropriate carbohydrases (such as xylanases, glucanases, amylases and the like) may be added to the fermentation medium or may be produced by the modified host cell. In the latter case, the modified host cell may be genetically engineered to produce and excrete such carbohydrases. An additional advantage of using oligo- or polymeric sources of glucose is that it enables to maintain a low(er) concentration of free glucose during the fermentation, e.g. by using rate-limiting amounts of the carbohydrases. This, in turn, will prevent repression of systems required for metabolism and transport of non-glucose sugars such as xylose. In a preferred process the modified host cell ferments both the L-arabinose (optionally xylose) and glucose, preferably simultaneously in which case preferably a modified host cell is used which is insensitive to glucose repression to prevent diauxic growth. In addition to a source of L-arabinose, optionally xylose (and glucose) as carbon source, the fermentation medium will further comprise the appropriate ingredient required for growth of the modified host cell. Compositions of fermentation media for growth of microorganisms such as yeasts or filamentous fungi are well known in the art.

The fermentation time may be shorter than in conventional fermentation at the same conditions, wherein part of the enzymatic hydrolysis still has to take part during fermentation. In one embodiment, the fermentation time is 100 hours or less, 90 hours or less, 80 hours or less, 70 hours or less, or 60 hours or less, for a sugar composition of 50 g/l glucose and corresponding other sugars from the cellulosic material (e.g. 50 g/l xylose, 35 g/l L-arabinose and 10 g/l galactose). For more dilute sugar compositions, the fermentation time may correspondingly be reduced. In an embodiment where the fermentation process is one for the production of an alcohol such as ethanol, the fermentation time of the ethanol production step is between 10 and 50 hours for ethanol made out of C6 sugars and between 20 and 100 hours for ethanol made out of C5 sugars. In an embodiment where the fermentation process is one for the production of an organic acid such as succinic acid, the fermentation time of the succinic acid production step is between 20 and 70 hours.

The fermentation process may be an aerobic or an anaerobic fermentation process. An anaerobic fermentation process is herein defined as a fermentation process run in the absence of oxygen or in which substantially no oxygen is consumed, preferably less than 5, 2.5 or 1 mmol/L/h, more preferably 0 mmol/L/h is consumed (i.e. oxygen consumption is not detectable), and wherein organic molecules serve as both electron donor and electron acceptors. In the absence of oxygen, NADH produced in glycolysis and biomass formation, cannot be oxidised by oxidative phosphorylation. To solve this problem many micro-organisms use pyruvate or one of its derivatives as an electron and hydrogen acceptor thereby regenerating $NAD^+$. Thus, in a preferred anaerobic fermentation process pyruvate is used as an electron (and hydrogen acceptor) and is reduced to fermentation products such as ethanol, lactic acid, 3-hydroxy-propionic acid, acrylic acid, acetic acid, succinic acid, citric acid, malic acid, fumaric acid, an amino acid, 1,3-propane-diol, ethylene, glycerol, butanol, a β-lactam antibiotic and a cephalosporin. In a preferred embodiment, the fermentation process is anaerobic. An anaerobic process is advantageous, since it is cheaper than aerobic processes: less special equipment is needed. Furthermore, anaerobic processes are expected to give a higher product yield than aerobic processes. Under aerobic conditions, usually the biomass yield is higher than under anaerobic conditions. As a consequence, usually under aerobic conditions, the expected product yield is lower than under anaerobic conditions.

In another embodiment, the fermentation process is under oxygen-limited conditions. More preferably, the fermentation process is aerobic and under oxygen-limited conditions. An oxygen-limited fermentation process is a process in which the oxygen consumption is limited by the oxygen transfer from the gas to the liquid. The degree of oxygen limitation is determined by the amount and composition of the ingoing gas flow as well as the actual mixing/mass transfer properties of the fermentation equipment used. Preferably, in a process under oxygen-limited conditions, the rate of oxygen consumption is at least 5.5, more preferably at least 6 and even more preferably at least 7 mmol/L/h.

In an embodiment the alcohol fermentation process is anaerobic, while the organic acid fermentation process is aerobic, but done under oxygen-limited conditions.

The fermentation process is preferably run at a temperature that is optimal for the microorganism used. Thus, for most yeasts or fungal cells, the fermentation process is performed at a temperature which is less than 42° C., preferably 38° C. or lower. For yeast or filamentous fungal host cells, the fermentation process is preferably performed at a temperature which is lower than 35, 33, 30 or 28° C. and at a temperature which is higher than 20, 22, or 25° C. In an embodiment the alcohol fermentation step and the organic acid fermentation step are performed between 25° C. and 35° C.

In an embodiment of the invention, the fermentations are conducted with a fermenting microorganism. In an embodiment of the invention, the alcohol (e.g. ethanol) fermentations of C5 sugars are conducted with a C5 fermenting microorganism. In an embodiment of the invention, the alcohol (e.g. ethanol) fermentations of C6 sugars are conducted with a C5 fermenting microorganism or a commercial C6 fermenting microorganism. Commercially available yeast suitable for ethanol production include, but are not limited to, BIOFERM™ AFT and XR (NABC—North American Bioproducts Corporation, Ga., USA), ETHANOL RED™ yeast (Fermentis/Lesaffre, USA), FALI™ (Fleischmann's Yeast, USA), FERMIOL™ (DSM Specialties), GERT STRAND™ (Gert Strand AB, Sweden), and SUPERSTART™ and THERMOSACC™ fresh yeast (Ethanol Technology, Wis., USA).

In an embodiment propagation of the alcohol producing microorganism and/or the organic acid producing microorganism is performed in one or more propagation containers. After propagation, the alcohol producing microorganism and/or the organic acid producing microorganism may be added to one or more fermentation containers. Alternatively, the propagation of the alcohol producing microorganism and/or the organic acid producing microorganism is combined with the fermentation by the alcohol producing microorganism and/or the organic acid producing microorganism to produce alcohol and/or organic acid, respectively.

In an embodiment the alcohol producing microorganism is a microorganism that is able to ferment at least one C5 sugar. Preferably, it also is able to ferment at least one C6 sugar. In an embodiment the invention relates to a process for the preparation of ethanol from cellulosic material, comprising the steps of (a) performing a process for the preparation of a sugar product from cellulosic material as described above, (b) fermentation of the enzymatically hydrolysed cellulosic material to produce ethanol; and (c) optionally, recovery of the ethanol. The fermentation can be done with a microorganism that is able to ferment at least one C5 sugar.

In an embodiment the organic acid producing microorganism is a microorganism that is able to ferment at least one C6 sugar. In an embodiment the invention relates to a process for the preparation of succinic acid from cellulosic material, comprising the steps of (a) performing a process for the preparation of a sugar product from cellulosic material as described above, (b) fermentation of the enzymatically hydrolysed cellulosic material to produce succinic acid; and (c) optionally, recovery of the succinic acid. The fermentation can be done with a microorganism that is able to ferment at least one C6 sugar.

The alcohol producing microorganisms may be a prokaryotic or eukaryotic organism. The microorganism used in the process may be a genetically engineered microorganism. Examples of suitable alcohol producing organisms are yeasts, for instance *Saccharomyces*, e.g. *Saccharomyces cerevisiae*, *Saccharomyces pastorianus* or *Saccharomyces uvarum*, *Hansenula*, *Issatchenkia*, e.g. *Issatchenkia orientalis*, *Pichia*, e.g. *Pichia stipites* or *Pichia pastoris*, *Kluyveromyces*, e.g. *Kluyveromyces fagilis*, *Candida*, e.g. *Candida pseudotropicalis* or *Candida acidothermophilum*, *Pachysolen*, e.g. *Pachysolen tannophilus* or bacteria, for instance *Lactobacillus*, e.g. *Lactobacillus lactis*, *Geobacillus*, *Zymomonas*, e.g. *Zymomonas mobilis*, *Clostridium*, e.g. *Clostridium phytofermentans*, *Escherichia*, e.g. *E. coli*, *Klebsiella*, e.g. *Klebsiella oxytoca*. In an embodiment the microorganism that is able to ferment at least one C5 sugar is a yeast. In an embodiment, the yeast belongs to the genus *Saccharomyces*, preferably of the species *Saccharomyces cerevisiae*. The yeast, e.g. *Saccharomyces cerevisiae*, used in the processes according to the present invention is capable of converting hexose (C6) sugars and pentose (C5) sugars. The yeast, e.g. *Saccharomyces cerevisiae*, used in the processes according to the present invention can anaerobically ferment at least one C6 sugar and at least one C5 sugar. For example, the yeast is capable of using L-arabinose and xylose in addition to glucose anaerobically. In an embodiment, the yeast is capable of converting L-arabinose into L-ribulose and/or xylulose 5-phosphate and/or into a desired fermentation product, for example into ethanol. Organisms, for example *Saccharomyces cerevisiae* strains, able to produce ethanol from L-arabinose may be produced by modifying a host yeast introducing the araA (L-arabinose isomerase), araB (L-ribuloglyoxalate) and araD (L-ribulose-5-P4-epimerase) genes from a suitable source. Such genes may be introduced into a host cell in order that it is capable of using arabinose. Such an approach is given is described in WO2003/095627. araA, araB and araD genes from *Lactobacillus plantarum* may be used and are disclosed in WO2008/041840. The araA gene from *Bacillus subtilis* and the araB and araD genes from *Escherichia coli* may be used and are disclosed in EP1499708. In another embodiment, araA, araB and araD genes may derived from of at least one of the genus *Clavibacter, Arthrobacter* and/or *Gramella*, in particular one of *Clavibacter michiganensis, Arthrobacter aurescens,* and/or *Gramella forsetii,* as disclosed in WO 2009011591. In an embodiment, the yeast may also comprise one or more copies of xylose isomerase gene and/or one or more copies of xylose reductase and/or xylitol dehydrogenase.

The yeast may comprise one or more genetic modifications to allow the yeast to ferment xylose. Examples of genetic modifications are introduction of one or more xy/A-gene, XYL1 gene and XYL2 gene and/or XKS1-gene; deletion of the aldose reductase (GRE3) gene; overexpression of PPP-genes TAL1, TKL1, RPE1 and RKI1 to allow the increase of the flux through the pentose phosphate pathway in the cell. Examples of genetically engineered yeast are described in EP1468093 and/or WO2006/009434.

An example of a suitable commercial yeast is RN1016 that is a xylose and glucose fermenting *Saccharomyces cerevisiae* strain from DSM, the Netherlands.

In an embodiment, the fermentation process for the production of ethanol is anaerobic. Anaerobic has already been defined earlier herein. In another preferred embodiment, the fermentation process for the production of ethanol is aerobic. In another preferred embodiment, the fermentation process for the production of ethanol is under oxygen-limited conditions, more preferably aerobic and under oxygen-limited conditions. Oxygen-limited conditions have already been defined earlier herein.

The volumetric ethanol productivity is preferably at least 0.5, 1.0, 1.5, 2.0, 2.5, 3.0, 5.0 or 10.0 g ethanol per litre per hour. The ethanol yield on L-arabinose and optionally xylose and/or glucose in the process preferably is at least 20, 25, 30, 35, 40, 45, 50, 60, 70, 80, 90, 95 or 98%. The ethanol yield is herein defined as a percentage of the theoretical maximum yield, which, for glucose and L-arabinose and optionally xylose is 0.51 g ethanol per g glucose or xylose.

In one aspect, the fermentation process leading to the production of ethanol, has several advantages by comparison to known ethanol fermentations processes: anaerobic processes are possible; oxygen limited conditions are possible; higher ethanol yields and ethanol production rates can be obtained; the strain used may be able to use L-arabinose and optionally xylose.

Alternatively to the fermentation processes described above, at least two distinct cells may be used, this means this process is a co-fermentation process. All preferred embodiments of the fermentation processes as described above are also preferred embodiments of this co-fermentation process: identity of the fermentation product, identity of source of L-arabinose and source of xylose, conditions of fermentation (aerobic or anaerobic conditions, oxygen-limited conditions, temperature at which the process is being carried out, productivity of ethanol, yield of ethanol).

The organic acid producing microorganisms may be a prokaryotic or eukaryotic organism. The microorganism used in the process may be a genetically engineered microorganism. Examples of suitable organic acid producing organisms are yeasts, for instance *Saccharomyces*, e.g. *Saccharomyces cerevisiae*; fungi for instance *Aspergillus* strains, such as *Aspergillus niger* and *Aspergillus fumigatus, Byssochlamys nivea, Lentinus degener, Paecilomyces varioti* and *Penicillium viniferum*; and bacteria, for instance *Anaerobiospirillum succiniciproducens, Actinobacillus succinogenes, Mannhei succiniciproducers* MBEL 55E, *Escherichia coli, Propionibacterium* species, *Pectinatus* sp., *Bacteroides* sp., such as *Bacteroides amylophilus, Ruminococcus flavefaciens, Prevotella ruminicola, Succcinimonas amylolytica, Succinivibrio dextrinisolvens, Wolinella succinogenes,* and *Cytophaga succinicans.* In an embodiment the organic acid producing microorganism that is able to ferment at least one C6 sugar is a yeast. In an embodiment, the yeast belongs to the genus *Saccharomyces*, preferably of the species *Saccharomyces cerevisiae*. The yeast, e.g. *Saccharomyces cerevisiae,* used in the production processes of organic acid according to the present invention is capable of converting hexose (C6) sugars. The yeast, e.g. *Saccharomyces cerevisiae*, used in the processes according to the present invention can anaerobically ferment at least one C6 sugar.

The overall reaction time (or the reaction time of hydrolysis step and fermentation step together) may be reduced. In one embodiment, the overall reaction time is 300 hours or less, 200 hours or less, 150 hours or less, 140 hours or less, 130 or less, 120 hours or less, 110 hours or less, 100 hours of less, 90 hours or less, 80 hours or less, 75 hours or less, or about 72 hours at 90% glucose yield. Correspondingly, lower overall reaction times may be reached at lower glucose yield.

Fermentation products that may be produced by the processes of the invention can be any substance derived from fermentation. They include, but are not limited to, alcohol (such as arabinitol, butanol, ethanol, glycerol, methanol, 1,3-propanediol, sorbitol, and xylitol); organic acid (such as acetic acid, acetonic acid, adipic acid, ascorbic acid, acrylic acid, citric acid, 2,5-diketo-D-gluconic acid, formic acid, fumaric acid, glucaric acid, gluconic acid, glucuronic acid, glutaric acid, 3-hydroxypropionic acid, itaconic acid, lactic acid, maleic acid, malic acid, malonic acid, oxalic acid, oxaloacetic acid, propionic acid, succinic acid, and xylonic acid); ketones (such as acetone); amino acids (such as aspartic acid, glutamic acid, glycine, lysine, serine, tryptophan, and threonine); alkanes (such as pentane, hexane, heptane, octane, nonane, decane, undecane, and dodecane), cycloalkanes (such as cyclopentane, cyclohexane, cycloheptane, and cyclooctane), alkenes (such as pentene, hexene, heptene, and octene); and gases (such as methane, hydrogen ($H_2$), carbon dioxide ($CO_2$), and carbon monoxide (CO)). The fermentation product can also be a protein, a vitamin, a pharmaceutical, an animal feed supplement, a specialty chemical, a chemical feedstock, a plastic, a solvent, ethylene, an enzyme, such as a protease, a cellulase, an amylase, a glucanase, a lactase, a lipase, a lyase, an oxidoreductase, a transferase or a xylanase. In a preferred embodiment an organic acid and/or an alcohol is prepared in the fermentation processes of the present invention. In a preferred embodiment succinic acid and/or ethanol is prepared in the fermentation processes of the present invention.

Use of the Polypeptide and Composition of the Invention

The polypeptides and polypeptide compositions according to the invention may be used in many different applications. For instance, they may be used to produce fermentable sugars. The fermentable sugars can then, as part of a biofuel process, be converted into biogas or ethanol, butanol, isobutanol, 2-butanol or other fermentation product. A non-exhaustive list is given above.

By "fermentable sugars" is meant sugars which can be consumed by a microorganism or converted by a microorganism into a fermentation product.

Alternatively, a polypeptide of the invention or a composition of the invention may be used in the production of a food product, a detergent composition, in the paper and pulp industry, in antibacterial formulations, in pharmaceutical products to name just a few. Some of the uses will be illustrated in more detail below.

In the uses and methods described below, the components of the compositions described above may be provided concomitantly (i.e. as a single composition per se) or separately or sequentially.

In principle, a polypeptide of the invention or composition of the invention may be used in any process which requires the treatment of a material which comprises polysaccharide. Thus, a polypeptide or composition of the invention may be used in the treatment of polysaccharide material. Herein, polysaccharide material is a material which comprises or consists essential of one or, more typically, more than one polysaccharide.

The invention also provides use of a polypeptide or composition a described herein in a method for the preparation of biogas. Biogas typically refers to a gas produced by the biological breakdown of organic matter, for example cellulosic material, in the absence of oxygen. Biogas originates from biogenic material and is a type of biofuel. One type of biogas is produced by anaerobic digestion or fermentation of biodegradable materials such as biomass, manure or sewage, municipal waste, and energy crops. This type of biogas is comprised primarily of methane and carbon dioxide. The gas methane can be combusted or oxidized with oxygen. Air contains 21% oxygen. This energy release allows biogas to be used as a fuel. Biogas can be used as a low-cost fuel in any country for any heating purpose, such as cooking. It can also be utilized in modern waste management facilities where it can be used to run any type of heat engine, to generate either mechanical or electrical power. The first step in microbial biogas production consists in the enzymatic degradation of polymers and complex substrates. Accordingly, the invention provides a method for preparation of a biogas in which a cellulosic substrate is contacted with a polypeptide or composition of the invention, thereby to yield fermentable material which may be converted into a biogas by an organism, such as a microorganism. In such a method, a polypeptide or composition of the invention may be provided by way of an organism, for example a microorganism which expresses a polypeptide or composition of the invention.

The polypeptides and compositions of the invention may be used in a method of processing material to degrade or modify the cellulose and/or hemicellulose and/or pectic substance constituents of the material. Such methods may be useful in the preparation of a food product. Accordingly, the invention provides a method for preparing a food product which method comprises incorporating a polypeptide or composition of the invention during preparation of the food product.

The invention also provides a method of processing a cellulosic material, which method comprises contacting the cellulosic material with a polypeptide or composition of the invention to degrade or modify the cellulose in the material.

The present invention also provides a method for reducing the viscosity, clarity and/or filterability of a cellulosic material, which method comprises contacting the material with a polypeptide or composition of the invention in an amount effective in degrading cellulose and/or hemicellulose and/or pectic substances in the material. Cellulosic materials in this respect include, but are not limited to, plant pulp, parts of plants and plant extracts. In the context of this invention an extract from a plant material is any substance which can be derived from plant material by extraction (mechanical and/or chemical), processing or by other separation techniques. The extract may be juice, nectar, base or concentrate made thereof. The plant material may comprise or be derived from vegetables (e.g. carrots, celery, onions, legumes or leguminous plants (soy, soybean, peas)) or fruit (e.g., pome or seed fruit (apples, pears, quince etc.), grapes, tomatoes, citrus (orange, lemon, lime, mandarin), melons, prunes, cherries, black currants, redcurrants, raspberries, strawberries, cranberries, pineapple and other tropical fruits), trees and parts thereof (e.g. pollen, from pine trees), or cereal (oats, barley, wheat, maize, rice). The material (to be hydrolysed) may also be agricultural residues, such as sugar beet pulp, corn cobs, wheat straw, (ground) nutshells, or recyclable materials, e.g. (waste) paper. The polypeptides of the invention can thus be used to treat plant material including plant pulp and plant extracts. They may also be used to treat liquid or solid foodstuffs or edible foodstuff ingredients, or be used in the extraction of coffee, plant oils, starch or as a thickener in foods. Typically, the polypeptides of the invention are used as a composition as described above. The composition will generally be added to plant pulp obtainable by, for example mechanical processing such as crushing or milling plant material. Incubation of the composition with the plant will typically be carried out for at time of from 10 minutes to 5 hours. The processing temperature is preferably from about 10° C. to about 55° C. and one can use from about 10 g to about 300 g of enzyme per ton of material to be treated. The polypeptides or compositions of the invention may be added sequentially or at the same time to the plant pulp. Depending on the composition of the enzyme preparation the plant material may first be macerated (e.g. to a pure) or liquefied. Using the polypeptides of the invention processing parameters such as the yield of the extraction, viscosity of the extract and/or quality of the extract can be improved. Alternatively, or in addition to the above, a polypeptide or composition of the invention may be added to the raw juice obtained from pressing or liquefying the plant pulp. Treatment of the raw juice will be carried out in a similar manner to the plant pulp in respect of dosage, temperature and holding time. Again, other enzymes such as those discussed previously may be included. Typical incubation conditions are as described above. Once the raw juice has been incubated with the polypeptides or compositions of the invention, the juice is then centrifuged or (ultra) filtered to produce the final product. After treatment with the polypeptide or composition of the invention, the (end) product can be heat treated, e.g. at about 100° C. for a time of from about 1 minute to about 1 hour, under conditions to partially or fully inactivate the polypeptide or composition of the invention. A polypeptide or composition of the invention may also be used during the preparation of fruit or vegetable purees. The polypeptide or composition of the invention may also be used in brewing, wine making, distilling or baking. It may therefore be used in the preparation of alcoholic beverages such as wine and beer. For example, it may improve the filterability or clarity, for example of beers, wort (e.g. containing barley and/or sorghum malt) or wine. Furthermore, a polypeptide or composition of the invention may be used for treatment of brewers spent grain, i.e. residuals from beer wort production containing barley or malted barley or other cereals, so as to improve the utilization of the residuals for e.g. animal feed. A polypeptide or composition of the invention may assist in the removal of dissolved organic substances from broth or culture media, for example where distillery waste from organic origin is bio-converted into microbial biomass. The polypeptide or composition of the invention may improve filterability and/or reduce viscosity in glucose syrups, such as from cereals produced by liquefaction (e.g. with α-amylase). In baking, the polypeptide or composition of the invention may improve the dough structure, modify its stickiness or suppleness, improve the loaf volume and/or crumb structure or impart better textural characteristics such as break, shred or crumb quality. The present invention thus relates to methods for preparing a dough or a cereal-based food product comprising incorporating into the dough a polypeptide or composition of the present invention. This may improve one or more properties of the dough or the cereal-based food product obtained from the dough relative to a dough or a cereal-based food product in which the polypeptide or composition is not incorporated. The preparation of the cereal-based food product according to the invention further can comprise steps known in the art such as boiling, drying, frying, steaming or baking of the obtained dough. Products that are made from a dough that is boiled are for example boiled noodles, dumplings, products that are made from fried dough are for example doughnuts, beignets, fried noodles, products that are made for steamed dough are for example steamed buns and steamed noodles, examples of products made from dried dough are pasta and dried noodles and examples of products made from baked dough are bread, cookies and cake. The term "improved property" is defined herein as any property of a dough and/or a product obtained from the dough, particularly a cereal-based food product, which is improved by the action of the polypeptide or composition according to the invention relative to a dough or product in which the polypeptide or composition according to the invention is not incorporated. The improved property may include, but is not limited to, increased strength of the dough, increased elasticity of the dough, increased stability of the dough, improved machinability of the dough, improved proofing resistance of the dough, reduced stickiness of the dough, improved extensibility of the dough, increased volume of the cereal-based food product, reduced blistering of the cereal-based food product, improved crumb structure of the baked product, improved softness of the cereal-based food product, improved flavour of the cereal-based food product, improved anti-staling of the cereal-based food product. Improved properties related to pasta and noodle type of cereal-based products are for example improved firmness, reduced stickiness, improved cohesiveness and reduced cooking loss. Non-starch polysaccharides (NSP) can increase the viscosity of the digesta which can, in turn, decrease nutrient availability and animal performance. Adding specific nutrients to feed improves animal digestion and thereby reduces feed costs. Non-starch polysaccharides (NSPs) are also present in virtually all feed ingredients of plant origin. NSPs are poorly utilized and can, when solubilized, exert adverse effects on digestion. Exogenous enzymes can contribute to a better utilization of these NSPs and as a consequence reduce any anti-nutritional effects. A polypeptide or composition of the present invention can be used for this purpose in cereal-based diets for poultry and, to a lesser extent, for pigs and other species.

A polypeptide or composition of the invention may be used in the detergent industry, for example for removal from laundry of carbohydrate-based stains. A detergent composition may comprise a polypeptide or composition of the invention and, in addition, one or more of a cellulase, a hemicellulase, a pectinase, a protease, a lipase, a cutinase, an amylase or a carbohydrase. A detergent composition comprising a polypeptide or composition of the invention may be in any convenient form, for example a paste, a gel, a powder or a liquid. A liquid detergent may be aqueous, typically containing up to about 70% water and from about 0 to about 30% organic solvent or non-aqueous material. Such a detergent composition may, for example, be formulated as a hand or machine laundry detergent composition including a laundry additive composition suitable for pretreatment of stained fabrics and a rinse added fabric softener composition, or be formulated as a detergent composition for use in general household hard surface cleaning operations, or be formulated for hand or machine dish washing operations. In general, the properties of the polypeptide or composition of the invention should be compatible with the selected detergent (for example, pH-optimum, compatibility with other enzymatic and/or non-enzymatic ingredients, etc.) and the polypeptide or composition of the invention should be present in an effective amount. A detergent composition may comprise a surfactant, for example an anionic or non-ionic surfactant, a detergent builder or complexing agent, one or more polymers, a bleaching system (for example an $H_2O_2$ source) or an enzyme stabilizer. A detergent composition may also comprise any other conventional detergent ingredient such as, for example, a conditioner including a clay, a foam booster, a sud suppressor, an anti-corrosion agent, a soil-suspending agent, an an-soil redeposition agent, a dye, a bactericide, an optical brightener, a hydrotropes, a tarnish inhibitor or a perfume.

A polypeptide or composition of the present invention may be used in the paper and pulp industry, inter alia in the bleaching process to enhance the brightness of bleached pulps whereby the amount of chlorine used in the bleaching stages may be reduced, and to increase the freeness of pulps in the recycled paper process. Furthermore, a polypeptide or composition of the invention may be used for treatment of lignocellulosic pulp so as to improve the bleachability thereof. Thereby the amount of chlorine need to obtain a satisfactory bleaching of the pulp may be reduced.

A polypeptide or composition of the invention may be used in a method of reducing the rate at which cellulose-containing fabrics become harsh or of reducing the harshness of cellulose-containing fabrics, the method comprising treating cellulose-containing fabrics with a polypeptide or composition as described above. The present invention further relates to a method providing colour clarification of coloured cellulose-containing fabrics, the method comprising treating coloured cellulose-containing fabrics with a polypeptide or composition as described above, and a method of providing a localized variation in colour of coloured cellulose-containing fabrics, the method comprising treating coloured cellulose-containing fabrics with a polypeptide or composition as described above. The methods of the invention may be carried out by treating cellulose-containing fabrics during washing. However, if desired, treatment of the fabrics may also be carried out during soaking or rinsing or simply by adding the polypeptide or composition as described above to water in which the fabrics are or will be immersed.

In addition, a polypeptide or composition of the present invention can also be used in antibacterial formulation as well as in pharmaceutical products such as throat lozenges, toothpastes, and mouthwash.

Embodiments of the Invention

1. A polypeptide having cellulolytic enhancing activity, wherein the polypeptide is selected from the group consisting of:
   (a) a polypeptide comprising an amino acid sequence having at least 60% sequence identity with the amino acid sequence of SEQ ID NO: 2, 5, 8, 11, 14, 17, 20, 23, 26, 29, 32, 35, 38, 41, 44 and/or 47;
   (b) a polypeptide encoded by a polynucleotide comprising a nucleotide sequence having at least 60% sequence identity to the nucleotide sequence of SEQ ID NO: 3, 6, 9, 12, 15, 18, 21, 24, 27, 30, 33, 36, 39, 42, 45 and/or 48,
   (c) a polypeptide encoded by a polynucleotide comprising a nucleotide sequence which hybridises under at least high stringency conditions with the complementary strand of SEQ ID NO: 3, 6, 9, 12, 15, 18, 21, 24, 27, 30, 33, 36, 39, 42, 45 and/or 48, and
   (d) a fragment of the polypeptide of (a), (b), or (c), that has cellulolytic enhancing activity.

2. A polynucleotide, wherein the polynucleotide comprises a nucleotide sequence that is selected from the group consisting of:
   (a) a nucleotide sequence having at least 60% sequence identity with the nucleotide sequence of SEQ ID NO: 3, 6, 9, 12, 15, 18, 21, 24, 27, 30, 33, 36, 39, 42, 45 and/or 48,
   (b) a nucleotide sequence which hybridises under at least high stringency conditions with the complementary strand of SEQ ID NO: 3, 6, 9, 12, 15, 18, 21, 24, 27, 30, 33, 36, 39, 42, 45 and/or 48,
   (c) a fragment which is at least 100 nucleotides in length of a nucleotide sequence as defined in (a) or (b),
   (d) a nucleotide sequence which is degenerate as a result of the genetic code to a nucleotide sequence as defined in any one of (a), (b), or (c), and
   (e) a nucleotide sequence which is the complement of a nucleotide sequence as defined in (a), (b), (c), or (d).

3. A polynucleotide according to embodiment 2, which encodes a polypeptide according to embodiment 1.

4. A nucleic acid construct comprising the polynucleotide according to embodiment 2 or 3.

5. A nucleic acid construct according to embodiment 4 which is an expression vector, wherein the polynucleotide according to embodiment 2 or 3 is operably linked to at least one control sequence for the expression of the polynucleotide in a host cell.

6. A host cell comprising a polypeptide according to embodiment 1, a polynucleotide according to embodiment 2 or 3 or a nucleic acid construct according to embodiment 4 or 5.

7. A host cell according to embodiment 6 which is a fungal cell.

8. A process for producing the polypeptide according to embodiment 1, which process comprises the steps of:
   (c) cultivating a host cell according to embodiment 6 or 7 under conditions conducive to the production of the polypeptide, and
   (d) optionally, recovering the polypeptide.

9. A composition comprising:
   (a) a polypeptide according to embodiment 1, and
   (b) a cellulase and/or a hemicellulase and/or a pectinase.

10. A composition according to embodiment 9, wherein the cellulase is a cellobiohydrolase I, a cellobiohydrolase II, an endo-β-1,4-glucanase, a β-glucosidase or a β-(1,3)(1,4)-glucanase.

11. A composition according to embodiment 9 or 10, wherein the hemicellulase is an endoxylanase, a β-xylosidase, an α-L-arabinofuranosidase, an α-D-glucuronidase, an acetyl-xylan esterase, a feruloyl esterase, a coumaroyl esterase, an α-galactosidase, a β-galactosidase, a β-mannanase or a β-mannosidase.

12. A composition according to any one of the embodiments 9 to 11, wherein the composition is a whole fermentation broth.

13. Process for degrading cellulosic material, the process comprising the step of contacting the cellulosic material with a polypeptide according to embodiment 1 or a composition according to any one of the embodiments 9 to 12.

14. Process for producing a fermentation product, the process comprising the steps of:
   (d) enzymatically hydrolysing a cellulosic material with a polypeptide according to embodiment 1 or a composition according to any one of the embodiments 9 to 12,
   (e) fermenting the enzymatically hydrolysed cellulosic material to produce a fermentation product, and
   (f) optionally, recovering of the fermentation product.

15. Process according to embodiment 14, wherein the fermentation product is an alcohol, such as ethanol.

A reference herein to a patent document or other matter which is given as prior art is not to be taken as an admission that that document or matter was known or that the information it contains was part of the common general knowledge as at the priority date of any of the claims.

The disclosure of each reference set forth herein is incorporated herein by reference in its entirety.

The present invention is further illustrated by the following Examples:

EXAMPLES

General Procedures and Molecular Biology Techniques

Standard molecular cloning techniques such as DNA isolation, gel electrophoresis, enzymatic restriction modifications of nucleic acids, *E.coli transformation* e.a., were performed as described by Sambrook et al., 1989 (2nd ed) and 2001 (3rd ed), Molecular cloning: a laboratory manual, Cold Spring Harbor Laboratory Press, Cold Spring Harbor, N.Y. and Innes et al. (1990) PCR protocols, a guide to methods and applications, Academic Press, San Diego. Examples of the general design of expression vectors for gene overexpression and disruption vectors for down-regulation, transformation, use of markers, strains and selective media can be found in WO 1998/46772, WO 1999/32617, WO 2001/121779, WO 2005/095624, WO 2006/040312, EP 0 635 574B, WO 2005/100573, WO 2011/009700, WO 2012/001169, WO 2013/135729, WO 2014/013073, WO 2014/013074 and WO 2005/100573. After transformation, the removal of the selection marker by a (second) homologous recombination event is performed by using a recombinase such as detailed in WO2013135729.

Preparation of Pre-Treated, Corn Stover Substrate.

Dilute-acid pre-treated corn stover was obtained as described in Schell, D. J., Applied Biochemistry and Biotechnology (2003), vol. 105-108, pp 69-85. A pilot scale pretreatment reactor was used operating at steady state conditions of 190° C., 1 min residence time and an effective H2SO4 acid concentration of 1.45% (w/w) in the liquid phase. For the preparation of low acid pre-treated corn stover, also referred to as mildly pretreated corn stover, a pilot scale pretreatment reactor was used operating at steady state conditions of 182° C., 4.7 min residence time and an effective H2SO4 acid concentration of 0.35% (w/w) in the liquid aiming at a pH of 2.5.

Example 1

Cloning of LPMO Variants in *A. niger* and Generation of Enzyme Samples Strains

WT 1: This *A. niger* strain is used as a wild-type strain. This strain is deposited at the CBS Institute under the deposit number CBS 513.88.

WT 2: This *A. niger* strain is a WT 1 strain comprising a deletion of the gene encoding glucoamylase (glaA). WT 2 was constructed by using the "MARKER-GENE FREE" approach as described in EP 0 635 574 B1. In this patent, it is extensively described how to delete glaA specific DNA sequences in the genome of CBS 513.88. The procedure resulted in a MARKER-GENE FREE glaA recombinant *A. niger* CBS 513.88 strain, possessing finally no foreign DNA sequences at all.

WT 3: This *A. niger* strain is a WT 2 strain comprising a deletion of the pepA gene encoding the major extracellular aspartic protease PepA. The WT 3 strain is constructed by using the "MARKER-GENE FREE" approach as described in EP 0 635 574. The method described in this patent is used to delete pepA specific DNA sequences in the genome of WT 2, as described by van den Hombergh et al. (van den Hombergh J P, Sollewijn Gelpke M D, van de Vondervoort P J, Buxton F P, Visser J. (1997)—Disruption of three acid proteases in *Aspergillus niger*—effects on protease spectrum, intracellular proteolysis, and degradation of target proteins—Eur J Biochem. 247(2): 605-13). The procedure resulted in a MARKER-GENE FREE WT 3 strain, with the pepA gene inactivated in the WT 2 strain background.

WT 4: This *A. niger* strain is a WT 3 strain comprising the deletion of three genes encoding alpha-amylases (amyB, amyBI and amyBII) in three subsequent steps. The construction of deletion vectors and genomic deletion of these three genes has been described in detail in WO 2005/095624. The vectors pDEL-AMYA, pDEL-AMYBI and pDEL-AMYBII, described in WO 2005/095624, have been used according the "MARKER-GENE FREE" approach as described in EP 0 635 574 B1. The procedure described above resulted in an oxalate deficient, MARKER-GENE FREE ΔglaA, pepA, ΔamyA, ΔamyBI and ΔamyBII glucoamylase-, acid protease-, amylase-negative recombinant *A. niger* CBS 513.88 (WT 1) strain, possessing finally no foreign DNA sequences at all. As such, WT 4 has a low (gluco-)amylase background and is more optimized for enzyme expression and expression detection compared to WT 1.

Cloning and Expression of the Polypeptides of the Invention

The protein sequence of the polypeptides of the invention is shown in SEQ ID NO: 1, 4, 7, 10, 13, 16, 19 and 22 and SEQ ID NO: 2, 5, 8, 11, 14, 17, 20 and 23 (mature part).

For the polypeptides of the invention, codon-adapted DNA sequence for expression of the protein in *Aspergillus niger* was designed containing additional BsaI type II restriction enzyme sites to enable subcloning in the *Aspergillus* expression vector pGBFIN-50 (see FIG. 1). Codon adaptation was performed as described in WO 2008/000632. The codon optimized DNA sequences for expression of the genes encoding the polypeptides of the invention in *A. niger* is shown in SEQ ID NO: 3, 6, 9, 12, 15, 18, 21 and 24.

The translational initiation sequence of the glucoamylase glaA promoter was modified into 5'-CACCGTCAAAATG-3', already present in the *Aspergillus* expression vector pGBFIN-50, and an optimal translational termination sequence 5'-TAAA-3' was used in the generation of the expression constructs (as also detailed in WO 2006/077258 and WO 2011/009700). The DNA sequence coding for the LMPO variant enzyme of the invention was synthesized completely (DNA2.0, Menlo Park, USA) and cloned into *Aspergillus niger* expression vector pGBFIN-50 through repetitive steps of BsaI digestion and ligation (US 2015/0050696) according to standard procedures.

Subsequently, *A. niger* WT4 was transformed with a PCR-amplified Pgla-3'gla fragment generated using the above described vectors resulting from the GoldenGate cloning as template. The PCR fragments are comprising the LMPO expression cassette under control of the glucoamylase promoter and the hygromycin selection marker. Alternatively, a NotI-digested and purified fragment of the GoldenGate derived LMPO variant expression vector, containing the LMPO variant expression cassette individually and the hygromycin selection marker could have been used. Transformation experiments were performed with strain and methods as described in WO 1998/46772, WO 1999/32617, WO 2011/009700, WO 2012/001169, WO 2013/135729, WO 2014/013073 and WO 2014/013074 and references therein. After transformation, the protoplasts were plated onto selective regeneration medium consisting of *Aspergillus* minimal medium supplemented with 60 μg/ml Hygromycin B. After incubation for 5-10 days at 30° C., single transformants were isolated on PDA (Potato Dextrose Agar, supplemented with 60 μg/ml Hygromycin B. After 5-7 days growth at 30° C. single transformants were used for fermentations.

*Aspergillus niger* Shake Flask Fermentation

About 10⁷ spores of selected transformants and control strains were inoculated into 100 ml shake flasks with baffles containing 20 ml of liquid pre-culture medium consisting of per liter: 30 g maltose.H2O; 5 g yeast extract; 10 g hydrolyzed casein; 1 g KH2PO4; 0.5 g MgSO4.7H2O; 0.03 g ZnCl2; 0.02 g CaCl2; 0.01 g MnSO4.4H2O; 0.3 g FeSO4.7H2O; 3 g Tween-80; 10 ml penicillin (5000 IU/ml)/Streptomycin (5000 UG/ml); 0.0025 g CuSO4; pH 5.5. These cultures were grown at 34 degrees Celsius (and 170 rpm) for 16-24 hours. 10 ml of this culture was inoculated into 500 ml shake flasks with baffles containing 100 ml fermentation medium consisting of per liter: 70 g glucose.H2O; 25 g hydrolyzed casein; 12.5 g yeast extract; 1 g KH2PO4; 2 g K2SO4; 0.5 g MgSO4.7H2O; 0.03 g ZnCl2; 0.02 g CaCl2; 0.009 g MnSO4.1H2O; 0.003 g FeSO4.7H2O; 10 ml penicillin (5000 IU/ml)/Streptomycin (5000 UG/ml); 0.0025 g CuSO4; adjusted to pH5.6. These cultures were grown at 34 degrees Celsius (and 170 rpm) until all glucose was depleted (usually after 4-7 days). Samples taken from the fermentation broth were centrifuged (10 min at 5000×g) in a swinging bucket centrifuge and supernatants collected and filtered over a 0.2 μm filter (Nalgene)

Shake Flask Concentration and Protein Concentration Determination with TCA-Biuret Method In order to obtain greater amounts of material for further testing, the fermentation supernatants obtained as described above (volume between 75 and 100 ml) were concentrated using a 10 kDa spin filter to a volume of approximately 5 ml. Subsequently, the protein concentration in the concentrated supernatant was determined via a TCA-biuret method.

Concentrated protein samples (supernatants) were diluted with water to a concentration between 2 and 8 mg/ml. Bovine serum albumin (BSA) dilutions (0, 1, 2, 5, 8 and 10 mg/ml) were made and included as samples to generate a calibration curve. Of each diluted protein sample 270 µl was transferred into a 10 ml tube containing 830 µl of a 12% (w/v) trichloro acetic acid solution in acetone and mixed thoroughly. Subsequently, the tubes were incubated on ice water for one hour and centrifuged for 30 minutes, at 4° C. and 6000 rpm. The supernatant was discarded and pellets were dried by inverting the tubes on a tissue and letting them stand for 30 minutes at room temperature. Next, 3 ml BioQuant Biuret reagent mix was added to the pellet in the tube and the pellet was solubilized upon mixing followed by addition of 1 ml water. The tube was mixed thoroughly and incubated at room temperature for 30 minutes. The absorption of the mixture was measured at 546 nm with a water sample used as a blank measurement and the protein concentration was calculated via the BSA calibration line.

Example 2

Cloning of a LPMO Variant in *Rasamsonia* LPMO Knockout Strain and Generation of Enzyme Sample Strains and Enzymes The *Rasamsonia emersonii* (*R. emersonii*) strains used herein are derived from ATCC16479, which is used as wild-type strain. ATCC16479 was formerly also known as *Talaromyces emersonii* and *Penicillium geosmithia emersonii*. Upon the use of the name *Rasamsonia emersonii* also *Talaromyces emersonii* is meant. Other strain designations of *R. emersonii* MCC 16479 are CBS393.64, IF031232 and IM11 16815. *Rasamsonia* (*Talaromyces*) *emersonii* strain TEC-142 is deposited at CENTRAAL BUREAU VOOR SCHIMMELCULTURES, Uppsalalaan 8, P.O. Box 85167, NL-3508 AD Utrecht, The Netherlands on 1st July 2009 having the Accession Number CBS 124902. TEC-142S is a single isolate of TEC-142.

Molecular Biology Techniques

In this strain, using molecular biology techniques known to the skilled person (see: Sambrook & Russell, Molecular Cloning: A Laboratory Manual, 3rd Ed., CSHL Press, Cold Spring Harbor, N.Y., 2001), a LPMO knock-out derivative strain was obtained and subsequently used to over express a polypeptide of the invention as described below. Examples of the general design of expression vectors for gene over expression and disruption vectors, transformation, use of markers and selective media can be found in for example WO 1998/46772, WO 1999/32617, WO 2001/121779, WO 2005/095624, EP 0 635 574B and WO 2005/100573.

Transformation of *R. emersonii* with pDEL_Phleo Knock-Out Construct

In order to obtain a LPMO deletion derivative, *R. emersonii* was transformed with a PCR amplified fragment derived from pDel-Phleo construct. This PCR fragment consists of 2.8 kb upstream (including 800 bp native LPMO promoter) and 2.0 kb downstream sequences of the native *R. emersonii* LPMO gene. In between these flanking sequences is a lox-flanked phleomycin resistance gene located. After transformation and a homologous recombination event the native LPMO gene including the first 800 bp are exchanged by the lox-flanked phleomycin resistance gene.

*R. emersonii* transformation was performed according to the protocol described in WO 2011/054899. Transformants were selected on plates containing phleomycine and subsequently confirmed by qPCR.

Cloning and Expression of the Polypeptides of the Invention in *R emersonii*

The protein sequence of the polypeptides of the invention is set out in SEQ ID NO: 25, 28, 31, 34, 37, 40, 43 and 46 and SEQ ID NO: 26, 29, 32, 35, 38, 41, 44 and 47 (mature part).

For the polypeptides of the invention, codon-adapted DNA sequence for expression of the protein in *R. emersonii* was designed containing additional BsaI type II restriction enzyme sites to enable subcloning, together with the native LPMO promoter and terminator sequences in a standard cloning vector (ef.bbn). The DNA sequences coding for the polypeptides of the invention, as well as the 2.8 kb upstream (including the 800 bp native LPMO promoter sequences) and 2.0 kb downstream sequences flanking the native LPMO gene were synthesized completely (DNA2.0, Menlo Park, USA) and cloned into the ef.bbn vector through repetitive steps of BsaI digestion and ligation (US 2015/0050696) according standard procedure resulting in a LPMO variant expressing construct.

Subsequently, the above described *R. emersonii* LPMO deletion strain was co-transformed with above described PCR-amplified LPMO expression fragments and a lox-flanked hygromycin resistance gene fragment.

Figure 2:
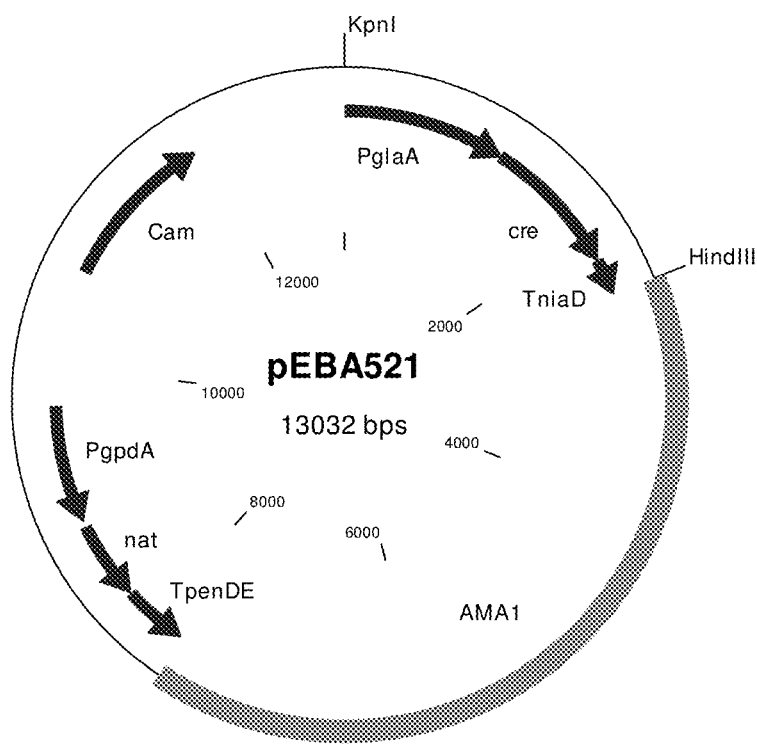
FIG. 2 sets out a schematic representation of the *Rasamsonia* Cre-recombinase expression vector pEBA521.

Transformants are selected on plates containing hygromycin antibiotic marker and subsequent qPCR analyzed on the presence of a polypeptide of the invention. Transformants with the correct characteristics were subsequently transformed with a pEBA521 vector (see FIG. 2) to transiently express the cre-recombinase enzyme to remove the lox-flanked hygromycin resistance gene by recombination over the lox66 and lox71 site.

Construction of the Cre-Recombinase Expression Vector pEBA521 was constructed by DNA2.0 (Menlo Park, USA) and contains the following components: expression cassette consisting of the *A. niger* glaA promoter, ORF encoding cre-recombinase (AAY56380) and *A. nidulans* niaD terminator; expression cassette consisting of the *A. nidulans* gpdA promoter, ORF encoding hygromycin B resistance protein and *P. chrysogenum* penDE terminator (Genbank: M31454.1, nucleotides 1750-2219); pAMPF21 derived vector containing the AMA1 region and the CAT chloramphenicol resistance gene.

Shake Flask Media for *Rasamsonia*

*Rasamsonia* medium 1: per litre: Glucose 20 g; Yeast extract (Difco) 20 g; Clerol FBA3107 (AF) 4 drops; MES 30 g; pH 6.0; Sterilize 20 min at 120° C.

*Rasamsonia* medium 2: per litre: Salt fraction no.3 10 g; glucose 10 g; KH2PO4 5 g; NaH2PO4 2 g; (NH4)2SO4 5 g; MES 30 g; pH 5.4; Sterilize 20 min at 120° C.

*Rasamsonia* medium 3: per litre: Salt fraction no.3 10 g; cellulose 20 g; KH2PO4 5 g; NaH2PO4 2 g; (NH4)2SO4 5 g; MES 30 g; pH 5.4; Sterilize 20 min at 120° C.

*Rasamsonia* medium 4: per litre: Salt fraction no.3 10 g; cellulose 15 g; glucose 5 g; KH2PO4 5 g; NaH2PO4 2 g; (NH4)2SO4 5 g; MES 30 g; pH 5.4; Sterilize 20 min at 120° C.

Spore Batch Preparation for *Rasamsonia*

Strains were grown from stocks on *Rasamsonia* agar medium in 10 cm diameter Petri dishes for 5-7 days at 40° C. For MTP fermentations, strains were grown in 96-well plates containing *Rasamsonia* agar medium. Strain stocks were stored at −80° C. in 10% glycerol.

Shake Flask Growth Protocol of *Rasamsonia*

Spores were inoculated into 100 ml shake flasks containing 20 ml of *Rasamsonia* medium 1 and incubated at 45° C. at 250 rpm in an incubator shaker for 1 day (preculture 1) and 1 or 2 ml of biomass from preculture 1 was transferred to 100 ml shake flasks containing 20 ml of *Rasamsonia* medium 2 and grown under conditions as described above for 1 day (preculture 2). Subsequently, 1 or 2 ml of biomass from preculture 2 was transferred to 100 ml shake flasks containing 20 ml of *Rasamsonia* medium 3 or 4 and grown under conditions described above for 3 days.

Protein Concentration Determination with TCA-Biuret Method

Protein samples (*Rasamsonia* supernatants) were diluted with water to a concentration between 2 and 8 mg/ml. Bovine serum albumin (BSA) dilutions (0, 1, 2, 5, 8 and 10 mg/ml) were made and included as samples to generate a calibration curve. Of each diluted protein sample 270 µl was transferred into a 10 ml tube containing 830 µl of a 12% (w/v) trichloro acetic acid solution in acetone and mixed thoroughly. Subsequently, the tubes were incubated on ice water for one hour and centrifuged for 30 minutes, at 4° C. and 6000 rpm. The supernatant was discarded and pellets were dried by inverting the tubes on a tissue and letting them stand for 30 minutes at room temperature. Next, 3 ml BioQuant Biuret reagent mix was added to the pellet in the tube and the pellet was solubilized upon mixing followed by addition of 1 ml water. The tube was mixed thoroughly and incubated at room temperature for 30 minutes. The absorption of the mixture was measured at 546 nm with a water sample used as a blank measurement and the protein concentration was calculated via the BSA calibration line.

Example 3

Cellulolytic Enhancing Activity Assay

The cellulolytic enhancing activity of the polypeptides of the invention produced according to Example 1 was analyzed as follows; the concentrated supernatant of an *A. niger* shake flask fermentation expressing a polypeptide of the invention was spiked on top of a 3E base enzyme mix. The 3E base enzyme mix was dosed at a concentration of 1.6 mg/g dry matter weight in the hydrolysis reaction and was composed of: beta-glucosidase (BG) at 0.225 mg/g dry matter weight, cellobiohydrolase I (CBHI) at 0.75 mg/g dry matter weight and cellobiohydrolase II (CBHII) at 0.625 mg/g dry matter weight (see WO 2011/098577 for details of these enzymes and their production).

The polypeptide containing supernatant was spiked on top of this 3E base mix in a final concentration of 0.9 mg of the polypeptide/g dry matter weight. The hydrolysis performance of these four enzyme mixes were compared by analyzing mono sugar release from a low acid pretreated corn stover feedstock in a concentration of 7.5% dry matter weight after an incubation of 72 hours at 62° C., pH 4.5 (pH of feedstock was adjusted to 4.5 with a 4 M NaOH solution). The hydrolysis reactions were performed in a total volume of 20 g in 40 ml centrifuge bottles (Nalgene Oakridge) which were incubated in an oven incubator (Techne HB-1 D hybridization oven), while rotating at set-point 3. As blank control, the 3 enzyme base mix (BG, CBHI and CBHII) with addition of water instead of a polypeptide of the invention was incubated with feedstock under the same conditions as described above and mono sugar release was measured. All experiments were performed in duplicate. After incubation, the samples were centrifuged and soluble sugars were analyzed by HPLC as follows.

The sugar content of the samples after enzymatic hydrolysis were analyzed using a High-Performance Liquid Chromatography System (Agilent 1100) equipped with a refection index detector (Agilent 1260 Infinity). The separation of the sugars was achieved by using a 300×7.8 mm Aminex HPX-87P (Bio rad cat no 125-0098) column; Pre-column: Micro guard Carbo-P (Bio Rad cat no 125-0119); mobile phase was HPLC grade water; flow rate of 0.6 ml/min and a column temperature of 85° C. The injection volume was 10 µl. The samples were diluted with HPLC grade water to a maximum of 2.5 g/l glucose and filtered by using 0.2 µm filter (Afridisc LC25 mm syringe filter PVDF membrane). The glucose was identified and quantified according to the retention time, which was compared to the external glucose standard (D-(+)-Glucose, Sigma cat no: G7528) ranging from 0.2; 0.4; 1.0; 2.0 g/l.

The data presented in Table 1 show that addition of the polypeptide of the invention to the 3E base mix significantly improves the glucose release from the low acid pretreated corn stover feedstock.

TABLE 1

Glucose released by 3E base mix and 3E base mix spiked with polypeptide of the invention from low acid pretreated corn stover after a 72 hrs incubation at 62° C. at pH 4.5

| Enzyme mix | Glucose (g/l) |
|---|---|
| 3E base mix | 5.29 |
| 3E base mix + polypeptide of invention (SEQ ID NO: 1 and SEQ ID NO: 2) | 7.1 |
| 3E base mix + polypeptide of invention (SEQ ID NO: 4 and SEQ ID NO: 5) | 7.3 |
| 3E base mix + polypeptide of invention (SEQ ID NO: 7 and SEQ ID NO: 8) | 6.7 |
| 3E base mix + polypeptide of invention (SEQ ID NO: 10 and SEQ ID NO: 11) | 6.9 |
| 3E base mix + polypeptide of invention (SEQ ID NO: 13 and SEQ ID NO: 14) | 7.7 |
| 3E base mix + polypeptide of invention (SEQ ID NO: 16 and SEQ ID NO: 17) | 8 |
| 3E base mix + polypeptide of invention (SEQ ID NO: 19 and SEQ ID NO: 20) | 7.4 |
| 3E base mix + polypeptide of invention (SEQ ID NO: 22 and SEQ ID NO: 23) | 7 |

Example 4

Activity Assay Using Artificial Substrate AZO-Xyloglucan

The activity of the polypeptides of the invention produced according to Example 1 was also tested in an assay using AZO-xyloglucan (obtained from Megazyme) as a substrate. A 1% Azo-xyloglucan substrate was prepared by adding 1 g of AZO-xyloglucan to 80 ml of miliQ-water. The solution was subsequently vigorously stirred for about 20 minutes and 5 ml of a 2M sodium acetate solution was added. Subsequently the pH was adjusted to 4.5 using 3 ml 4M NaOH and the volume was set to 100 ml with milliQ-water. After pre-heating 400 µl of this 1% AZO-xyloglucan solution tol 37° C., the polypeptides of the invention and a wild-type reference (concentrations ranging from 0.05-2 mg/ml) and 10 mM vitamin C (or other electron donors like cysteine and dithiothreitol) were added to a final volume of 200 µl. The mixture (0.6 ml) was incubated for 4 hours in an Eppendorf®-thermomixer at 37° C. After the incubation, the reaction was terminated by the addition of 1 ml 96% ethanol. The suspension was mixed vigorously for 10 seconds on a vortex mixer and subsequently centrifuged for 10 minutes at 1000×g at 20° C. The supernatant was pipetted into a cuvette and the absorbance at a wavelength of 590 nm was determined with a spectrophotometer, after taking a zero measurement with water.

For each experiment, a control was included where the enzyme sample was replaced by water but still containing the electron donor (vitamin C or cysteine or dithiothreitol) and the incubation of the AZO-xyloglucan was performed under the same conditions as described above. The absorption of this control sample was subtracted from the absorption value of the enzyme incubations. The height of the absorbance of the sample containing the polypeptide of the invention minus the absorbance of the control is a measurement for the activity of the enzyme; the higher the absorbance, the higher the activity of the polypeptide of the invention on this AZO-xyloglucan substrate.

The data in Table 2 show that the polypeptides of the invention are more active than a wild-type reference on this AZO-xyloglucan substrate when 10 mM dithiothreitol, 10 mM vitamin C or 10 mM cysteine were used as an electron donor and both enzymes were dosed at 0.08 mg/ml.

TABLE 2

Absorbance at 590 as indicator for LPMO activity; wild-type enzyme and polypeptides of the invention in AZO-xyloglucan assay with 10 mM dithiothreitol, 10 mM vitamin C or 10 mM cysteine as electron donor

| Enzyme | 590 nm (AU) | | |
|---|---|---|---|
| | 10 mM dithiothreitol | 10 mM vitamin C | 10 mM cysteine |
| Wild-type reference 1 | 0.25 | 0.75 | 0.44 |
| Polypeptide of invention (SEQ ID NO: 1 and SEQ ID NO: 2) | — | 0.85 | — |
| Polypeptide of invention (SEQ ID NO: 4 and SEQ ID NO: 5) | 0.26 | — | — |
| Polypeptide of invention (SEQ ID NO: 7 and SEQ ID NO: 8) | 0.32 | 0.94 | — |
| Polypeptide of invention (SEQ ID NO: 10 and SEQ ID NO: 11) | 0.34 | — | 0.47 |
| Wild-type reference 2 | 0.17 | — | 0.36 |
| Polypeptide of invention (SEQ ID NO: 13 and SEQ ID NO: 14) | 0.26 | — | — |
| Polypeptide of invention (SEQ ID NO: 16 and SEQ ID NO: 17) | — | — | — |
| Polypeptide of invention (SEQ ID NO: 19 and SEQ ID NO: 20) | 0.31 | — | 0.47 |
| Polypeptide of invention (SEQ ID NO: 22 and SEQ ID NO: 23) | 0.40 | — | 0.48 |

This AZO-xyloglucan activity assay described in this Example may be used to test the activity of the polypeptides of the invention under different conditions. The following parameters, for example, can be varied: replacement of vitamin C, dithiothreitol or cysteine for another electron donor in a different concentration, the incubation temperature, the pH, the presence of an inhibitor like for example gluconic acid or glucose, or with and without a preincubation at a certain temperature or in the presence of a certain compound like for example peroxide.

Example 5

Sugar-Release Activity Assay from (Mildly) Acid Pretreated Corn Stover Feedstock The cellulolytic activity of the polypeptides of the invention produced according to Example 2 is analyzed as follows; the supernatant of the shake flask fermentation of the Rasamsonia strain expressing the polypeptides of the invention is incubated in the presence of a low acid pretreated feedstock and the glucose release is monitored compared to a reference strain lacking the polypeptides of the invention.

In this experiment, the typical low acid pretreated corn stover concentration is between 5% and 10% dry matter. The Rasamsonia shake flask supernatant containing the polypeptide of the invention and the control supernatant without the polypeptide of the invention are incubated with the feedstock at a total protein dosage of 2.5 mg/g dry matter during the hydrolysis reaction. The hydrolysis reactions are typically performed in a total volume of 20 g in 40 ml centrifuge bottles (Nalgene Oakridge) and are incubated in an oven incubator (Techne HB-1 D hybridization oven) while rotating at set-point 3. After incubation for 72 hours at pH 4.5 at 62° C., the hydrolysis performance of the Rasamsonia supernatants are compared by analyzing mono sugar release from the low acid pretreated corn stover feedstock. After the incubation, the samples are centrifuged and soluble sugars are analyzed by HPLC as follows.

The sugar content of the samples after enzymatic hydrolysis is analyzed using a High-Performance Liquid Chromatography System (Agilent 1100) equipped with a refection index detector (Agilent 1260 Infinity). The separation of the sugars is achieved by using a 300×7.8 mm Aminex HPX-87P (Bio rad cat no 125-0098) column; Pre-column: Micro guard Carbo-P (Bio Rad cat no 125-0119); mobile phase is HPLC grade water; flow rate of 0.6 ml/min and a column temperature of 85° C. The injection volume is 10 µl. The samples are diluted with HPLC grade water to a maximum of 2.5 g/l glucose and filtered by using 0.2 µm filter (Afridisc LC25 mm syringe filter PVDF membrane). The glucose is identified and quantified according to the retention time, which is compared to the external glucose standard (D-(+)-Glucose, Sigma cat no: G7528) ranging from 0.2; 0.4; 1.0; 2.0 g/l.

The data show that the polypeptides of the invention have a higher glucose release from the low acid pretreated corn stover feedstock.

The invention claimed is:

1. A polypeptide having cellulolytic enhancing activity wherein the polypeptide comprises an amino acid sequence having at least 98% sequence identity with the amino acid sequence of SEQ ID NO: 2.

2. A polynucleotide comprising a nucleotide sequence that is selected from the group consisting of:

(a) a nucleotide sequence having at least 95% sequence identity with the nucleotide sequence of SEQ ID NO: 3, (b) a nucleotide sequence which hybridises under at least high stringency conditions with the complementary strand of SEQ ID NO: 3, wherein the high stringency conditions comprise 6×SSC at about 45° C., followed by one or more washes in 0.2×SSC, 0.1% SOS at about 65° C., (c) a nucleotide sequence which is degenerate as a result of the genetic code to a nucleotide sequence as defined in (a) or (b), and (d) a nucleotide sequence which is the complement of a nucleotide sequence as defined in (a), (b), or (c).

3. A vector comprising the polynucleotide according to claim 2.

4. An expression vector comprising the polynucleotide of claim 2 operably linked to at least one control sequence for the expression of the polynucleotide in a host cell.

5. A host cell comprising the expression vector of claim 4.

6. The host cell of claim 5, wherein the host cell is a fungal cell.

7. A process for producing the polypeptide according to claim 1 comprising:

(a) cultivating a host cell under conditions conducive to the production of the polypeptide, and
(b) optionally, recovering the polypeptide.

8. A composition comprising:
(a) the polypeptide according to claim 1,
(b) a cellulolytic enzyme selected from the group consisting of cellulase and hemicellulase, or a combination thereof, and
(c) a pectinase.

9. The composition according to claim 8, wherein the cellulase is a cellobiohydrolase I, a cellobiohydrolase II, an endo-β-1,4-glucanase, a β-glucosidase or a β-(1,3)(1,4)-glucanase.

10. The composition according to claim 8, wherein the hemicellulase is an endoxylanase, a β-xylosidase, an α-L-arabinofuranosidase, an α-D-glucuronidase, an acetyl-xylan esterase, a feruloyl esterase, a coumaroyl esterase, an α-galactosidase, a β-galactosidase, a β-mannanase or a β-mannosidase.

11. The composition according to claim 8, wherein the composition is a whole fermentation broth.

12. A process for degrading cellulosic material comprising contacting cellulosic material with the polypeptide according to claim 1 or a composition comprising the polypeptide.

13. A process for producing a fermentation product comprising:
(a) enzymatically hydrolysing a cellulosic material with the polypeptide according to claim 1 or a composition comprising the polypeptide,
(b) fermenting the enzymatically hydrolysed cellulosic material to produce a fermentation product, and
(c) optionally, recovering of the fermentation product.

14. The process according to claim 13, wherein the fermentation product is an alcohol.

15. The process according to claim 14 wherein the alcohol is ethanol.

16. The polypeptide of claim 1, wherein the polypeptide comprises SEQ ID NO: 2.

17. A polynucleotide encoding a polypeptide having the amino acid sequence of SEQ ID NO: 2 or encoding a polypeptide having an amino acid sequence at least 98% identical to SEQ ID NO: 2.

18. The polynucleotide of claim 17, which comprises the nucleotide sequence of SEQ ID NO: 3.

19. An expression vector comprising the polynucleotide of claim 17 operably linked to at least one control sequence for the expression of the polynucleotide in a host cell.

20. A fungal host cell comprising the expression vector of claim 19.

* * * * *